United States Patent
Randolph

(10) Patent No.: US 12,234,283 B2
(45) Date of Patent: *Feb. 25, 2025

(54) SYSTEM FOR CHROMATOGRAPHY COLUMN QUALIFICATION IN MANUFACTURING METHODS FOR PRODUCING ANTI-IL12/IL23 ANTIBODY COMPOSITIONS

(71) Applicant: Janssen Biotech, Inc., Horsham, PA (US)

(72) Inventor: Paul Randolph, Malvern, PA (US)

(73) Assignee: Janssen Biotech, Inc., Horsham, PA (US)

(*) Notice: Subject to any disclaimer, the term of this patent is extended or adjusted under 35 U.S.C. 154(b) by 276 days.

This patent is subject to a terminal disclaimer.

(21) Appl. No.: 17/366,360

(22) Filed: Jul. 2, 2021

(65) Prior Publication Data

US 2021/0332124 A1 Oct. 28, 2021

Related U.S. Application Data

(63) Continuation of application No. 16/389,114, filed on Apr. 19, 2019, now Pat. No. 11,079,361.

(60) Provisional application No. 62/660,340, filed on Apr. 20, 2018.

(51) Int. Cl.
| | | |
|---|---|---|
| *C07K 16/24* | (2006.01) | |
| *B01D 15/16* | (2006.01) | |
| *B01D 15/20* | (2006.01) | |
| *B01D 15/36* | (2006.01) | |
| *B01D 15/38* | (2006.01) | |
| *C07K 1/18* | (2006.01) | |
| *C07K 1/22* | (2006.01) | |
| *G01N 30/56* | (2006.01) | |
| *G01N 30/86* | (2006.01) | |
| *G01N 35/00* | (2006.01) | |

(52) U.S. Cl.
CPC .......... *C07K 16/244* (2013.01); *B01D 15/166* (2013.01); *B01D 15/20* (2013.01); *B01D 15/206* (2013.01); *B01D 15/362* (2013.01); *B01D 15/363* (2013.01); *B01D 15/3809* (2013.01); *C07K 1/18* (2013.01); *C07K 1/22* (2013.01); *C07K 16/241* (2013.01); *G01N 30/56* (2013.01); *G01N 30/8665* (2013.01); *G01N 35/00623* (2013.01); *C07K 2317/24* (2013.01); *C07K 2317/31* (2013.01); *C07K 2317/565* (2013.01); *G01N 2030/562* (2013.01)

(58) Field of Classification Search
CPC ...... B01D 15/08; B01D 15/36; B01D 15/361; B01D 15/362; B01D 15/363; B01D 15/364; C07K 1/22; C07K 1/18; C07K 1/16; G01N 30/56
See application file for complete search history.

(56) References Cited

U.S. PATENT DOCUMENTS

| | | | |
|---|---|---|---|
| 894,395 | A | 7/1908 | Reid |
| 4,399,216 | A | 8/1983 | Axel |
| 4,634,665 | A | 1/1987 | Axel |
| 4,656,134 | A | 4/1987 | Ringold |
| 4,956,288 | A | 9/1990 | Barsoum |
| 5,122,464 | A | 6/1992 | Wilson |
| 5,149,636 | A | 9/1992 | Axel |

(Continued)

FOREIGN PATENT DOCUMENTS

| | | |
|---|---|---|
| JP | 2013502575 | 1/2013 |
| JP | 2016532881 | 10/2016 |

(Continued)

OTHER PUBLICATIONS

US 5,733,746 A, 03/1998, Treco (withdrawn)
Alt, et al., "Selective Multiplication of Dihydrofolate Reductase Genes in Methotrexate-resistant Variants of Cultured Murine Cells", Journal of Biological Chemistry, vol. 253 (1978), pp. 1357-1370.

(Continued)

*Primary Examiner* — Ryan B Huang
(74) *Attorney, Agent, or Firm* — Riverside Law LLP

(57) ABSTRACT

The present disclosure is directed to a method of operating a chromatography column in methods of manufacture for producing anti-IL-12/IL-23p40 antibodies, e.g., the anti-IL-12/IL-23p40 antibody STELARA® (ustekinumab), specific pharmaceutical compositions of the antibodies, and antigen binding fragments thereof. This method involves collecting column outlet signal and accumulated flow parameters at two or more intervals of at least one mobile phase transition front during operation of the chromatography column comprising column packing. A model gamma cumulative distribution curve is determined based on the collected column outlet signal and accumulated flow parameters for the at least one mobile phase transition front. The height equivalent theoretical plate (HETP) value is calculated for the at least one mobile phase transition front using parameters of the model gamma cumulative distribution curve and the quality of the chromatography column packing is assessed based on the calculated HETP value. If during routine column monitoring, an adverse trend in HETP is observed or the control limits are exceeded, the eluate product quality, column process performance, and/or impurity removal data should be evaluated to ensure product quality for the identified batch. Should any of the product quality or column performance fail the criteria set, appropriate corrective action, such as conditioning, repacking or replacing the column, and qualification should be performed prior to release for further use.

13 Claims, 32 Drawing Sheets
Specification includes a Sequence Listing.

(56) References Cited

U.S. PATENT DOCUMENTS

| | | | |
|---|---|---|---|
| 5,168,062 | A | 12/1992 | Stinski |
| 5,179,017 | A | 1/1993 | Axel |
| 5,266,491 | A | 11/1993 | Nagata |
| 5,385,839 | A | 1/1995 | Stinski |
| 5,410,928 | A | 5/1995 | Bakermans |
| 5,580,734 | A | 12/1996 | Treco |
| 5,641,670 | A | 6/1997 | Treco |
| 5,733,761 | A | 3/1998 | Treco |
| 5,770,359 | A | 6/1998 | Wilson |
| 5,827,739 | A | 10/1998 | Wilson |
| 6,171,825 | B1 | 1/2001 | Chan |
| 6,936,441 | B2 | 8/2005 | Reiter |
| 8,410,928 | B2 | 4/2013 | Ganguly |
| 8,895,709 | B2 | 11/2014 | Hickman |
| 9,047,438 | B2 | 6/2015 | Belousov |
| 9,518,082 | B2 | 12/2016 | Allison |
| 2007/0021277 | A1 | 1/2007 | Kuo |
| 2007/0215548 | A1 | 9/2007 | Zhou |
| 2007/0292442 | A1 | 12/2007 | Wan |
| 2008/0000904 | A1 | 1/2008 | Vovan |
| 2009/0252749 | A1 | 10/2009 | Leister |
| 2010/0100336 | A1 | 4/2010 | Wright |
| 2011/0147312 | A1 | 6/2011 | Cunnien |
| 2012/0271556 | A1 | 10/2012 | Szacherski |
| 2012/0282654 | A1 | 11/2012 | Yao |
| 2013/0281672 | A1 | 10/2013 | Belousov |
| 2013/0338344 | A1 | 12/2013 | Ramasubramanyan |
| 2014/0288272 | A1 | 9/2014 | Allison |
| 2017/0052159 | A1 | 2/2017 | Harant |
| 2017/0247444 | A1 | 8/2017 | Hedrick |
| 2018/0113101 | A1* | 4/2018 | Mao ................... G01N 30/8617 |

FOREIGN PATENT DOCUMENTS

| | | |
|---|---|---|
| WO | 2007077217 | 7/2007 |
| WO | 2007117490 A2 | 10/2007 |
| WO | 2009094203 A2 | 7/2009 |
| WO | 2010019814 | 2/2010 |
| WO | 2018024770 A1 | 2/2018 |

OTHER PUBLICATIONS

Bork, et al., "Online Integrity monitoring in the Protein A step of mAb Production Processes-increasing reliability and process robustness", Biotechnology Progress, vol. 30, No. 2, pp. 383-390, (Jan. 2014).

Boshart, et al., "A Very Strong Enhancer Is Located Upstream of an Immediate Early Gene of Human Cytomegalovirus", Cell, vol. 41 (1985), pp. 521-530.

Cullen, et al., "Functional Analysis of the Transcription Control Region Located Within the Avian Retroviral Long Terminal Repeat", Molecular and Cellular Biology, vol. 5 (1985), pp. 438-447.

Dolinar, et al., "A Guide to Follow-on Biologics and Biosimilars With a Focus on Insulin." Endocrine Practice, vol. 24, No. 2, pp. 195-204, (Feb. 2018).

Gossen, and H. Bujard, "Tight control of gene expression in mammalian cells by tetracycline-responsive promotoers", Proc. Natl. Acad. Sci. USA, vol. 89 (1992), pp. 5547-5551.

Gritti, et al., "The rationale for the optimum efficiency of columns packed with new 1.9 pm fully porous Titan-C18 particles—A detailed investigation of the intra-particle diffusivity", Journal of Chromatography A., vol. 1355, pp. 164-178, (Jun. 2014).

Jayapal et al., "Recombinant protein therapeutics from CHO cells-20 years and counting", Chemical Engineering Progress, vol. 103 (2007), pp. 40-47.

Kunert et al. Advances in recombinant antibody manufacturing : Appl. Micorbiol. Biotechnol. 100:3451-3461, 2016.

Larson et al., "Use of Process Data to Assess Chromatographic Performance in Production-Scale Protein Purification 10 Columns,", Biotechnol. Prog., vol. 19, pp. 485-492 (2003).

M. J. Page and M. A. Sydenham, "High Level Expression of the Humanized Monoclonal Antibody Campath-1H in Chinese Hamster Ovary Cells", Biotechnology, vol. 9 (1991), pp. 64-68.

Sprague, et al., "Expression of a Recombinant DNA Gene Coding for the Vesiclar Stomatitis Virus Nucleocapsid Protein", Journal of Virology, vol. 45 (1983), pp. 773-781.

Van Deemter, et al,, "Longitudinal Diffusion and Resistance to Mass Transfer as Causes of Nonideality in Chromatography,", Chem. Engng. Sci. vol. 5, pp. 271-289, (1956).

Vostokov et al., 2009, "Statistical criteria for the efficiency of chromatographic separation of substances by distributive hplc", 2:102-106.

* cited by examiner

SYSTEM FOR CHROMATOGRAPHY COLUMN QUALIFICATION IN MANUFACTURING METHODS FOR PRODUCING ANTI-IL12/IL23 ANTIBODY COMPOSITIONS

CROSS REFERENCE TO RELATED APPLICATION

This application is a continuation of U.S. patent application Ser. No. 16/389,114, filed Apr. 19, 2019, which claims priority to U.S. Provisional Application No. 62/660,340, filed Apr. 20, 2018, each of which is incorporated herein by reference in its entirety.

FIELD OF THE INVENTION

The present invention relates to a method of chromatography column qualification in methods of manufacture for producing anti-IL-12/IL-23p40 antibodies, e.g., the anti-IL-12/IL-23p40 antibody STELARA® (ustekinumab), specific pharmaceutical compositions of the antibodies, and antigen binding fragments thereof.

REFERENCE TO SEQUENCE LISTING SUBMITTED ELECTRONICALLY

This application contains a sequence listing, which is submitted electronically via EFS-Web as an ASCII formatted sequence listing with a file name "206389_0029_01US SequenceListing", creation date of Jul. 1, 2021 and having a size of 13 kb. Except for changes in the file name, this sequence listing is identical to the sequence listing with a file name "JBI6082USNP1 Sequences", creation date of Apr. 17, 2019 and having a size of 14 kb. The sequence listing submitted via EFS-Web is part of the specification and is herein incorporated by reference in its entirety.

BACKGROUND OF THE INVENTION

Column chromatography is an important technique used in purification processes to produce therapeutic proteins. The performance of columns must be maintained as the process is scaled-up from the bench top to manufacturing plants and throughout column lifetimes. Difficulties in column evaluation procedures, potential changes to the integrity of packed beds, and logistics can arise as the column diameter, equipment, and buffer consumption increases to scale up the process.

A current method for chromatography column qualification calculates Height Equivalent to Theoretical Plates (HETP), a measure of dispersion following a pulse injection, by estimating the mean from the peak maximum and the standard deviation from the width of the peak at half height. The primary limitation of this method is that it does not provide an accurate measure of dispersion (i.e., HETP) when the peak shape deviates from a Gaussian distribution. In order to compensate for the lack of sensitivity, a second measurement, Asymmetry, is utilized to assess peak skewness. This measure compares the leading and tailing peak width at 10% of the maximum peak height. The limitations of this approach result in a lack of sensitivity to changes in column performance, and often results in the repacking or conditioning of a column, while column performance is actually acceptable. Other strategies for column qualification have been reported. These strategies include using Gaussian or non-Gaussian distributions to model in process transitions (see e.g., Larson, et al., "Use of Process Data to Assess Chromatographic Performance in Production-Scale Protein Purification Columns," *Biotechnol. Prog.* 19:485-492 (2003) and U.S. Pat. No. 9,047,438 to Belousov et al., and U.S. Pat. No. 8,410,928 to Ganguly). The Gaussian approaches have the same limitations in sensitivity as noted supra for the injection method and the reported non-Gaussian approaches require complex calculations.

An improved qualification procedure with greater sensitivity and more rationally defined limits is needed to monitor changes in chromatography column performance during repeated operation and evaluate the effectiveness for which the column will perform over its lifetime. The present invention is directed at overcoming this deficiency in the art.

SUMMARY OF THE INVENTION

The embodiments of the invention are defined, respectively, by the independent and dependent claims appended hereto, which for the sake of brevity are incorporated by reference herein. Other embodiments, features, and advantages of the various aspects of the invention are apparent from the detailed description below taken in conjunction with the appended drawing figures.

In certain embodiments, the present invention provides a method of operating a chromatography column in methods of manufacture for producing anti-IL-12/IL-23p40 antibodies, specific pharmaceutical compositions of the antibodies, and antigen binding fragments thereof, wherein the anti-IL-12/IL-23p40 antibodies comprise amino acid sequences selected from the group consisting of: (i) a heavy chain (HC) comprising the amino acid sequence of SEQ ID NO:10 and a light chain (LC) comprising the amino acid sequence of SEQ ID NO:11; (ii) a heavy chain variable domain amino acid sequence of SEQ ID NO:7 and a light chain variable domain amino acid sequence of SEQ ID NO:8; and (iii) heavy chain CDR amino acid sequences of SEQ ID NO:1, SEQ ID NO:2, and SEQ ID NO:3, and light chain CDR amino acid sequences of SEQ ID NO:4, SEQ ID NO:5, and SEQ ID NO:6. This method involves collecting column outlet signal and accumulated flow parameters at two or more intervals of at least one mobile phase transition front during a first operation of the chromatography column comprising column packing. This method further involves determining a model gamma cumulative distribution curve based on the collected column outlet signal and accumulated flow parameters for the at least one mobile phase transition front using Formula Ia for a rising transition front or Formula Ib for a falling transition front, $$C = 1 - \frac{1}{\Gamma(k)} \gamma\left(k, \frac{V - V_i}{\theta}\right) \quad \text{Formula Ia}$$

or $$C = \frac{1}{\Gamma(k)} \gamma\left(k, \frac{V - V_i}{\theta}\right) \quad \text{Formula Ib}$$

wherein C is column outlet signal for a given V, V is the accumulated flow divided by the column volume, and k, θ, and $V_i$ are the shape, scale and offset parameters used to define the curve. The height equivalent theoretical plate (HETP) value is calculated for the at least one mobile phase transition front using Formula II and the model gamma cumulative distribution curve parameters of k, θ, and $$HEPT = \frac{\sigma^2}{\mu^2} L \qquad \text{Formula II}$$

where $\mu = k\theta + V_i$ $\sigma = \sqrt{k\theta^2}$, and $L$ = column length The quality of the chromatography column packing is assessed based on the calculated HETP value. Based on this assessment, the chromatography column is reused, conditioned, replaced, or repacked.

A new method for assessing column integrity, referred to herein as Gamma Distribution Transition Analysis (GDTA), has been developed. The new method uses a mathematical model to fit a curve through mobile phase transition front data that is generated during regular process steps of column operation. Model curve parameters are then utilized to calculate the dispersion across the column bed as a measure of column quality. Mobile phase transition fronts arise from discrete steps within the chromatography purification process where process buffers/wash solutions with different properties, such as conductivity, pH, and/or buffer components are used. The method can generally be applied to any one or more mobile phase transition fronts generated during normal column processing.

A primary advantage of the GDTA method is that it provides a more sensitive gauge of dispersion across the column bed than the Gaussian HETP estimation method. By using GDTA, it is no longer necessary to measure asymmetry, as the GDTA model correctly measures dispersion from the curve fit. Additionally, the use of the gamma distribution function facilitates ease of analysis of frontal transitions when compared to alternative non-gaussian methods previously reported. The use of mobile phase transitions already present in a chromatography process avoids the need for extra offline processing steps. Furthermore, in many cases, historical data allows for establishment of historical ranges of column efficiency prior to implementation. Finally, the GDTA method can be automated to ensure consistent application.

In certain embodiments, the present invention provides a method of operating a chromatography column in methods of manufacture for producing anti-IL-12/IL-23p40 antibodies, specific pharmaceutical compositions of the antibodies, and antigen binding fragments thereof, wherein the anti-IL-12/IL-23p40 antibodies comprise amino acid sequences selected from the group consisting of: (i) a heavy chain (HC) comprising the amino acid sequence of SEQ ID NO:10 and a light chain (LC) comprising the amino acid sequence of SEQ ID NO:11; (ii) a heavy chain variable domain amino acid sequence of SEQ ID NO:7 and a light chain variable domain amino acid sequence of SEQ ID NO:8; and (iii) heavy chain CDR amino acid sequences of SEQ ID NO:1, SEQ ID NO:2, and SEQ ID NO:3, and light chain CDR amino acid sequences of SEQ ID NO:4, SEQ ID NO:5, and SEQ ID NO:6, said method comprising:

collecting column outlet signal and accumulated flow parameters at two or more intervals of at least one mobile phase transition front during a first operation of the chromatography column comprising column packing;

determining a model gamma cumulative distribution curve based on the collected column outlet signal and accumulated flow parameters for the at least one mobile phase transition front using Formula Ia for a rising transition front or Formula Ib for a falling transition front, $$C = 1 - \frac{1}{\Gamma(k)} \gamma\left(k, \frac{V - V_i}{\theta}\right) \qquad \text{Formula Ia}$$

or $$C = \frac{1}{\Gamma(k)} \gamma\left(k, \frac{V - V_i}{\theta}\right) \qquad \text{Formula Ib}$$

wherein C is column outlet signal for a given V, V is the accumulated flow divided by the column volume, and k, θ, and $V_i$ are the shape, scale and offset parameters used to define the curve;

calculating a height equivalent theoretical plate (HETP) value for the at least one mobile phase transition front using Formula II and the model gamma cumulative distribution curve parameters of k, θ, and $V_i$, $$HEPT = \frac{\sigma^2}{\mu^2} L \qquad \text{Formula II}$$

wherein $\mu = k\theta + V_i$ $\sigma = \sqrt{k\theta^2}$ $L$ = column length;

and assessing quality of the chromatography column packing based on said calculated HETP value.

In certain embodiments, the present invention provides a method further comprising:

conditioning, replacing, or repacking the chromatography column based on said assessing.

In certain embodiments, the present invention provides a method further comprising:

collecting column outlet signal and accumulated flow parameters at two or more intervals of a corresponding mobile phase transition front during one or more subsequent uses of the chromatography column packing;

performing said determining and said calculating using the column outlet signal and accumulated flow parameters collected during each of the one or more subsequent uses of the chromatography column packing;

determining an HETP value of the chromatography column packing during each of said one or more subsequent uses based on said performing;

compiling a trend of the determined HETP values of the chromatography column packing of the two or more subsequent uses; and identifying a change in the quality of the chromatography column packing based on said compiled trend, wherein said conditioning, replacing or repacking the chromatography column is based on said identifying.

In certain embodiments, the present invention provides a method, wherein an increase in the HETP value of the chromatography column packing in the one or more subsequent uses of said column packing as compared to the HETP value of the chromatography column packing in one or more earlier uses of said column packing identifies a decrease in quality of the chromatography column packing.

In certain embodiments, the present invention provides a method, wherein column outlet signal and accumulated flow parameters of two or more different mobile phase transition fronts during said first operation of the column packing are collected, said method comprising:

performing said determining and calculating using the column outlet signal and accumulated flow parameters collected for each of the two or more different mobile phase transition fronts independently to calculate an HETP value for each of the two of more different mobile phase transition fronts;

assessing the quality of the chromatography column packing based on the two or more calculated HETP values, whereby said conditioning, replacing or repacking the chromatography column is based on said assessing.

In certain embodiments, the present invention provides a method, wherein the chromatography column is selected from the group consisting of: a Protein A affinity chromatography column, a cation exchange chromatography column, and an anion exchange chromatography column.

In certain embodiments, the present invention provides a method, wherein the Protein A affinity chromatography column comprises a MabSelect™ Protein A affinity chromatography column, the cation exchange chromatography column comprises a UNOsphere S™ cation exchange chromatography column or an SP Sepharose XL cation exchange chromatography column, and the anion exchange chromatography column comprises a Q Sepharose™ XL anion exchange chromatography column.

In certain embodiments, the present invention provides a method, wherein the mobile phase transition front in the Protein A affinity chromatography column is generated from one or more fronts selected from the group consisting of: a wash front generated during purification of the anti-IL-12/IL-23p40 antibodies, a front generated during elution of the anti-IL-12/IL-23p40 antibodies, a front generated during sanitization of the column with Guanidine HCl, a front generated during post-sanitization rinsing of the column with 0.1 M Sodium Citrate, pH 3.5.

In certain embodiments, the present invention provides a method, wherein the mobile phase transition front in the cation exchange chromatography column is generated from one or more fronts selected from the group consisting of: a front generated during loading of solvent/detergent (S/D) treated material comprising the anti-IL-12/IL-23p40 antibodies, a front generated during elution of the anti-IL-12/IL-23p40 antibodies, and a front generated during a column strip.

In certain embodiments, the present invention provides a method, wherein the mobile phase transition front in the anion exchange chromatography column is generated from one or more fronts selected from the group consisting of: a front generated during cleaning of the column with Sodium Hydroxide and a front generated during a column strip.

BRIEF DESCRIPTION OF THE DRAWINGS

FIG. 1A is a graph showing an exemplary gamma distribution transition analysis curve fit to mobile phase transition data. FIG. 1B is a graph showing an exemplary gamma distribution transition analysis curve fit to mobile phase transition data with parameters from that curve used to calculate the height equivalent theoretical plate (HETP) as a measure of column efficiency.

DETAILED DESCRIPTION OF THE INVENTION

Figure 1A:
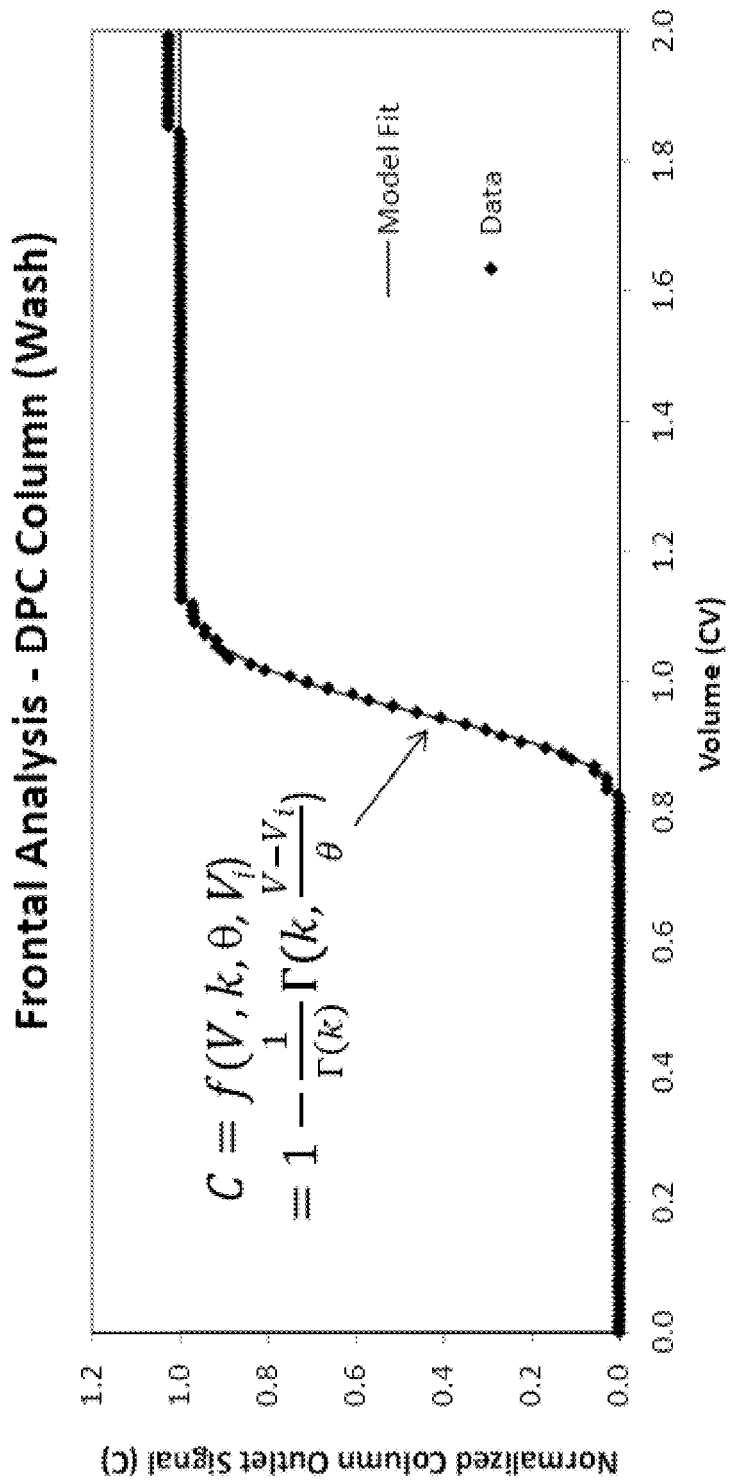
FIGS. 1A-1B show graphs of exemplary gamma distribution transition analysis curve fits.

The present disclosure relates to an improved qualification procedure for monitoring changes in packed chromatography column beds during repeated operation of chromatography columns in methods of manufacture for producing anti-IL-12/IL-23p40 antibodies, e.g., the anti-IL-12/IL-23p40 antibody STELARA® (ustekinumab), and specific pharmaceutical compositions of the antibody. This method, independent of scale, provides a practical means to evaluate the effectiveness for which the column will perform throughout the column lifetime.

Chromatography column separation efficiency is often characterized using the theoretical plate model of chromatography. Using this approach, the chromatography column is perceived as consisting of a number of stages or theoretical plates. Each plate is the distance over which the sample components achieve equilibrium between the mobile and stationary phases (see Van Deemter, Zuiderweg and Klinkenberg, "Longitudinal Diffusion and Resistance to Mass Transfer as Causes of Nonideality in Chromatography," *Chem. Engng. Sci.* 5: 271-289 (1956), which is hereby incorporated by reference in its entirety). Column efficiency is measured by the number of theoretical plates in the column $N_p$, where more plates in the column means more equilibrations, less dispersion of chromatographic bands, narrower peaks, and better-quality separation. The higher the number of plates in a given column, the lower the plate height. Accordingly, column efficiency can also be measured by calculating plate height, which is referred to as "height equivalent to a theoretical plate" or HETP. Using this approach, the smaller the HETP value the higher the efficiency of column separation.

HETP is calculated by dividing by the length of chromatography column L by the number of theoretic plates $N_p$.

$$HETP = L/N_p$$

The number of theoretical plates that a column possesses has historically been determined by examining a chromatographic peak after a pulse injection using the following formula:

$$N_p = 5.54 \left( \frac{t_R}{w_{1/2}} \right)^2$$

where $t_R$ is the retention time and $w_{1/2}$ is the peak width at half height. However, this approach does not provide an accurate measure of column efficiency when the peak shape used to calculate $N_p$ deviates from a Gaussian distribution. In order to compensate for this lack of sensitivity, a second measurement—Asymmetry—is used to assess peak skewness. This measure compares the leading and tailing peak width at 10% of the maximum peak height. As discussed supra, this model lacks sensitivity to detect changes in column performance.

The method described herein provides an alternative and more accurate measure of HETP that is based on gamma distribution over one or more mobile phase transition fronts that occur during routine chromatography column operation. Thus, the present disclosure is directed to a method of operating a chromatography column. This method involves collecting column outlet signal and accumulated flow parameters at two or more intervals of at least one mobile phase transition front during a first operation of the chromatography column containing column packing. This method further involves determining a model gamma cumulative distribution curve based on the collected column outlet signal and accumulated flow parameters for the at least one mobile phase transition front using Formula Ia for a rising transition front or Formula Ib for a falling transition front.

$$C = 1 - \frac{1}{\Gamma(k)} \gamma\left(k, \frac{V - V_i}{\theta}\right) \qquad \text{Formula Ia}$$

or $$C = \frac{1}{\Gamma(k)} \gamma\left(k, \frac{V - V_i}{\theta}\right) \qquad \text{Formula Ib}$$

In reference to Formula Ia and Formula Ib, C is column outlet signal for a given V, V is the accumulated flow divided by the column volume, and k, θ, and $V_i$ are the shape, scale and offset parameters used to define the curve. The height equivalent theoretical plate (HETP) value is calculated for the at least one mobile phase transition front using Formula II and the model gamma cumulative distribution curve parameters of k, θ, and $V_i$, $$HEPT = \frac{\sigma^2}{\mu^2} L \qquad \text{Formula II}$$

where $\mu = k\theta + V_i$ $\sigma = \sqrt{k\theta^2}$, and

L = column length.

The quality of the chromatography column packing is assessed based on the calculated HETP value. Based on the assessment of column quality, the chromatography column is determined to be acceptable for subsequent use, or otherwise must be conditioned, replaced, or repacked.

The method of column qualification disclosed herein can be applied to any chromatography column. Exemplary chromatography columns include, without limitation, those used for liquid chromatography, high-performance liquid chromatography (HPLC), ion exchange chromatography, affinity chromatography, molecular exclusion, super critical fluid chromatography, gas chromatography, size exclusion chromatography, reverse phased chromatography, two-dimensional chromatography, fast protein (FPLC) chromatography, countercurrent chromatography, chiral chromatography, aqueous normal phase (ANP), mixed mode chromatography, and pseudo-affinity chromatography. Exemplary column packing material includes, without limitation, affinity chromatography packing material (e.g., protein A or protein G affinity chromatography packing material), ion exchange chromatography packing material (e.g., cation exchange (carboxymethyl resins), anion exchange (amino ethyl resins), and mixed-mode exchange chromatography packing material), adsorption chromatography packing material (e.g. silica gel or alumina packing material), hydrophobic interaction chromatography packing material (e.g. phenyl-sepharose, aza-arenophilic resins, or m-aminophenylboronic acid packing materials), metal chelate affinity chromatography packing material (e.g., Ni(II)- and Cu(II)-affinity material), size exclusion chromatography packing material (e.g., gel electrophoresis or capillary electrophoresis packing material), or molecular exclusion chromatography packing material (e.g., polystyrene).

The method described herein can be applied during routine chromatography column operation, e.g., during isolation, purification, or identification of chemical or biological entities in a sample. Such compounds may include, for example but without limitation, proteins (e.g., antibodies and fragments thereof), nucleic acids, carbohydrates, lipids, organic small molecules, inorganic small molecules, viruses, liposomes, and hybrids or variant forms of any such compounds.

In contrast to previous chromatography column qualification methods, which require the column be taken offline for testing, e.g., the pulse injection method, the method as described herein is carried out during routine column operation. The present method takes advantage of mobile phase process transitions involving process buffers and solutions having different properties, which occur during a routine column purification process.

In accordance with the method of the present invention, the "mobile phase" is the liquid phase in column chromatography that surrounds and moves through the stationary chromatography material of the chromatography column packing. During chromatography column operation, the composition and properties of the mobile phase often change with each process step, e.g., equilibration, washes, etc. Changes in the properties of the mobile phase can be detected and measured in the eluate, i.e., the mobile phase that is eluted from the column after passing through the stationary phase. As used herein, the "column outlet signal" is the signal of a physical or chemical property of the eluate from the mobile phase that is detected as the eluate elutes off the column. The physical or chemical property providing the column outlet signal can be any property, such as pH, conductivity, light absorption, fluorescence, charge, salt concentration, polarimetry, refractive index, electrochemical response, mass-to-charge ratio, etc. that can be measured using any typical chromatography detector. Chromatography detectors suitable for measuring the column outlet signal include, without limitation, a mass spectrometer, infrared spectrometer, visible spectrometer, ultraviolet spectrometer, Fourier transform infrared spectrometer, flame ionization detector, low angle laser light scattering detector, diode array detector, fluorescence spectrometer, pH detector, conductivity detector, electrochemical detector, and refractive index detector.

The column outlet signal is collected from the eluate. In addition, to collecting the column outlet signal, the "accumulated flow" is also collected. The "accumulated flow" is the total volume of fluid eluted from the column over time. This value is divided by the volume of the column to be expressed in units of column volumes.

A transition front is generated by the change in column outlet signal over the accumulated flow. A transition front arises from the sequential application of different mobile phases having one or more different properties (e.g., conductivity, pH, etc.) to a column. In accordance with the method described herein, the column outlet signal over the transition front can be normalized to have a maximum value of 1 and a minimum value of 0. As referred to herein, a "falling transition front" is a mobile phase transition where the starting mobile phase has a column outlet signal, e.g., conductivity, that is higher than the column outlet signal of the sequentially introduced mobile phase.

A "rising transition front" as used here is a mobile phase transition where the starting mobile phase has a column outlet signal, e.g., conductivity, that is lower than the column outlet signal of the sequentially introduced mobile phase.

A transition front is created by adding a first mobile phase to the chromatography column containing column packing to be qualified during the course of column operation. At some time after the addition of the first mobile phase, e.g., as the first mobile phase begins to elute, a second mobile phase having a different detectable column outlet signal compared to the first mobile phase is added to the chromatography column containing the column packing. The transition front is detected by collecting column outlet signal and accumulated flow parameters at two or more intervals of the mobile phase as it transitions between the first and second mobile phases.

In one embodiment, the column outlet signal for the first and second mobile phases differ in signal by an amount exceeding the signal noise. In one embodiment, the difference in column outlet signal between the first and second mobile phases is 5% above the background signal noise. In another embodiment, the difference in column outlet signal between the first and second mobile phases is at least 10% above the background signal noise. In another embodiment, the difference in column outlet signal between the first and second mobile phases is at least 15% above the background signal noise.

In one embodiment, the column outlet signal detected over the transition front is conductivity. In this embodiment, the column outlet signal between the first and second mobile phases preferably differs by at least 1 µS/cm, by at least 10 µS/cm, by at least 100 µS/cm, by at least 1 mS/cm, or by greater than 1 mS/cm.

In another embodiment, the column outlet signal detected over the transition front is pH. In this embodiment, the column outlet signal between the first and second mobile phases preferably differs by at least 0.05 pH units, by at least 0.1 pH units, by at least 1 pH units, by at least 2 pH units, or by greater than 2 pH units.

In another embodiment, the column outlet signal detected over the transition front is UV-Vis absorbance. In this embodiment, the column outlet signal between the first and second mobile phases preferably differs by at least 0.01 absorbance unit, by at least 0.1 absorbance unit, by at least 0.5 absorbance unit, by at least 0.8 absorbance unit, or by more than 0.8 absorbance unit.

In another embodiment, the column outlet signal detected over the transition front is infrared absorbance. In this embodiment, the column outlet signal between the first and second mobile phases preferably differs by at least 1 percent transmittance, by at least 10 percent transmittance, by at least 20 percent transmittance, by at least 30 percent transmittance, or by more than 30 percent transmittance.

In one embodiment, the mobile phase transition front is generated by a change from a mobile phase containing a denaturing agent to a mobile phase containing a non-denaturing agent. In another embodiment, the mobile phase transition front is generated by a change from a mobile phase containing a non-denaturing agent to a mobile phase containing a denaturing agent.

In another embodiment, the mobile phase transition front is generated by a change from an alkaline mobile phase condition to a neutral or more acidic mobile phase condition. Alternatively, the mobile phase transition front is generated by a change from an acidic mobile phase condition to a neutral or more alkaline mobile phase condition.

In another embodiment, the mobile phase transition front is generated by a change from organic solvent containing mobile phase to an aqueous mobile phase. Alternatively, the mobile phase transition front is generated by a change from an aqueous mobile phase to an organic solvent containing mobile phase.

The column outlet signal and accumulated flow parameters are collected at various intervals over the course of the mobile transition front. Preferably, column outlet signal and accumulated flow parameters are collected over the course of the entire mobile transition front, from the minimum column outlet signal to the maximum column outlet signal or vice versa. In one embodiment, the column outlet signal and accumulated flow parameters are collected at irregular intervals, e.g., collected when a change in the column outlet signal is detected. In another embodiment, the column outlet signal and accumulated flow parameters are collected at regular timed intervals over the course of the entire mobile transition front. For example, in one embodiment, the column outlet signal and accumulated flow parameters are collected at 1 second intervals over the course of the entire mobile transition front. In another embodiment, the column outlet signal and accumulated flow parameters are collected at 5, 10, 15, 20, 25, 30, 35, 40, 45, 50, 55, or 60 second intervals over the course of the mobile transition phase.

In one embodiment, the column outlet signal data is normalized as described supra by setting the maximum value to 1 and the minimum value to 0 over the period of analysis. Flow is also converted to column volumes to standardize for comparison of data between different column packings. Using this data, the gamma cumulative distribution function ("CDF") is used to generate a curve that best fits the collected data points. The gamma CDF is determined by three values: shape parameter k; scale parameter θ (theta); and offset parameter $V_i$ using the following Formula I:

$$C = f(V, k, \theta, Vi) \quad \text{Formula I}$$

In reference to Formula I, C is column outlet signal for a given V, V is the accumulated flow divided by the column volume. Formula Ia, which is derived from Formula I, is used determine the gamma distribution function value along a rising transition front.

$$C = 1 - \frac{1}{\Gamma(k)} \gamma\left(k, \frac{V - V_i}{\theta}\right) \quad \text{Formula Ia}$$

wherein

Γ is the upper incomplete gamma function, and

γ is the lower incomplete gamma function.

Alternatively, Formula Ib, which is also derived from Formula I, is used to determine the gamma distribution function value along a falling transition front.

$$C = \frac{1}{\Gamma(k)} \gamma\left(k, \frac{V - V_i}{\theta}\right) \quad \text{Formula Ib}$$

FIG. 1A is a graph plotting exemplary normalized column outlet signal and column volume data collected over a column transition front. Formula Ia was used to generate the curve fit to the data.

The best fit gamma CDF parameters are determined by manipulating the values of k, θ, and $V_i$ to find the parameters that produce a model curve with the least sum of squares deviation from the data. This curve is fitted through the data points from the entire transition front to generate the best fit model. The k, θ, and $V_i$ parameters from this curve are utilized to calculate the number of plates $N_p$ in the column or the plate height, i.e., HETP, as indicators of column efficiency.

The number of plates $N_p$ is calculated based on the mean μ and variance $\sigma^2$ of the model curve. The mean and variance are derived from the curve as follows:

Mean, $\mu = k\theta + V_i$

Variance, $\sigma^2 = k\theta^2$

The number of plates is calculated based on the mean and variance as follows:

Number of plates, $N_p = \mu^2/\sigma^2$

The HETP is calculated as described supra based on the length of the column L in centimeters divided by the number of plate $N_p$, as follows.

$$HETP = \frac{L}{N_P} = \frac{\sigma^2}{\mu^2} \cdot L = \frac{k\theta^2 L}{(k\theta + V_i)}$$

Figure 1B:
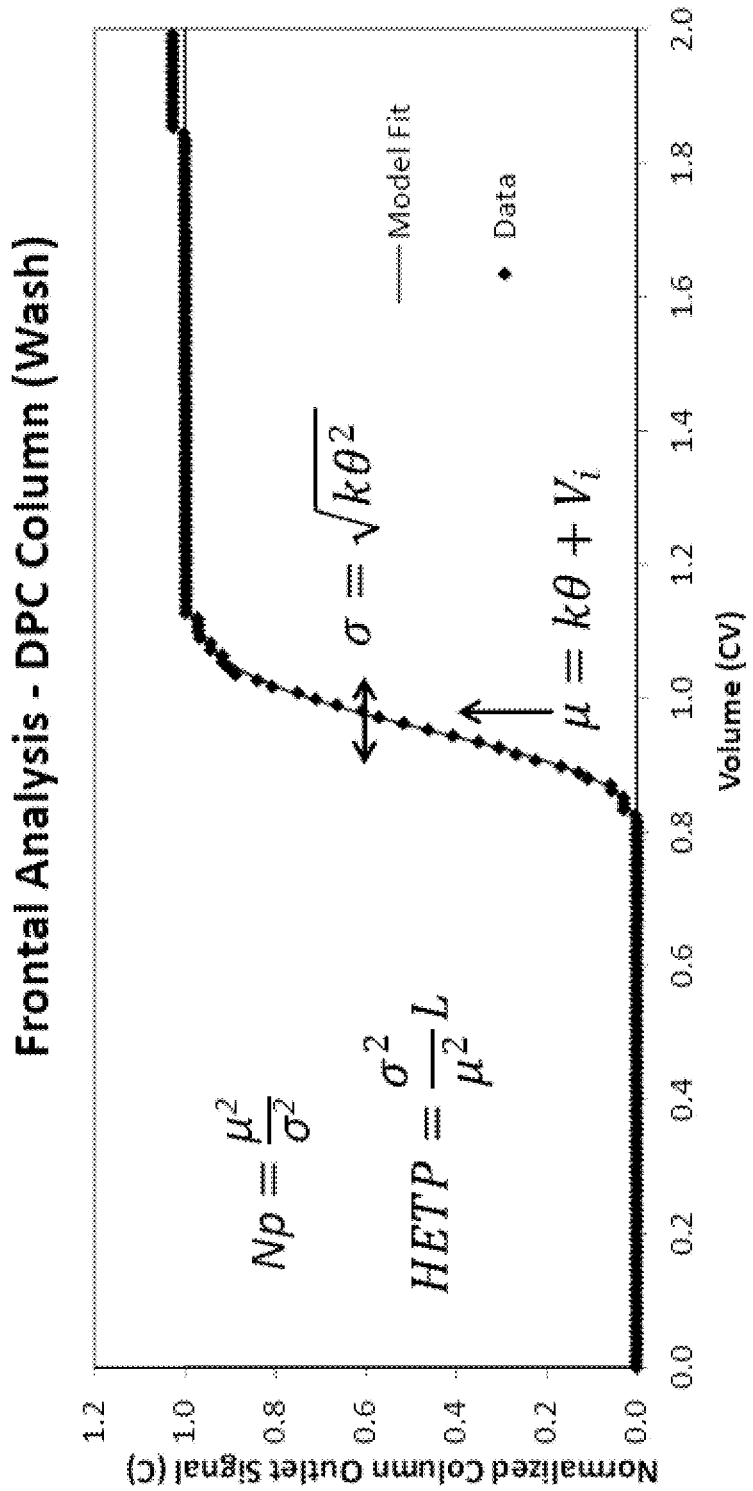

FIG. 1B shows the same graph as shown in FIG. 1A, with the mean μ and variance σ2 parameters defined.

To evaluate the model fit to the data calculated as described herein, the mean ($V_m$), sum of squares (SS), and mode can also be determined. SS is a direct measure of the deviation of the model curve from the process data upon which it is derived. The $V_m$ value is a measure of the center point of the transition in units of column volumes. This value should be close to one as it typically takes one column volume for a buffer transition. Mean is not typically affected by the shape of the front. Mean values are used to check the automatic calculations for errors. For example, a low value might indicate a data collection error and may require further investigation to confirm the result. The mode corresponds to the volume where the rate of change is greatest. This will be equal to the mean when the transition curve is symmetrical. Typically, the transitions are skewed, and the mode is lower than the mean.

In addition to HETP, other factors that can be calculated from the k (shape) parameter include skewness ($\gamma_1$), which is a measure related to asymmetry, and kurtosis ($\gamma_2$), which is a measure of the peak sharpness. These factors can be used to identify changes in column performance.

$$\gamma_1 = \frac{2}{\sqrt{k}}$$

$$\gamma_2 = \frac{6}{k}$$

In accordance with the method described herein, the column outlet signal and accumulated flow parameters are collected for the same mobile transition phase each time the column process is run on the column to calculate HETP from the gamma CDF. Historical data generated by columns used for the same process step and same scale can also be retrieved and utilized to calculate HETP. The HETP data is compiled to identify trends in the HETP values of corresponding transitions during historical or current operations to identify upper and lower control limits of the HETP value. The control limits are the high and low values of HETP that define the range of acceptable HETP values, i.e., HETP values that correspond to acceptable column efficiency. These upper and lower control limits can be set based on statistical evaluation. For example, in one embodiment the upper and lower control limits are set by calculating the mean +/−2, 3, or 4 standard deviations. In one embodiment, the upper and lower control limits are set by calculating the mean +/−3 standard deviations as described in the Examples herein. In another embodiment, the upper and lower control limits can be set by calculating the confidence interval from the historical data. In one embodiment, the upper and lower control limits are set by calculating the 95%, 96%, 97%, or 98% confidence interval from the historical data. In another embodiment, the upper and lower control limits are set by calculating the 99% confidence interval from the historical data.

The upper and lower control limits are utilized to identify changes in column efficiency over time and use of the column. Typically, any increase in HETP that exceeds the upper control limit may be indicative of a decrease in column efficiency. If during routine column monitoring, an adverse trend in HETP is observed or the control limits are exceeded, the eluate product quality, column process performance, and/or impurity removal data should be evaluated to ensure product quality for the identified batch. Should any of the product quality or column performance fail the criteria set, appropriate corrective action, such as conditioning, repacking or replacing the column, and qualification should be performed prior to release for further use. Methods of conditioning a chromatography column to redistribute the packed bed will vary depending on the column being employed, but are well understood to those of skill in the art.

The monitoring of column performance during column operation can be based on one, or more than one, transition phases that are routinely included in a purification protocol. Preferably, monitoring is based on HETP values calculated based on gamma CDF for two, or three, or more transition phases during a purification protocol.

As noted infra, calculating HETP using the GDTA method as described herein to determine column performance can be based on historical data collected from columns used for the same process step and same scale. Data generated from a qualified reduced scale model of the process step can also be used for the evaluation. This allows for the evaluation of the quality of the column's performance as compared to the qualification data.

Factors such as flow rate (Van Deemter effect), potential buffer interactions and extra column volume can impact the results of the GDTA method as described herein and should be assessed in setting the control limits for GDTA. Transition fronts included in the GDTA preferably meet certain criteria such as both mobile phase column outlet signal measurements are on scale, the column outlet signal measurement difference between mobile phases is above the background signal noise, and interaction between mobile phase and resin is consistent and reproducible.

Common column evaluation criteria used for release and monitoring during use shall be determined by evaluating historical data specific to equipment and resin type. Examples of routine product quality and process performance measurements that can be used to evaluate the relationship between column qualification results and performance are listed in Table 1. Routine quality and process performance measurements used for evaluation are not limited to those listed in Table 1, but the list is meant to be a guideline and should be based on the specific requirements of the project and process step being evaluated. Specifications and acceptance criteria for product quality and process performance are project specific and will be determined based on process requirements.

TABLE 1

Routine Quality and Step Performance Measures

| Parameter | Analytical Method |
|---|---|
| Pre-Elution Volume (CV) | |
| Elution Volume (CV) | |
| Step Yield | |
| Chromatographic Profile | Visual inspection |
| Eluate Concentration | A280 |
| Eluate Monomer | DW-SE-HPLC |
| Process Impurities | Various Assays |

The gamma distribution transition analysis method as described herein can be carried out in real-time during column operation. This method involves collecting, by a chromatography column qualification computing device, column outlet signal and accumulated flow parameters at two or more intervals of at least one mobile phase transition front during a first operation of the chromatography column comprising column packing; determining, by a chromatography column qualification computing device, a model gamma cumulative distribution curve based on the collected column outlet signal and accumulated flow parameters for the at least one mobile phase transition front using Formula Ia for a rising transition front or Formula Ib for a falling transition front.

$$C = 1 - \frac{1}{\Gamma(k)} \gamma\left(k, \frac{V - V_i}{\theta}\right) \quad \text{Formula Ia}$$

or $$C = \frac{1}{\Gamma(k)} \gamma\left(k, \frac{V - V_i}{\theta}\right) \quad \text{Formula Ib}$$

In reference to Formulas Ia and Ib, C is column outlet signal for a given V, V is the accumulated flow divided by the column volume, and k, θ, and $V_i$ are the shape, scale and offset parameters used to define the curve. This method further involves calculating, by a chromatography column qualification computing device, a height equivalent theoretical plate (HETP) value for the at least one mobile phase transition front using Formula II and the model gamma cumulative distribution curve parameters of k, θ, and $V_i$, $$HEPT = \frac{\sigma^2}{\mu^2} L \quad \text{Formula II}$$

wherein $\mu = k\theta + V_i$ $\sigma = \sqrt{k\theta^2}$

L = column length.

The method further involves assessing, using a chromatography column qualification computing device, quality of the chromatography column packing based on said calculated HETP value. Based on this assessment, the chromatography column operator can determine whether the chromatography column can be reused, or needs to be replaced, repacked, or conditioned prior to the next column operation.

Figure 2:
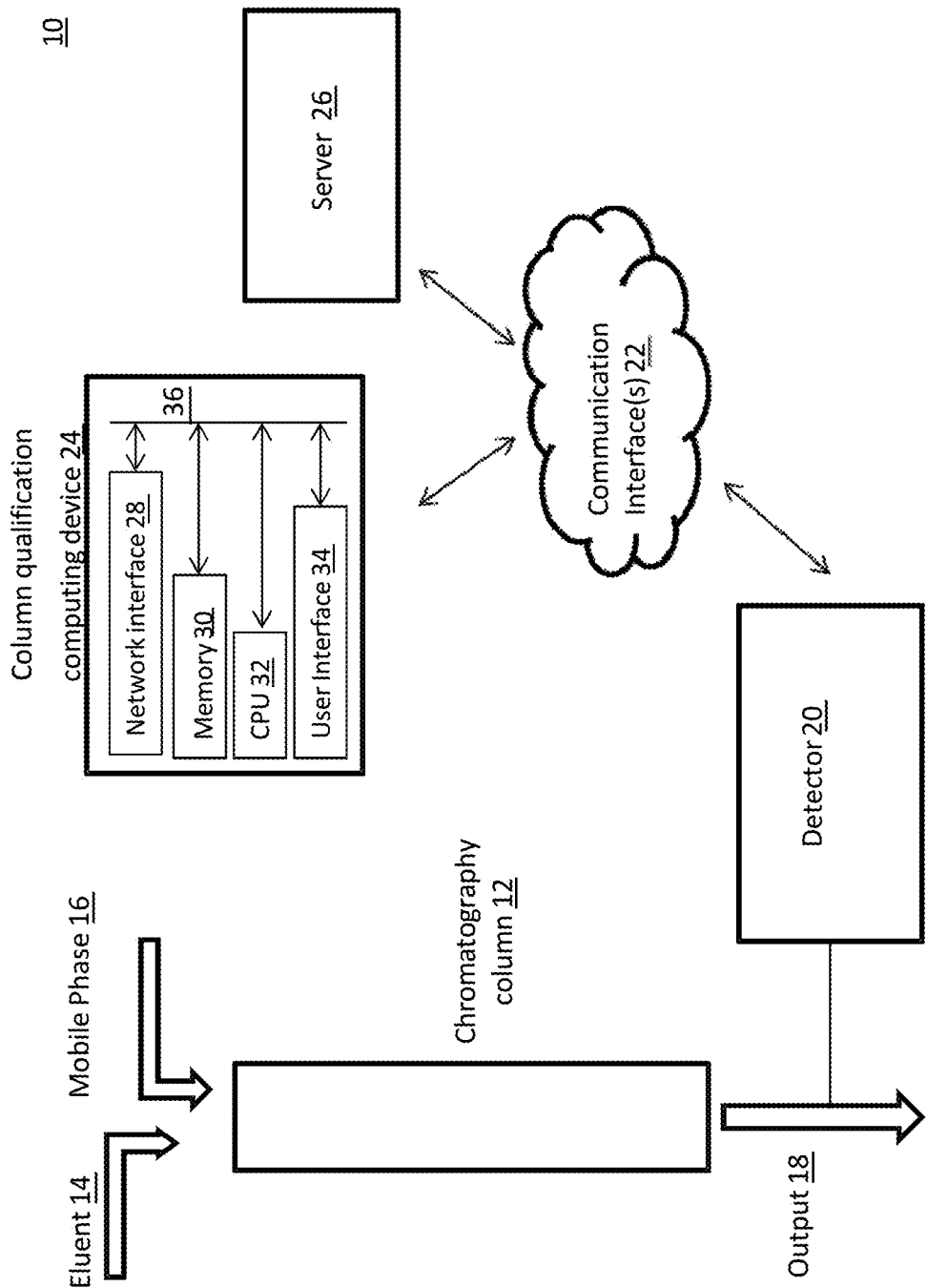
FIG. 2 is a diagram showing the chromatography column qualification system described herein.
Figure 3:
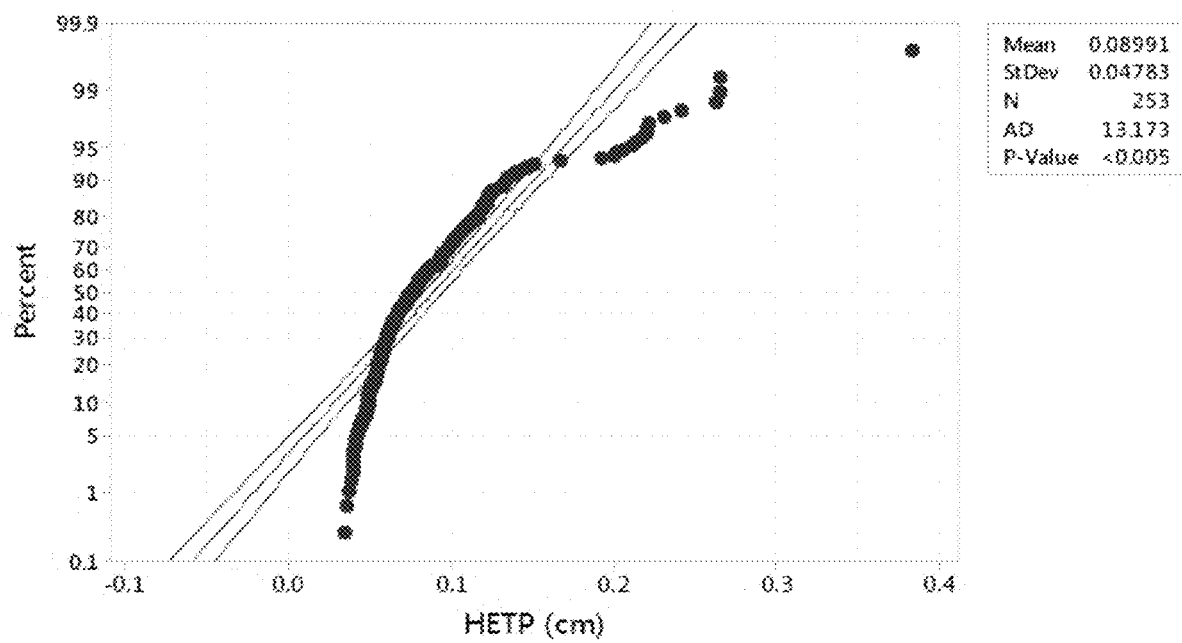
FIG. 3 is a probability plot of HETP for Protein A column equilibration front without transformation.
Figure 4:
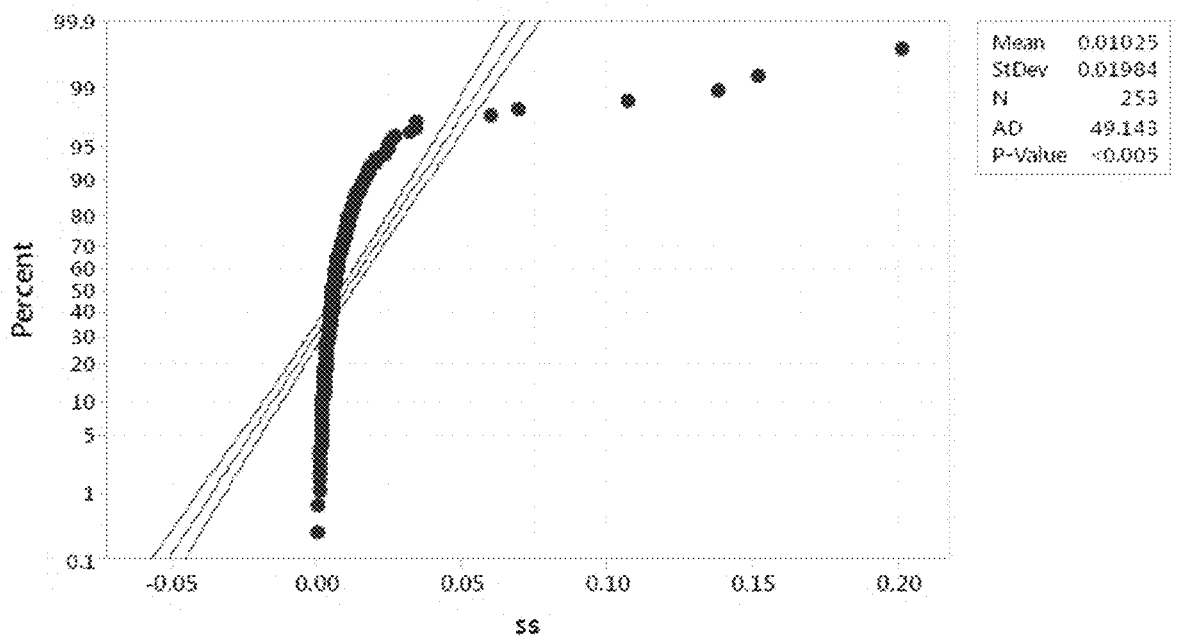
FIG. 4 is a probability plot of the sum of squares (SS) for Protein A column equilibration front without transformation.
Figure 5:
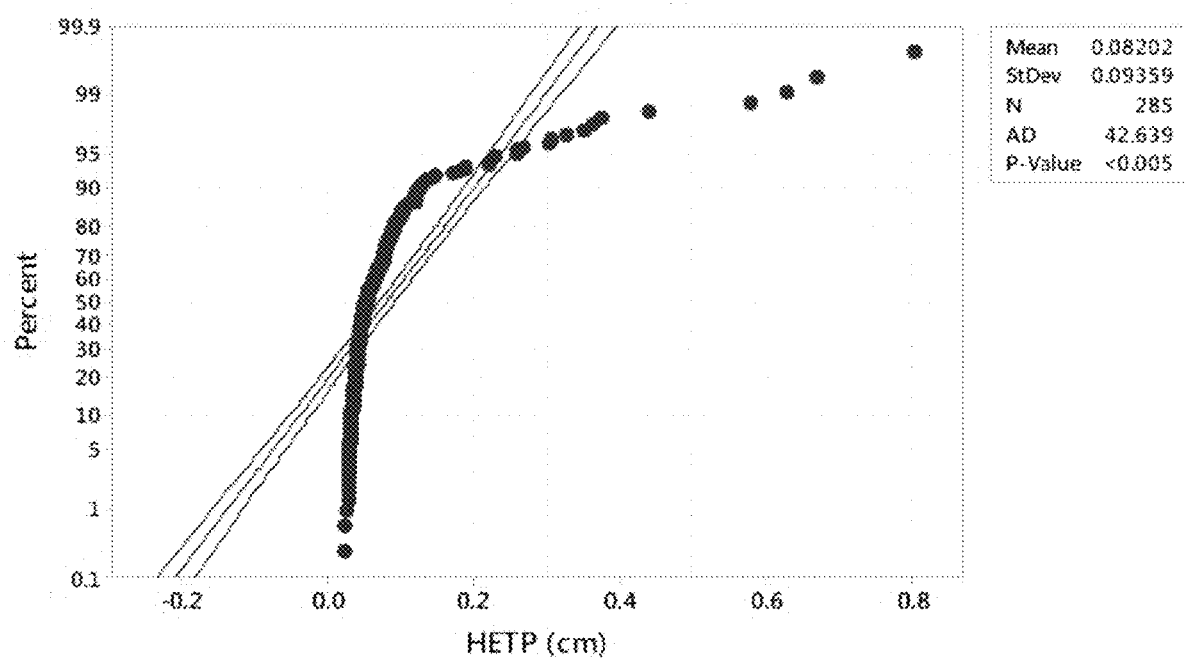
FIG. 5 is a probability plot of HETP for Protein A column wash front without transformation.
Figure 6:
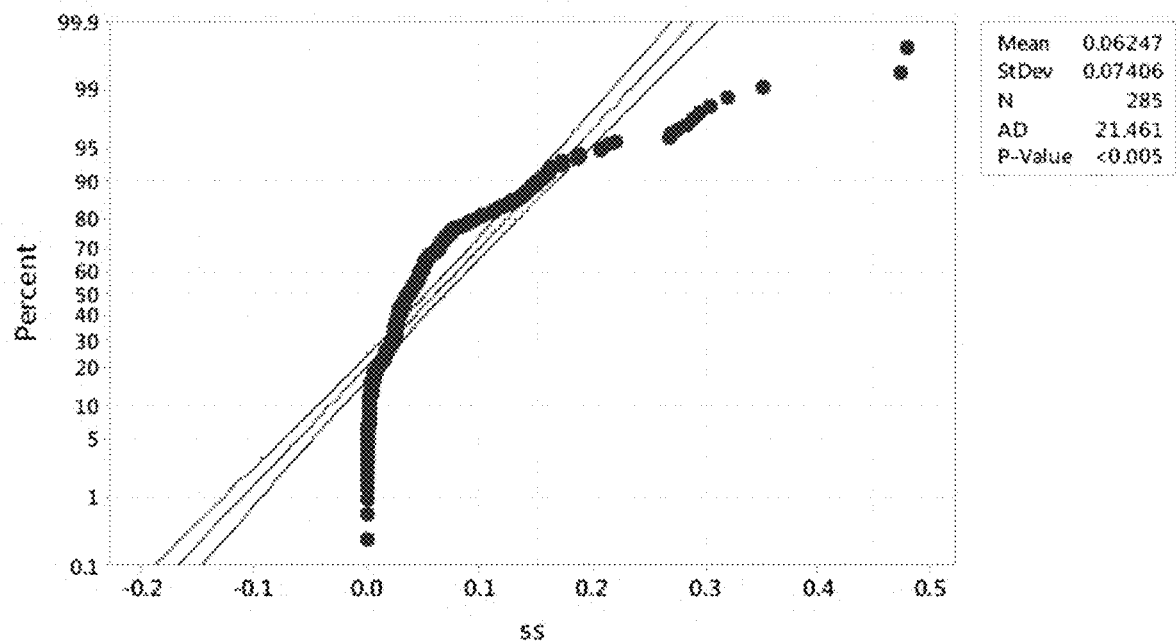
FIG. 6 is a probability plot of SS for Protein A column wash front without transformation.
Figure 7:
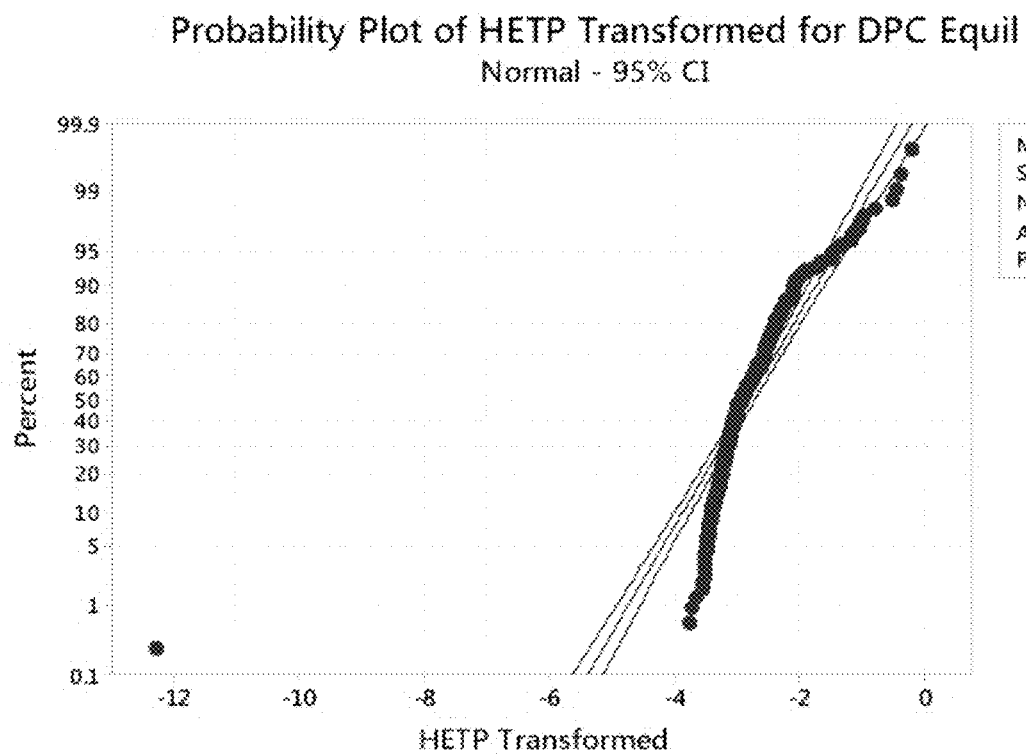
FIG. 7 is a probability plot of HETP for Protein A column equilibration front with natural log ($\lambda=0$) transformation.
Figure 8:
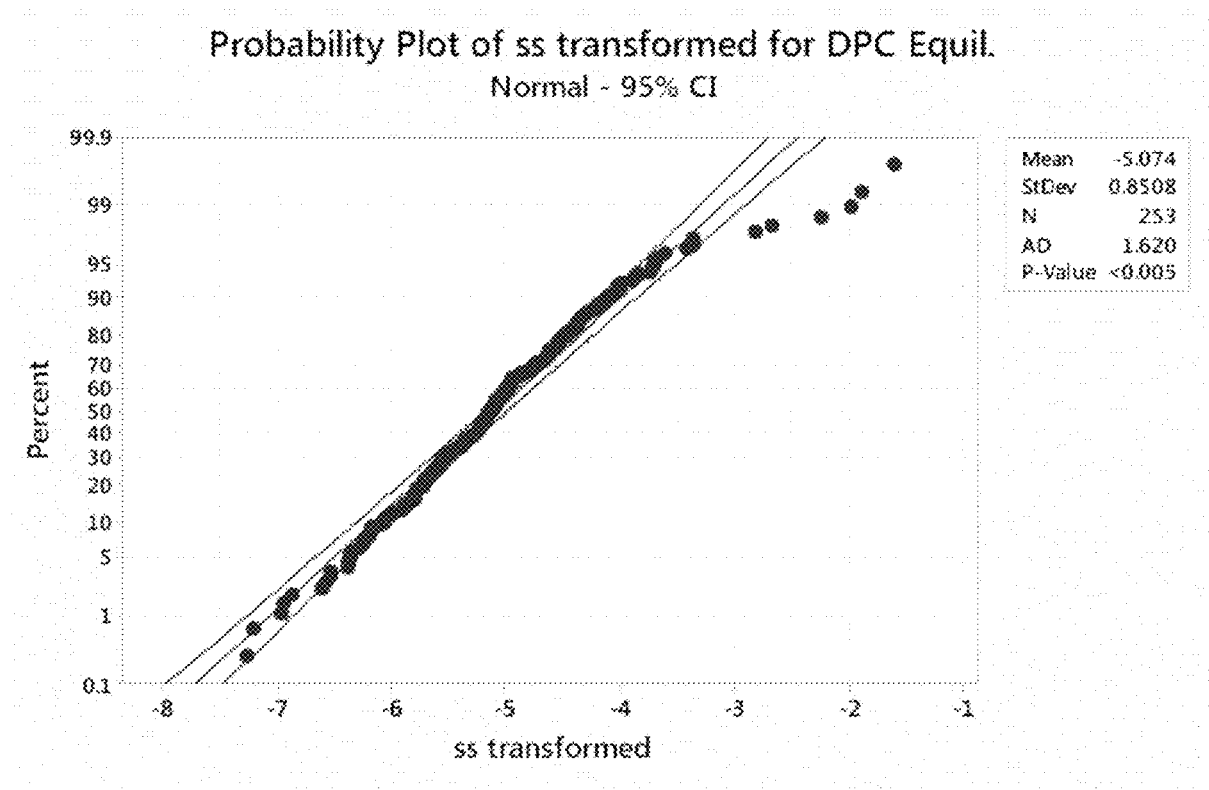
FIG. 8 is a probability plot of SS for Protein A column equilibration front with natural log ($\lambda=0$) transformation.
Figure 9:
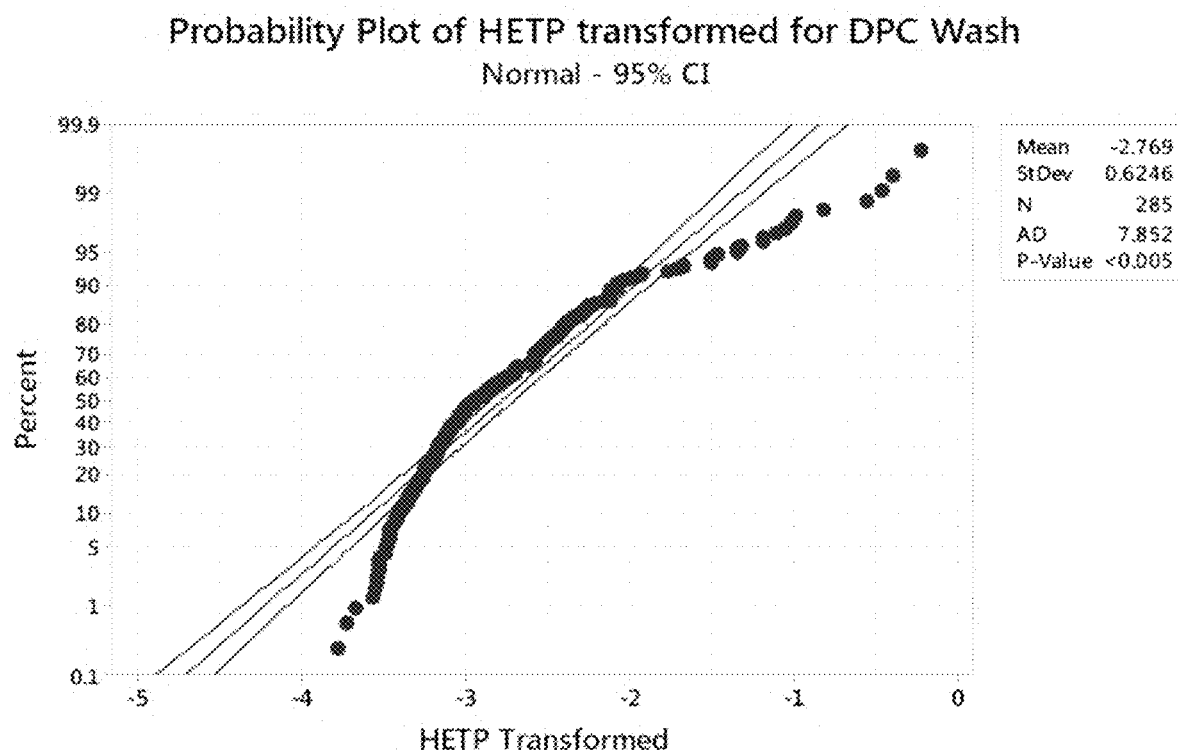
FIG. 9 is a probability plot of HETP for Protein A column wash front with natural log ($\lambda=0$) transformation.
Figure 10:
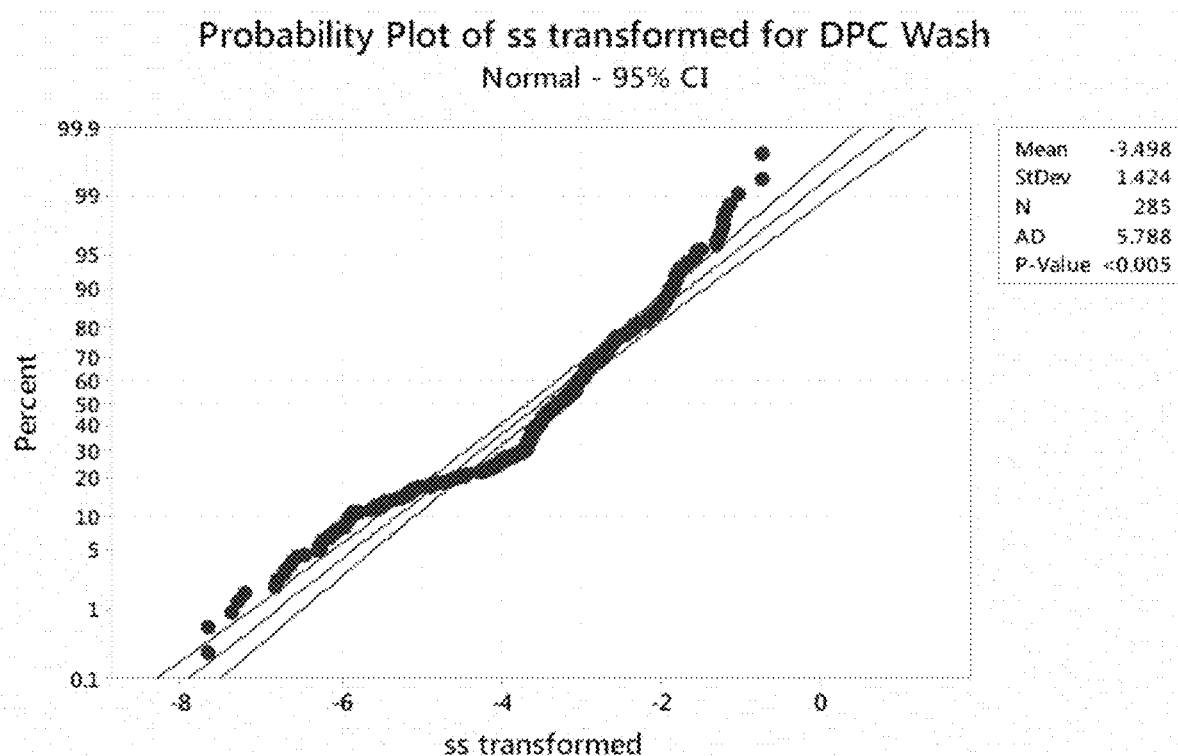
FIG. 10 is a probability plot of SS for Protein A column wash front with natural log ($\lambda=0$) transformation.

FIG. 2 is a diagram providing an overview of the method and system of operating a chromatography column and assessing column efficiency in real-time as described herein. As shown in FIG. 2 and described supra, the system 10 includes a chromatography column 12 used to separate biomolecules introduced into the column as a complex mixture, i.e., eluent 14, a detector 20 that detects a column output signal in the eluate as it elutes from the chromatography column, a communications interface 22 that transmits signal/data from the detector 20, a column qualification computing device 24, and a server 26.

Chromatography column 12 is filled with a permeable, semi-permeable, or impermeable solid phase column packing material. Suitable chromatography columns and column packing material are described supra. The eluent 14 containing the biomolecules of interest is introduced into the chromatography column 12. A mobile phase 16 is also introduced to the chromatography column 12. The mobile phase 16 facilitates separation of the biomolecules through the stationary phase of the chromatography column 12 and elution of the biomolecules in the eluate through the output 18 of the chromatography column. In accordance with the method as described herein, the mobile phase 16 comprises the sequentially introduced column buffers and/or wash reagents that differ in one or more physical or chemical properties from each other as described infra, e.g., pH, conductivity, salt concentration. These differences in one or more physical or chemical properties are detected in the eluate by the detector 20.

Detector 20 is coupled to the output 18 of chromatography column 12. Accordingly, detector 20 monitors and collects the column output signal via the eluate of chromatography column 12. Suitable detectors and the properties of the eluate, i.e., the column output signal, detected are described supra. The detector is coupled to a communications interface unit 22 that transmits data collected by the detector 20 (e.g., column output signal and accumulated flow parameters) to a column qualification computing device 24 for data processing and/or a server 26 for storage.

The column qualification computing device 24 of the system described herein can be any computing device, e.g., a computer, a personal computing device, smartphone, etc. that includes a central processing unit (CPU) or processor 32, a memory 30, a network interface 28, and a user interface 34 which are coupled together by a bus 36 or other link. The column qualification computing device 24 may include other types and/or numbers of components and elements in other configurations.

The processor 32 in the column qualification computing device 24 executes a program of stored instructions for one or more aspects of gamma distribution transition analysis described and illustrated by way of the examples herein, although other types and/or numbers of processing devices could be used and the processor 32 can execute other types and/or numbers of programmed instructions. In one embodiment, the processor 32 is located solely on the column qualification computing device 24. In another embodiment, the processor is distributed between the detector 20 and the column qualification computing device 24. For example, in one embodiment, the processor 32 of the column qualification computing device 24 comprises a microcontroller that is coupled to the detector. In this embodiment, the microcontroller serves as an on-board processor that is capable of mapping or converting data collected by the detector 20 into a digital signal that is transmitted to the column qualification computing device 24. The microcontroller coupled to the one or more detectors is capable of carrying out one or more processing functions of the column qualification computing device 24.

The memory 30 in the column qualification computing device 24 stores these programmed instructions for one or more aspects of the GDTA as described herein. A variety of different types of memory storage devices, such as a random access memory (RAM) and/or read only memory (ROM) in the timing processor device or a floppy disk, hard disk, CD ROM, DVD ROM, or other computer readable medium which is read from and written to by a magnetic, optical, or other reading and writing system that is coupled to the processor 32 in the column qualification computing device 24, can be used for the memory 30.

The network interface 28 of the column qualification computing device 24 operatively couples and facilitates communication between the column qualification computing device 24 and the detector 20, although other types and/or numbers of communication networks or systems with other types and/or numbers of connections and configurations can be used.

The column qualification computing device 24 may further comprise a user interface 34, such as, for example, a graphical user interface, a touch user interface, or a web-based user interface. The user interface is configured to display information regarding the chromatography column qualification parameters to the user. The user interface is also configured to receive input from the user regarding the chromatography column parameters.

The server 26 depicted in FIG. 2 can be one or a plurality of computing devices that each include a CPU or processor, a memory, and a network interface, which are coupled together by a bus or other link similar to that described for the column qualification computing device 24. The server 26 may include other types and/or numbers of components and elements in other configurations.

Communication interface(s) 22 of the system described herein can include one or more local area networks (LANs) and/or wide area networks (WANs). By way of example only, the communication interface(s) 22 can use TCP/IP over Ethernet and industry standard protocols, including hypertext transfer protocol (HTTP) and/or secure HTTP (HTTPS), although other types and/or numbers of communication networks may be utilized.

Another aspect of the present disclosure relates to a non-transitory computer readable medium having stored thereon instructions for chromatography column qualification using the gamma distribution transition analysis. These instructions comprise executable code which when executed by a processor, causes the processor to perform steps comprising, collecting column outlet signal and accumulated flow parameters at two or more intervals of at least one mobile phase transition front during a first operation of the chromatography column comprising column packing; determining a model gamma cumulative distribution curve based on the collected column outlet signal and accumulated flow parameters for the at least one mobile phase transition front using Formula Ia as described supra for a rising transition front or Formula Ib as described supra for a falling transition front; calculating a height equivalent theoretical plate (HETP) value for the at least one mobile phase transition front using Formula II as described supra and the model gamma cumulative distribution curve parameters of k, $\theta$, and $V_i$ as described herein; and assessing quality of the chromatography column packing based on said calculated HETP value.

Another aspect of the present disclosure is directed to a chromatography column qualification device. This device comprises a processor and a memory coupled to the processor. The memory is configured to execute programmed instructions stored in the memory. These instruction include: collect column outlet signal and accumulated flow parameters at two or more intervals of at least one mobile phase transition front during a first operation of the chromatography column comprising column packing; determine a model gamma cumulative distribution curve based on the collected column outlet signal and accumulated flow parameters for the at least one mobile phase transition front using Formula Ia for a rising transition front or Formula Ib for a falling transition front as described supra; calculate a height equivalent theoretical plate (HETP) value for the at least one mobile phase transition front using Formula II as described supra and the model gamma cumulative distribution curve parameters of k, θ, and $V_i$ as described herein, and assess quality of the chromatography column packing based on said calculated HETP value.

EXAMPLES

Example 1—Application of the Gamma Distribution Transition Analysis for Column Qualification of Protein a Chromatography Columns Used in to REMICADE® (Infliximab) Manufacturing Overview The manufacturing process of the therapeutic antibody, REMICADE® (infliximab), involves several stages, four of which involve chromatography purification. The gamma distribution transition analysis (GDTA) for column qualification was applied to two or three transitions during each of these column steps. This Example describes the application of the GDTA method to the Protein A column purification step employed during REMICADE® (infliximab) manufacturing. The purification process includes two transition fronts, i.e., equilibration and intermediate wash, that are appropriate for GDTA as described herein.

The GDTA was executed on 129 fronts from the consecutive purification of 69 batches of REMICADE® (infliximab), comprising 60 equilibration and 69 wash fronts. The gamma front distribution analysis was performed concurrently with manufacturing and did not impact the manufacturing process. All manufacturing, monitoring and controls were performed using current, effective procedures. During the column chromatography purification of REMICADE® (infliximab), conductivity (i.e., the column outlet signal) and flow of the eluent (i.e., accumulated flow) were recorded.

In addition to the application of the GDTA to column operation in real time, historical data for 285 batches processed over the course of the four previous years was also collected and analyzed as described herein. The data set included 253 equilibration fronts and 285 wash fronts, for a total of 538 historical fronts. The equilibration fronts were not generated for 32 batches in which pre-use sanitizations were performed. This data set was selected to provide an even distribution through the life of the columns and represents 11 column packs.

GDTA Protocol:

For each transition front during Protein A column purification, i.e., wash and equilibration, the conductivity and accumulated flow were recorded. Determination of the starting point was accomplished by evaluating the trends for pre-column conductivity and pressure in order to identify the point at which the column was placed inline. A spreadsheet was created and setup to retrieve flow and conductivity data from the server using a calculated 10 second interval for the duration of the front.

The conductivity data was normalized by setting the maximum value to 1 and the minimum value to 0 and scaling the other points proportionally. Additionally, the flow was converted to column volumes.

A starting gamma CDF was calculated by using the same starting k, θ, $V_i$ parameters as the PI module. $V_i$ was subtracted from each volume value in the x term of the gamma distribution function. In order to normalize the conductivity, which was increasing during the purification, the conductivity values were set to 0 for volumes less than $V_i$ and the maximum was set to 1.

The difference (error) between each conductivity value and the model fit for each volume point was calculated. Additionally, the sum of squares for the error between 0.5 and 1.8 CV was calculated. The best fit gamma CDF parameters were calculated using the Excel solver to find the k, θ, and $V_i$ parameters that produced a model curve with the minimum value for the sum of squares using $$C = 1 - \frac{1}{\Gamma(k)} \gamma\left(k, \frac{V - V_i}{\theta}\right).$$ Formula Ia The solver was run for 10,000 iterations using the GRG non-linear method with constraints of k≥0.0001 and $V_i$≥0 to ensure that a closest fit was reached.

The following parameters were calculated from the final values of k, θ, and $V_i$:

Mean ($V_m$), $\mu = k\theta + V_i$,

Variance, $\sigma^2$(sigma squared) $= k\theta^2$

Mode $= (k-1)\theta + V_i$ $$HETP = \frac{L}{N_p} = \frac{\sigma^2}{\mu^2} L = \frac{k\theta^2 L}{(k\theta + V_i)}$$

The average flow rate and pre-column pressure was calculated for the period from 0.5 to 1.8 CV for each front.
Analysis and Evaluation of Acceptance Criteria:
Normality Results for HETP and SS for both the equilibration and wash fronts were evaluated for normality by creating a probability plot. In the probability plots (FIGS. 3-12) the data points (results for HETP or SS) represent the actual cumulative distribution observed in the sample. The lines represent the fitted cumulative distribution and the upper and lower confidence intervals based on a normal distribution using the parameters estimated from the sample. The percentile scale is transformed so the fitted distribution forms a straight line. The HETP and SS data sets are each bounded by 0 on the lower end, however, the normal distribution model suggests negative values. The resulting probability plots show a curved shape. See FIGS. 3-6. Thus, the results fit better using a log transformation. See FIGS. 7-10 for the probability plot of the log transformed data.

Figure 11:
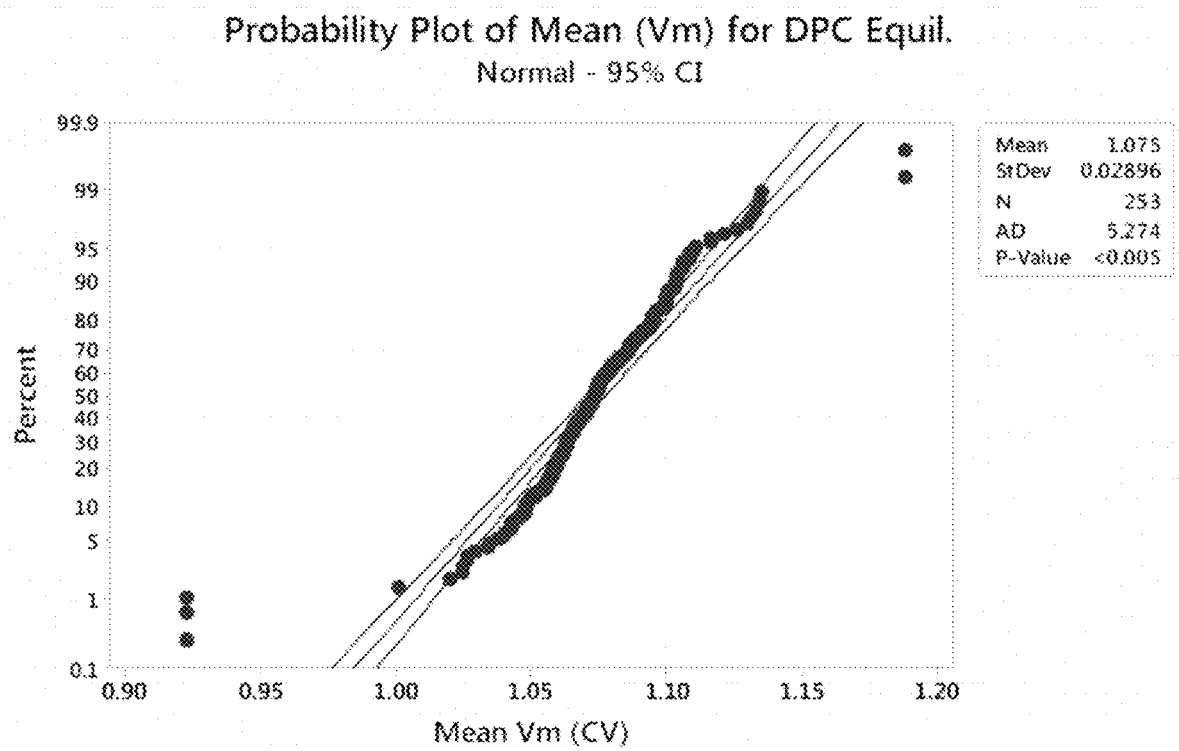
FIG. 11 is a probability plot of the Mean ($V_m$) for Protein A column equilibration.
Figure 12:
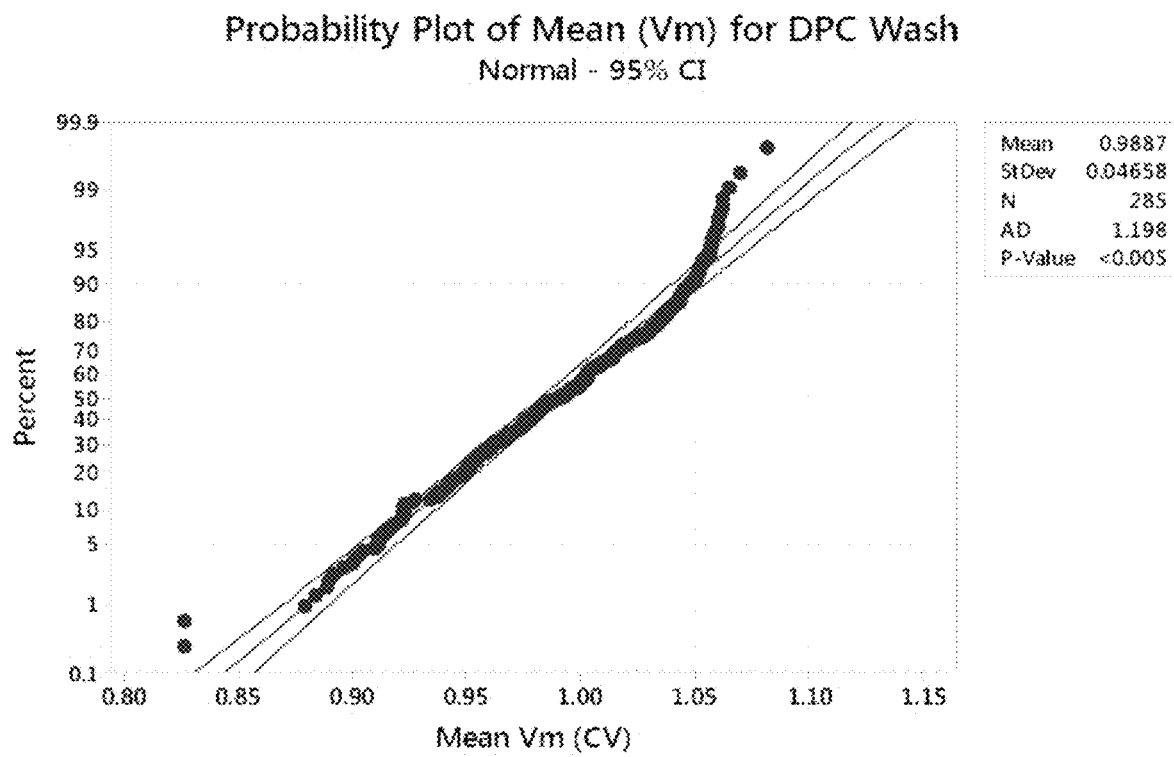
FIG. 12 is a probability plot of the Mean ($V_m$) for Protein A column wash front.

Data for the Mean ($V_m$) was also evaluated for normality. FIG. 11 and FIG. 12 show that the data fits the normal distribution, with only a few outliers. Thus, no transformation was needed. This parameter was not specified in the protocol but provides a useful assurance that the curve fit is valid. Control limits for this parameter will also be generated from this analysis.
Identification of Outliers and Causes of Variation.

In order to identify outliers and assess variability in the results, control charts for each parameter were generated. See FIGS. 13-22. Control charts used the transformed data for the HETP and SS, where natural log transformation was applied. The data is also plotted in a time series plot with the transformed upper control limit for each of these parameters.

Figure 13:
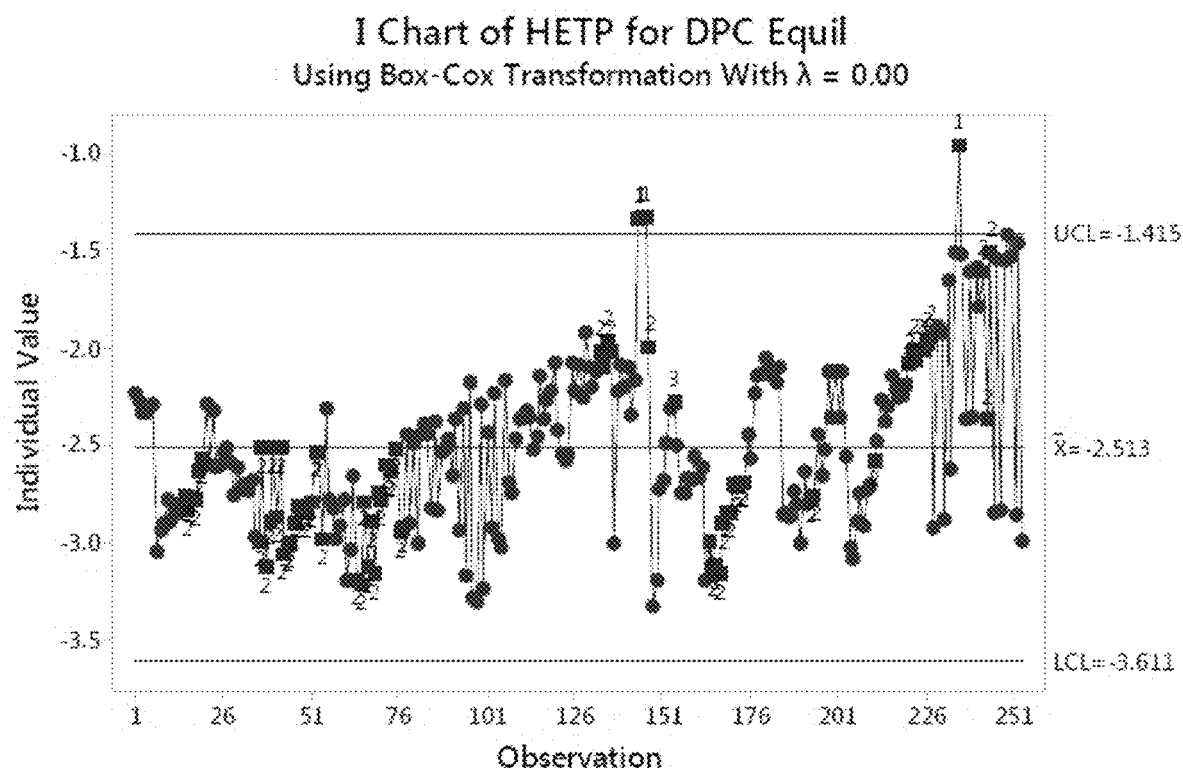
FIG. 13 is a control chart of HETP for Protein A column equilibration front with natural log ($\lambda=0$) transformation. UCL=upper control limit; LCL=lower control limit. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.
Figure 18:
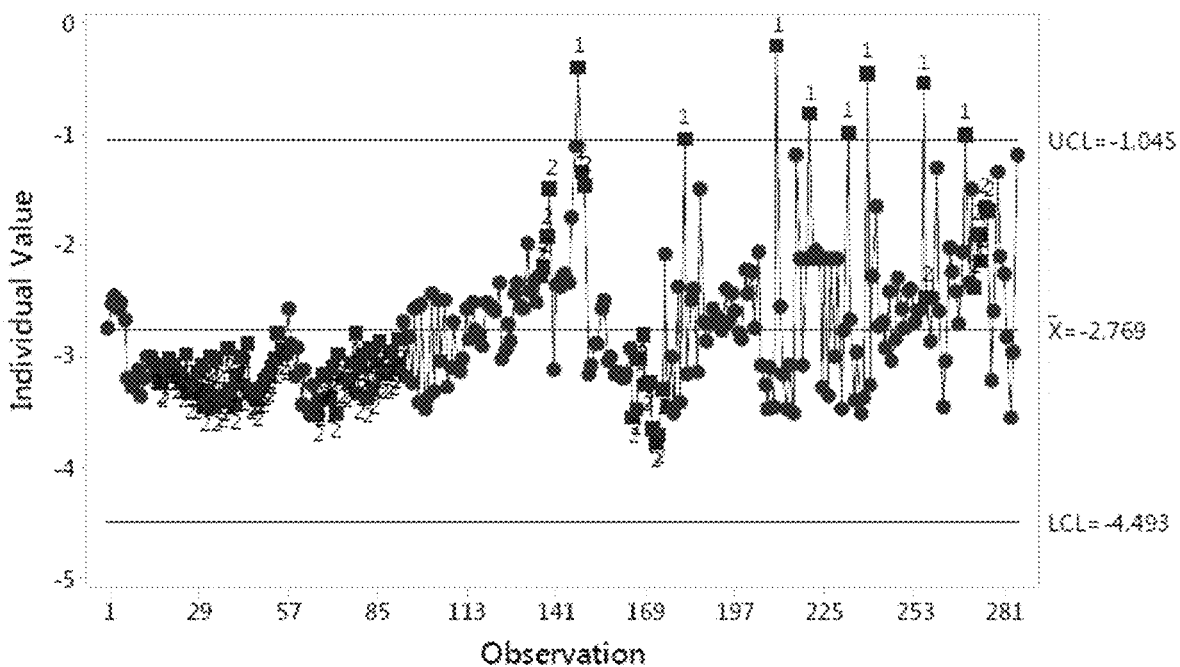
FIG. 18 is a control chart of HETP for Protein A column wash front with natural log ($\lambda=0$) transformation. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.

HETP: A number of outliers and trends are apparent in the HETP results for both Equilibration and Wash fronts. Additionally, FIG. 13 and FIG. 18 show trends in the data based on Shewhart rules 1, 2 and 3, represented by squares in the figures and numbered according to the following.

| Test | Rule |
| --- | --- |
| 1 | 1 point is outside the control limits. |
| 2 | 8 points on the same side of the center line. |
| 3 | 6 consecutive points are steadily increasing or decreasing. |

The batches associated with these excursions were not excluded from the analysis as they are representative of the acceptable process.

Both of the control charts (FIG. 13 and FIG. 18) show a number of Shewhart rule 1 violations, which also exceeds the control limits. In each case the issues were identified and corrected by reconditioning the columns.

Figure 23:
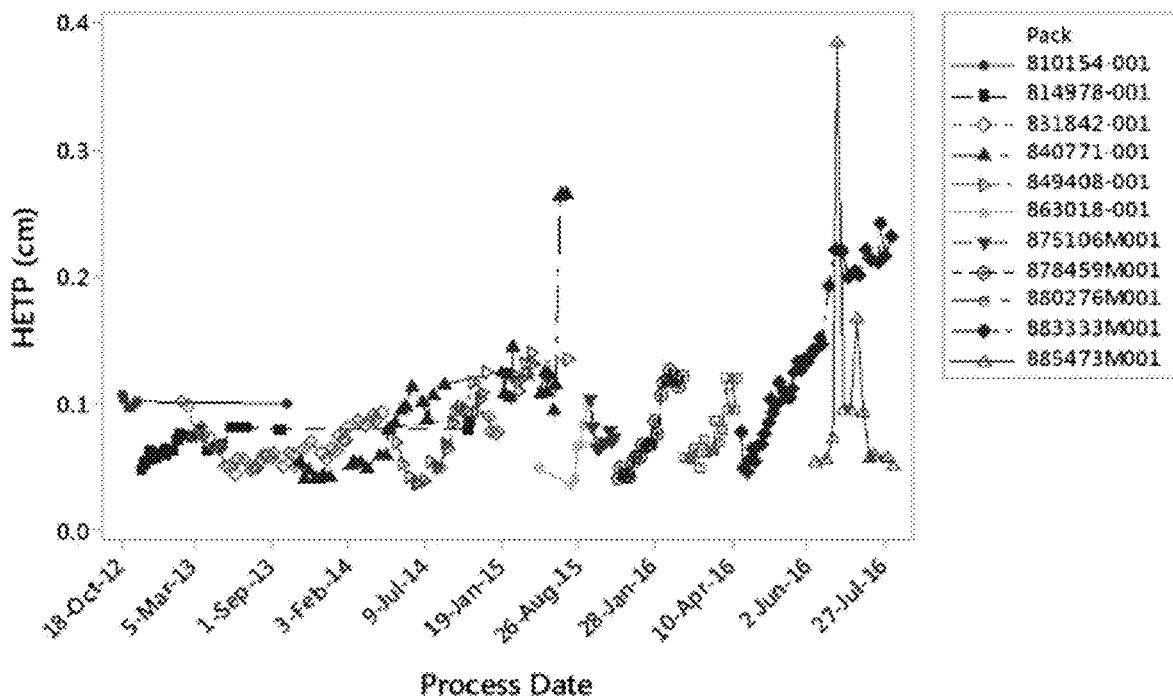
FIG. 23 is a time series plot of HETP results for direct product capture (DPC) Protein A column equilibration front grouped by column pack.
Figure 24:
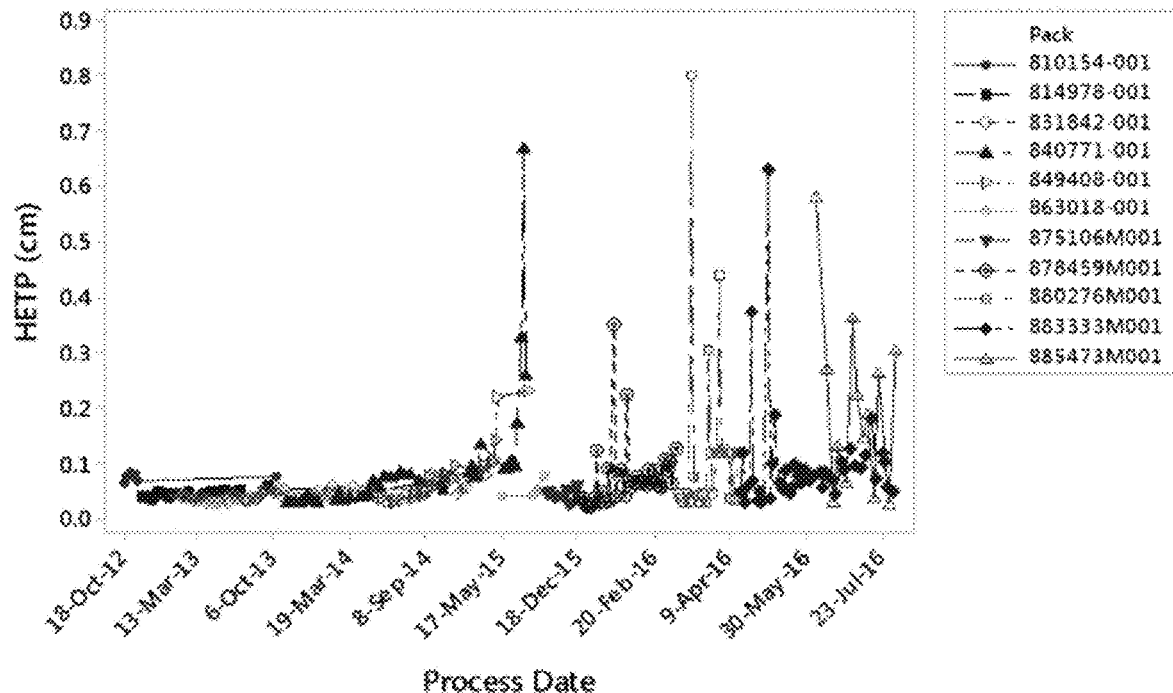
FIG. 24 is a time series plot of HETP results for DPC Protein A column wash front grouped by column pack.
Figure 25:
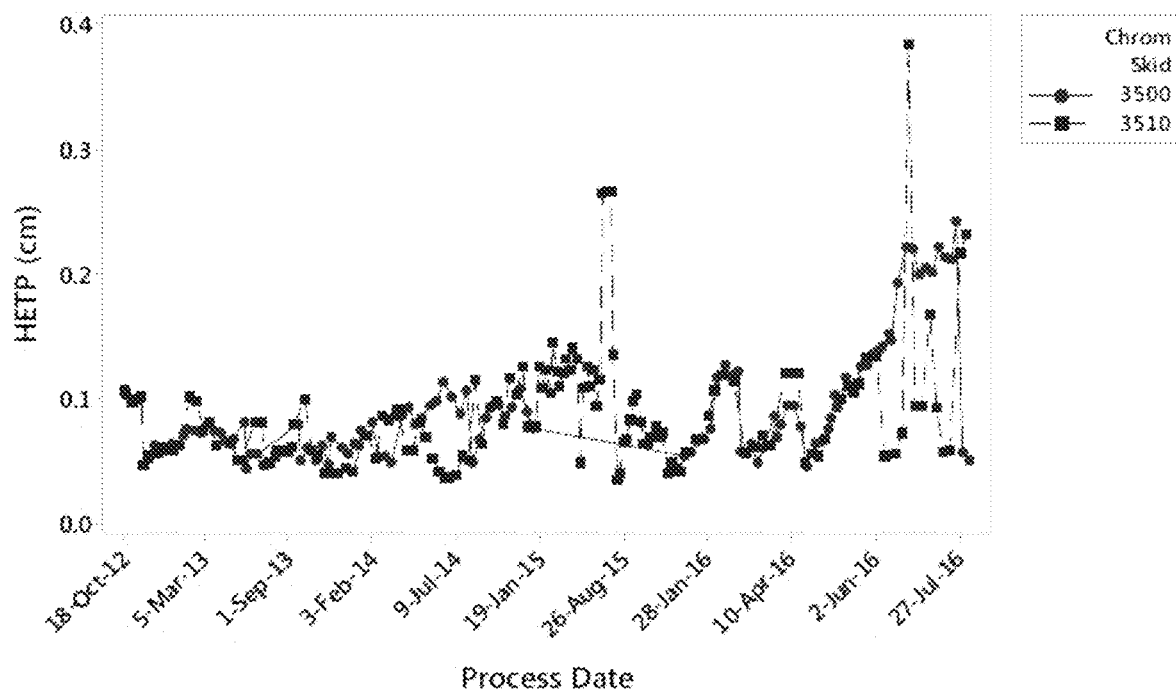
FIG. 25 is a time series plot of HETP results for DPC Protein A column equilibration front grouped by skid.
Figure 26:
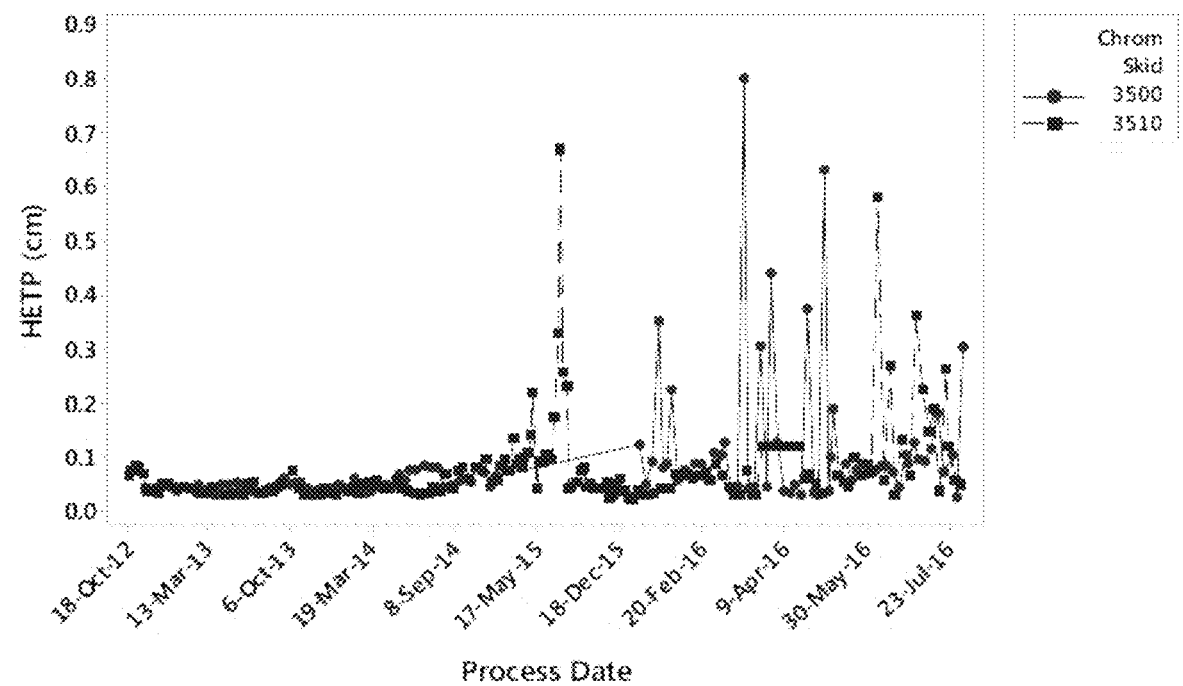
FIG. 26 is a time series plot of HETP results for DPC Protein A column wash front grouped by skid.
Figure 27:
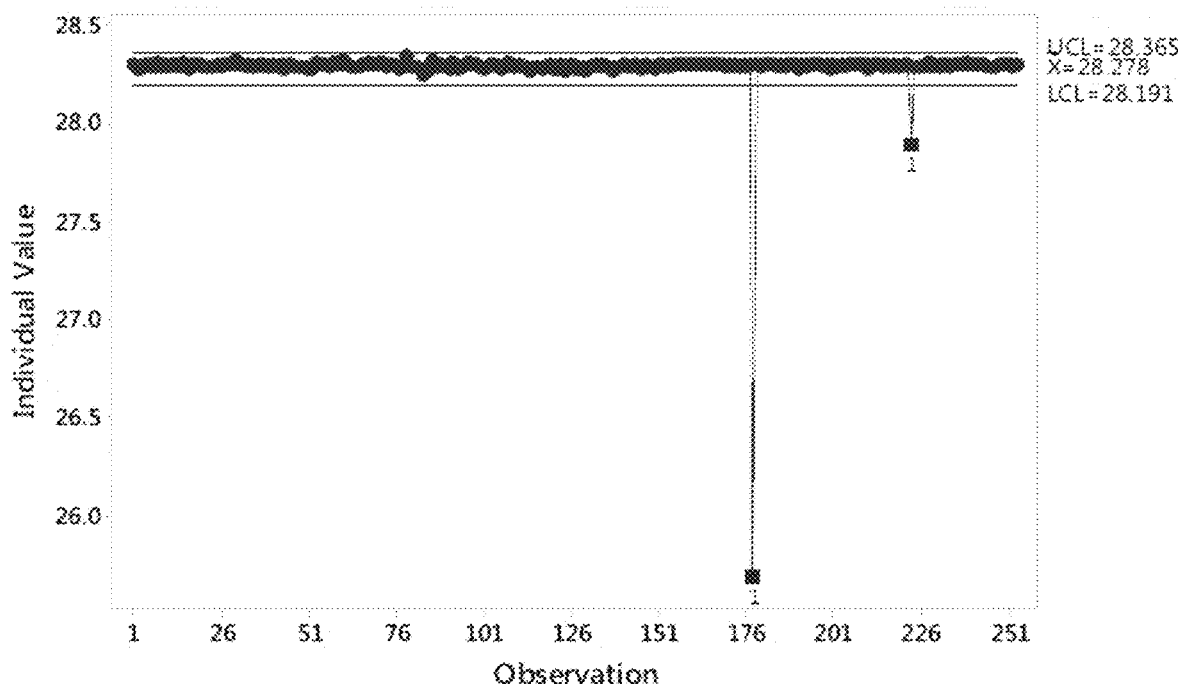
FIG. 27 is chart showing the average flow for DPC Protein A column equilibration. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.
Figure 28:
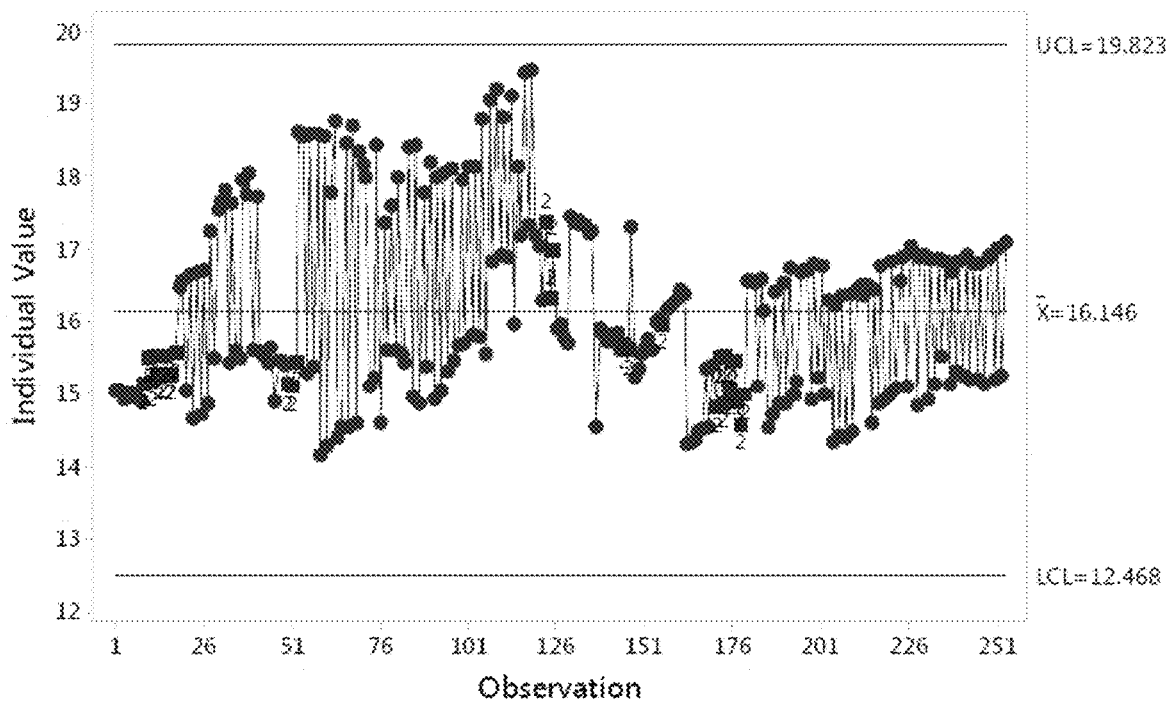
FIG. 28 is a chart of the average pre-column pressure during equilibration. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.
Figure 29:
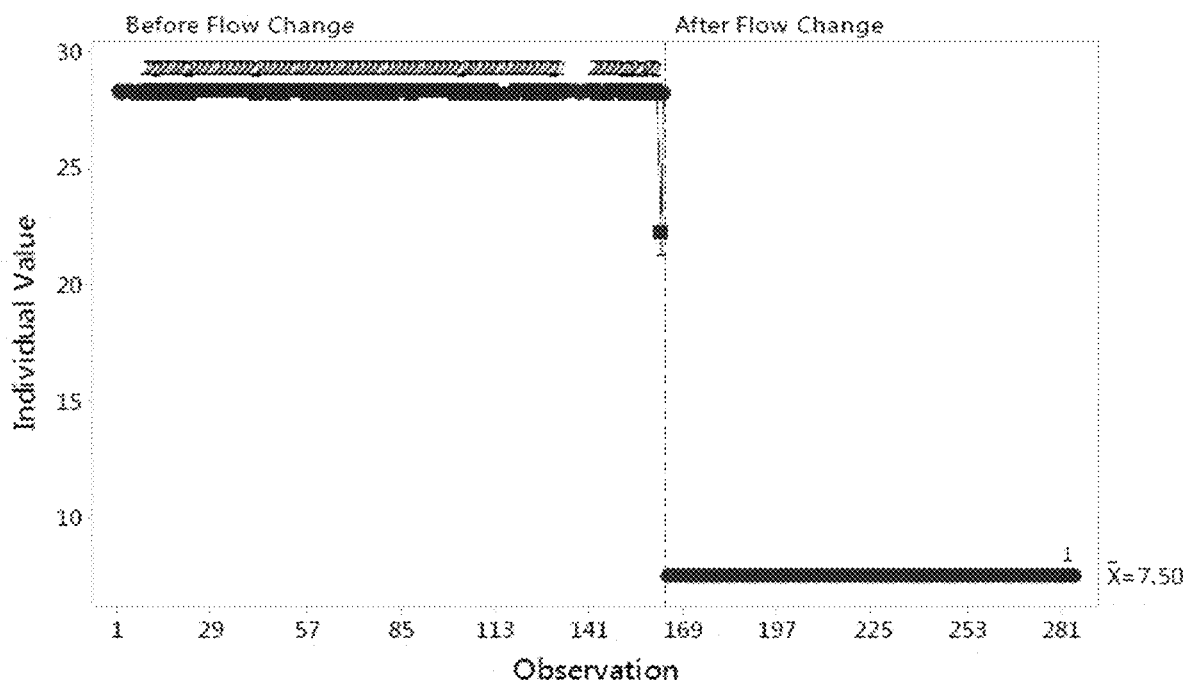
FIG. 29 is a chart of the average wash flow rate for DPC Protein A column wash front. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.
Figure 30:
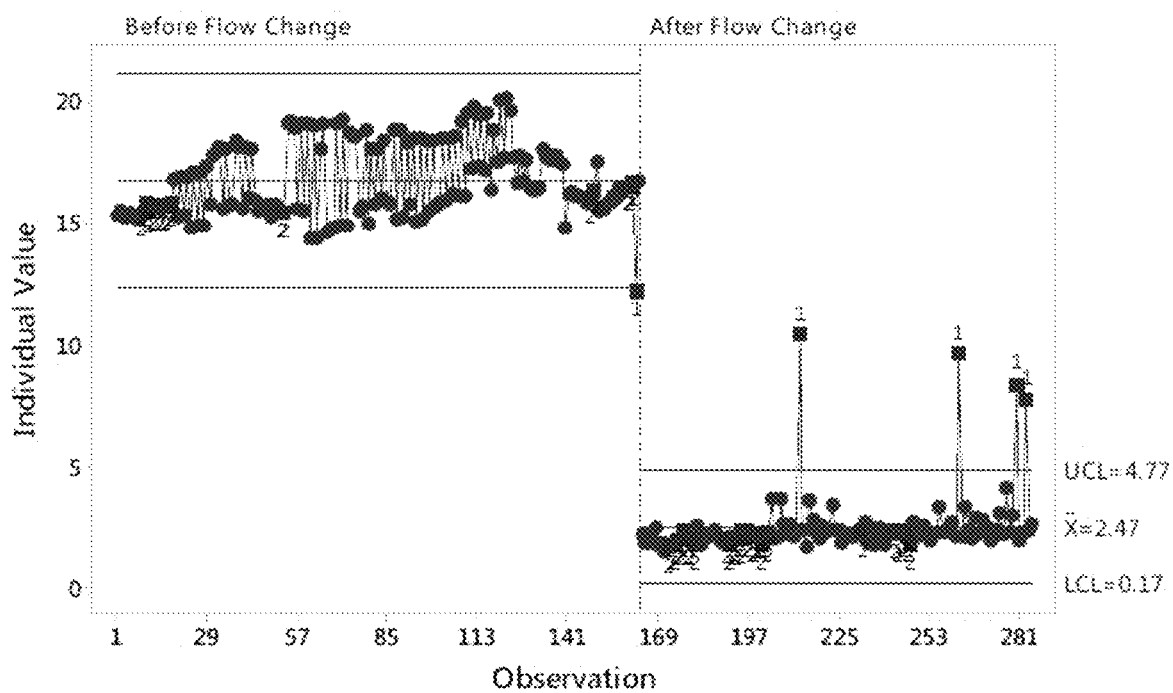
FIG. 30 is a chart of the average wash pressure for the DPC Protein A column wash front. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.

As expected, a number of runs met the criteria for rule 2 and 3 due to variation in the column packs. In order to further assess the trends, time series plots were prepared with data grouped by column pack (FIGS. 23-24) and skid (FIGS. 25-26). These charts show that much of the special cause variation is attributed to column degradation and some isolated excursions. Trends of increasing HETP are apparent for each column over time for the equilibration front (FIG. 23). Excursions observed for the Wash front appear to be isolated to one skid or the other at different times (FIG. 26), suggesting that there may be a source of column performance variability in the skid.

Figure 15:
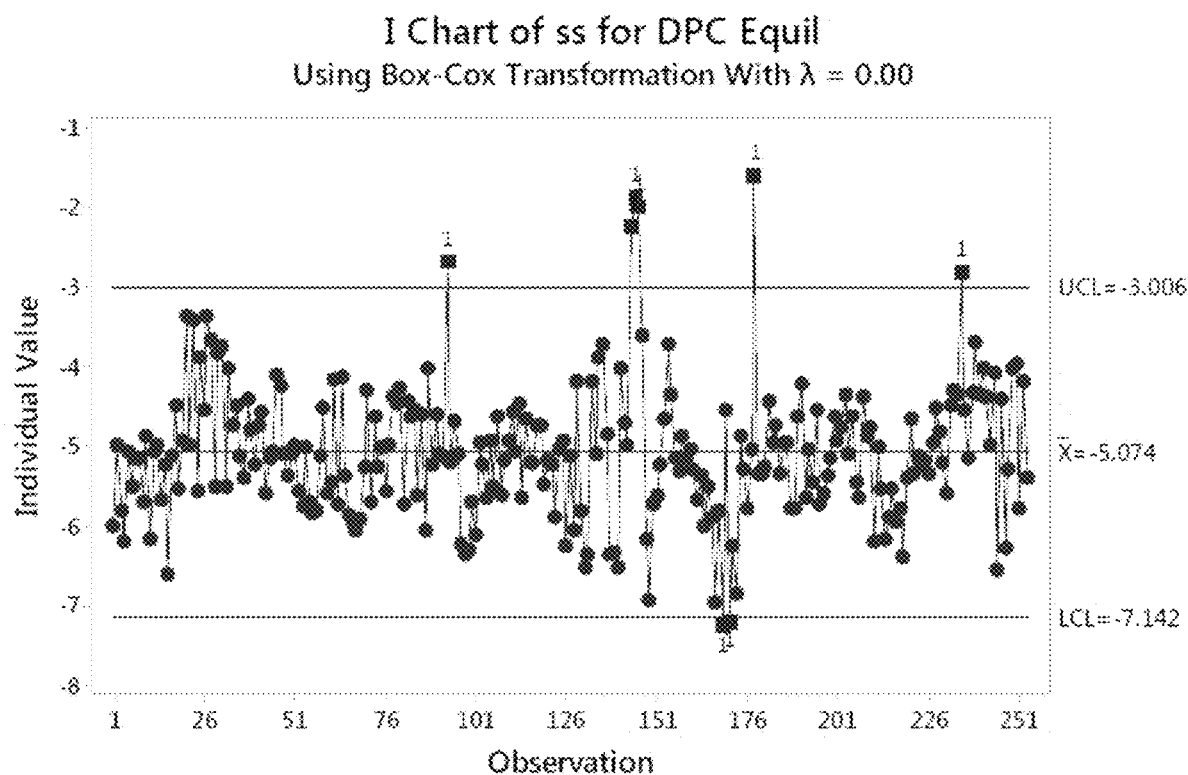
FIG. 15 is a control chart of the SS for Protein A column equilibration front with natural log ($\lambda=0$) transformation. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.
Figure 20:
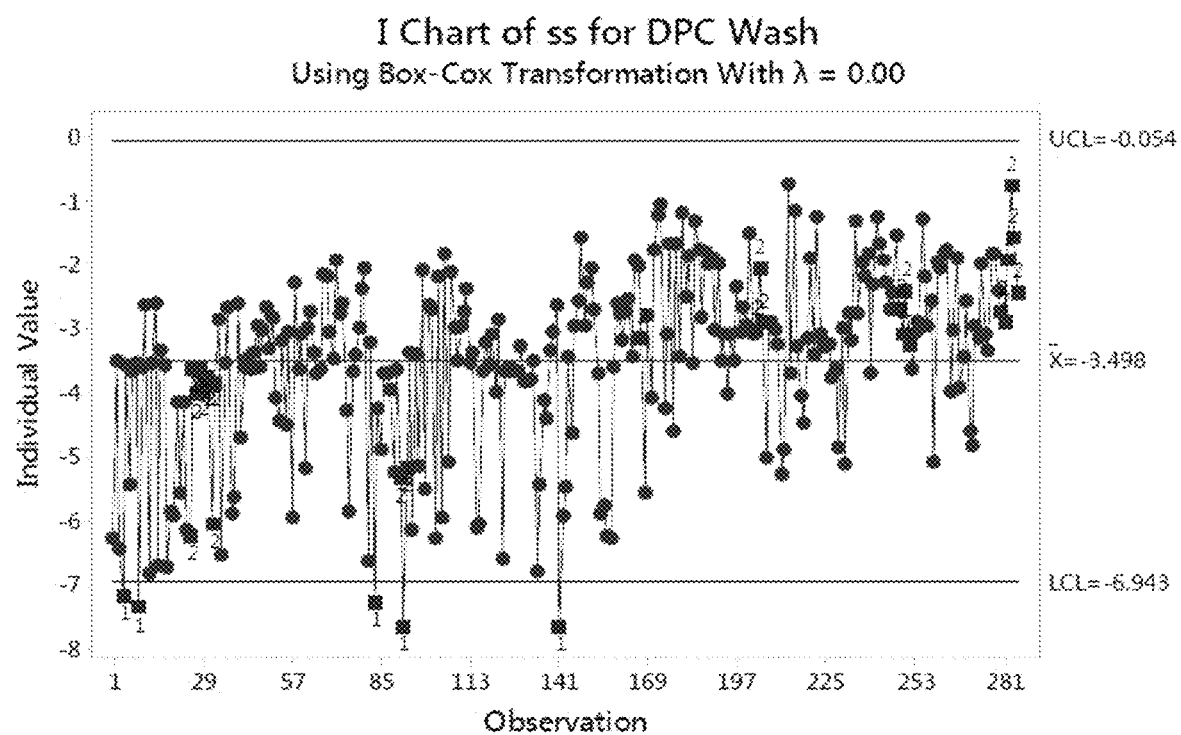
FIG. 20 is a control chart for SS for Protein A column wash front with natural log ($\lambda=0$) transformation. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.
Figure 21:
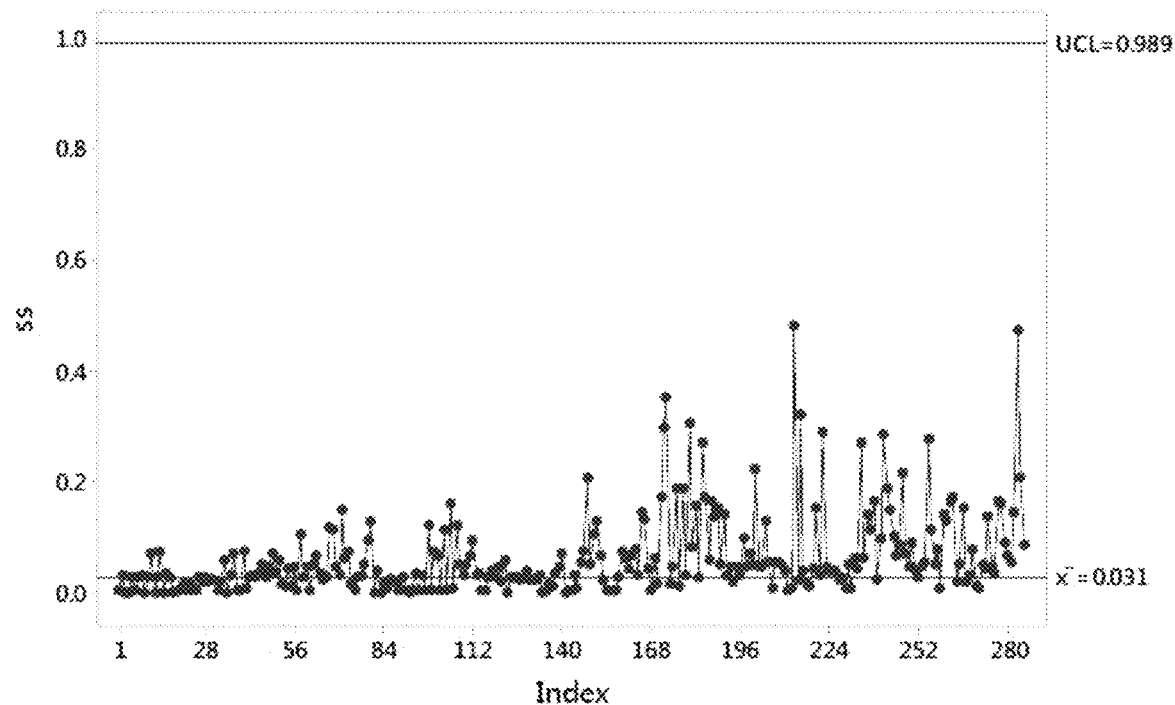
FIG. 21 is a time series plot of SS for Protein A column wash front. UCL is derived from transformed data in FIG. 20.
Figure 22:
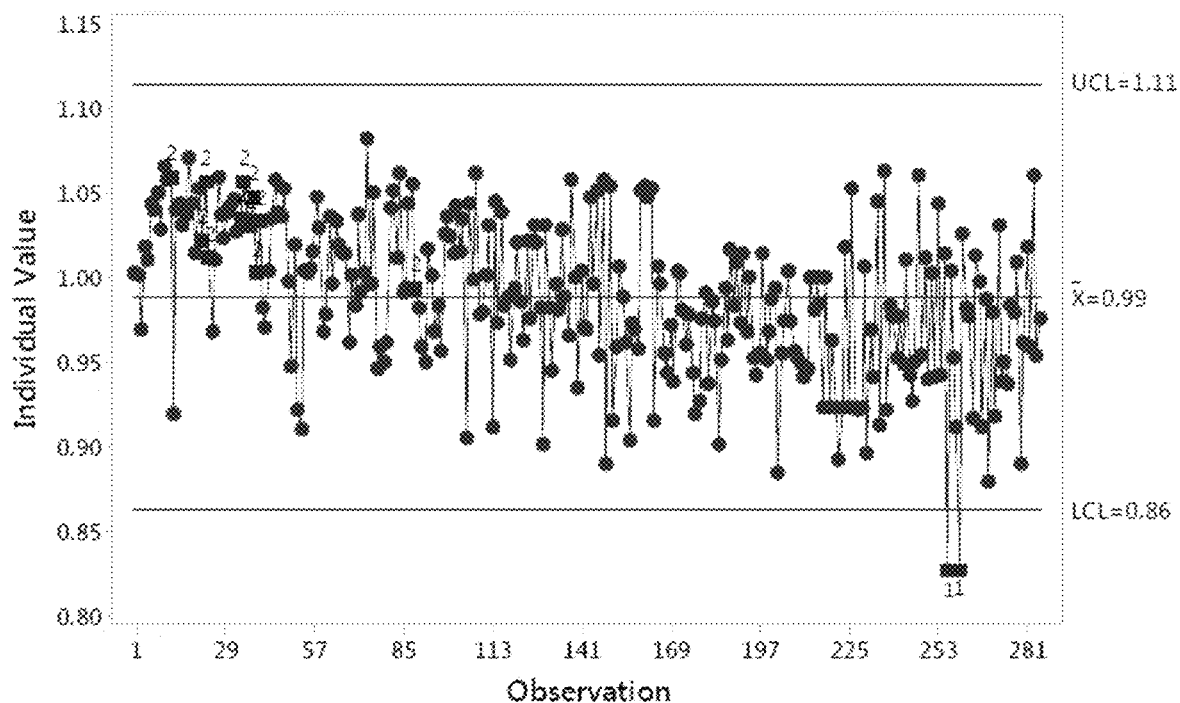
FIG. 22 is a control chart for Mean ($V_m$) for Protein A column wash front. Numbered points on the graphs show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.

Sum of Squares (SS): The sum of squares is a measure of how well the gamma distribution fits the process data. This measure will provide a check to ensure that the HETP result is valid. Control charts for the transformed data are shown in FIG. 15 and FIG. 20 for equilibration and wash, respectively. This measure only has an upper control limit. FIG. 15 shows 6 points where the upper control limit is exceeded. Four of these are associated with higher HETP. Batch 880572M had a flow disruption during the front which caused the SS to be high but did not impact HETP.

Evaluation of Flow and Pressure.

The average flow rate and pre-column pressure for the data set was evaluated to identify any outliers. The relationship between the differences identified and the results was assessed.

Figure 31:
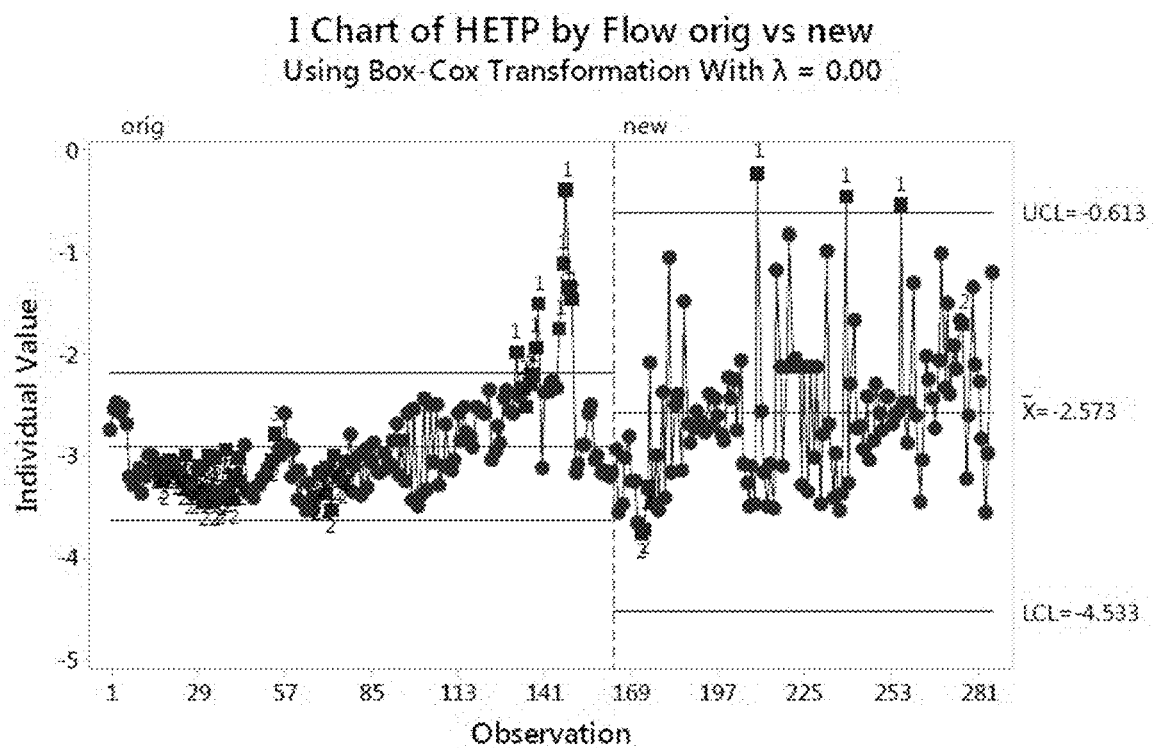
FIG. 31 is a chart showing the HETP before and after changing the wash flow rate. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.

Flow rate and pre-column pressure are trended in FIGS. 27-30. The charts show excellent control of flow rate for each of the steps. The Wash flow rate was changed during this assessment. Pre-Column pressure shows variations related to the skid and columns but is generally stable within a range. FIG. 31 shows that the HETP value is not significantly impacted by the wash flow rate change.

Control Limits for Protein a Column

HETP:

HETP is directly related to the column performance and is also affected by other factors in the system that may increase dispersion. The result must be >0. The control limits for HETP are best determined by using the natural log Box-Cox transformation ($\lambda=0$), as shown in FIG. 13 for the equilibration and FIG. 18 for the wash front. The control charts show control limits for the transformed data calculated by Minitab using the mean +/−3 standard deviations (see also Table 2 below). Standard deviation is determined based on the average moving range. A moving range of 100 was selected to account for the variation in column performance over the column life. The upper and lower control limits are reverse transformed (ex) to determine the control limits for the untransformed data.

Figure 14:
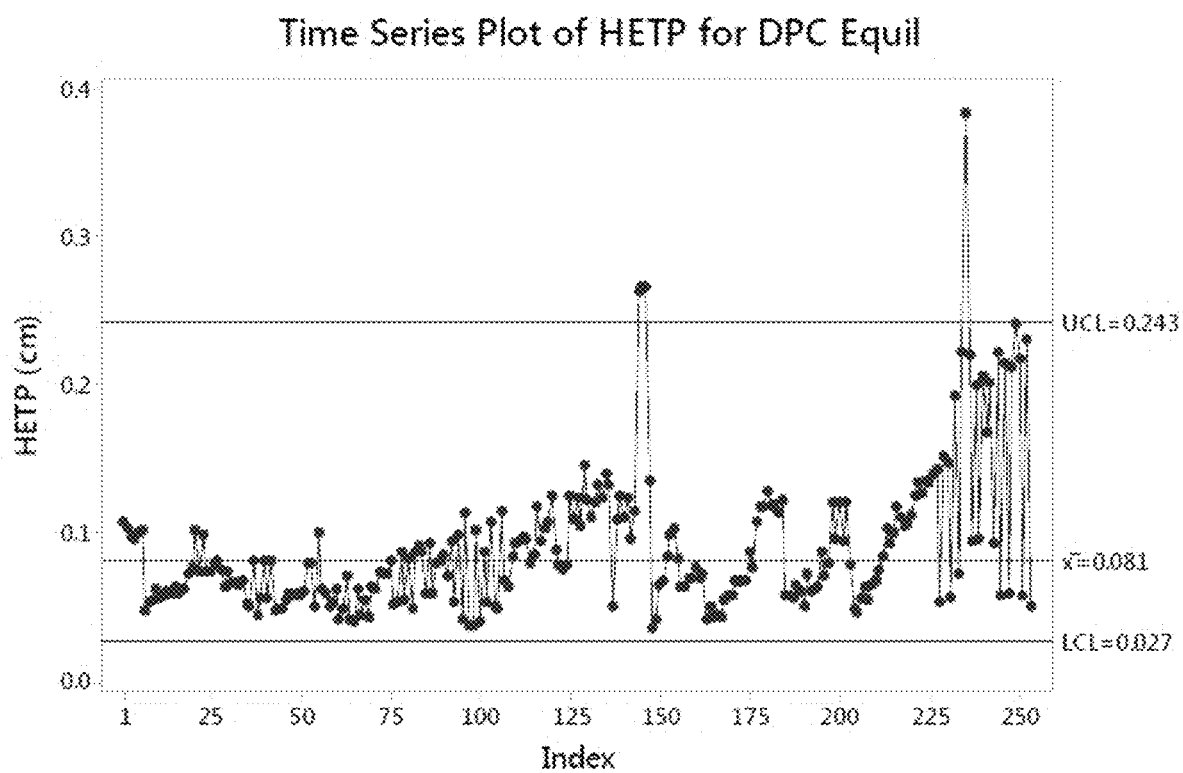
FIG. 14 is a time series plot of HETP for Protein A column equilibration front. The UCL is derived from transformed data in FIG. 13.
Figure 19:
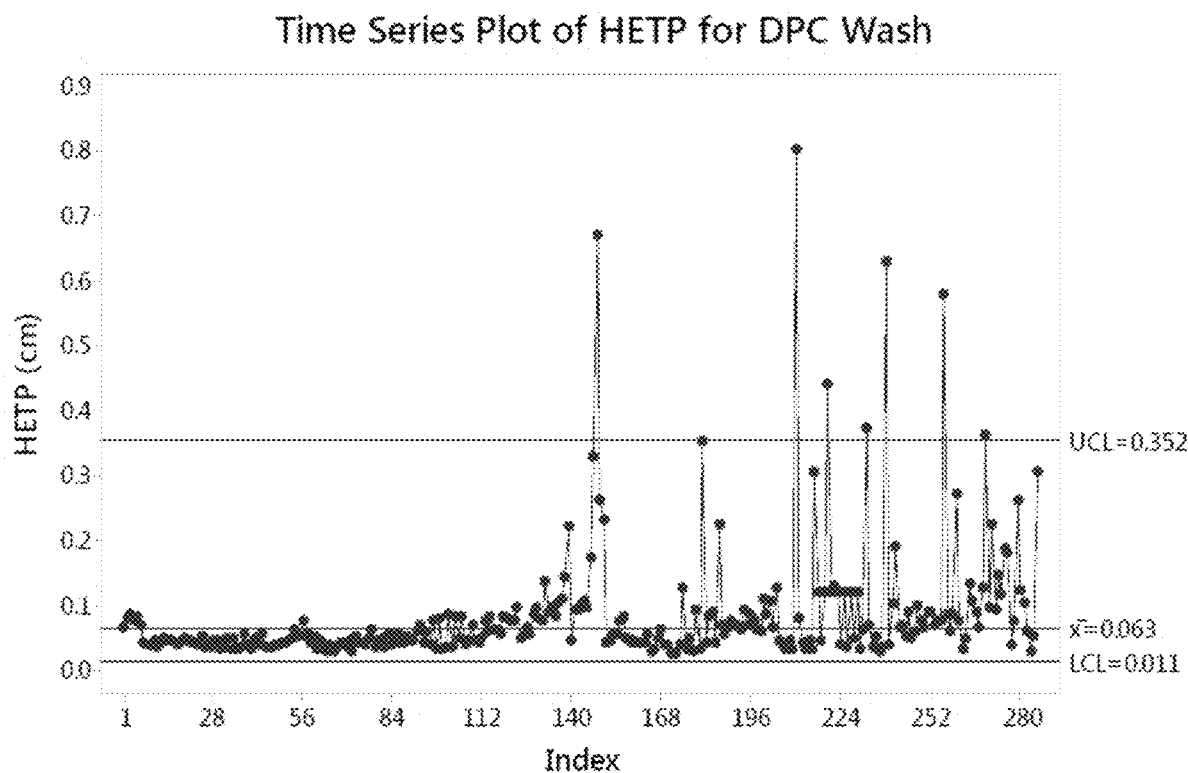
FIG. 19 is a time series plot of HETP for Protein A column wash front. UCL is derived from transformed data in FIG. 18.

A time series plot for each front's HETP results and control limits is shown in FIG. 14 and FIG. 19. Operation within these limits is expected to produce acceptable chromatographic performance based on this historical review. Values above the upper control limits may indicate column flow issues and should be evaluated further. Values below the lower control limits may be indicative of a calculation error.

Figure 16:
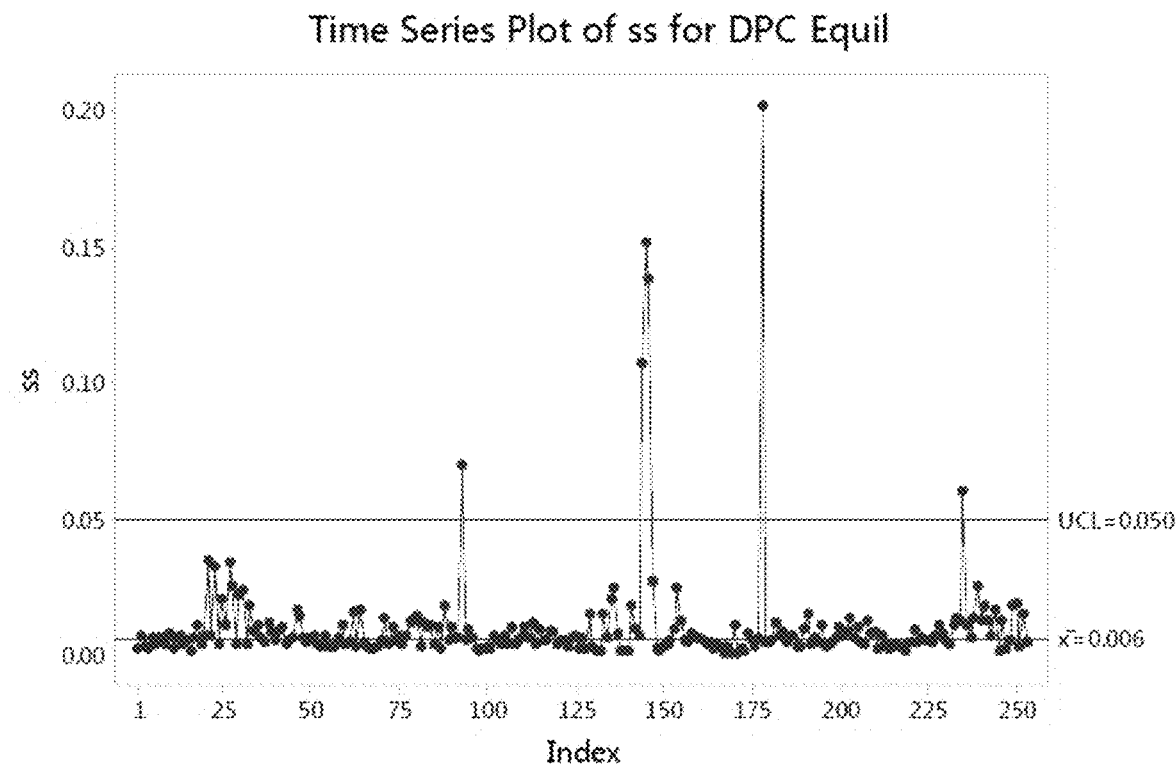
FIG. 16 is a time series plot of SS for Protein A column equilibration front. The UCL is derived from transformed data in FIG. 15.
Figure 17:
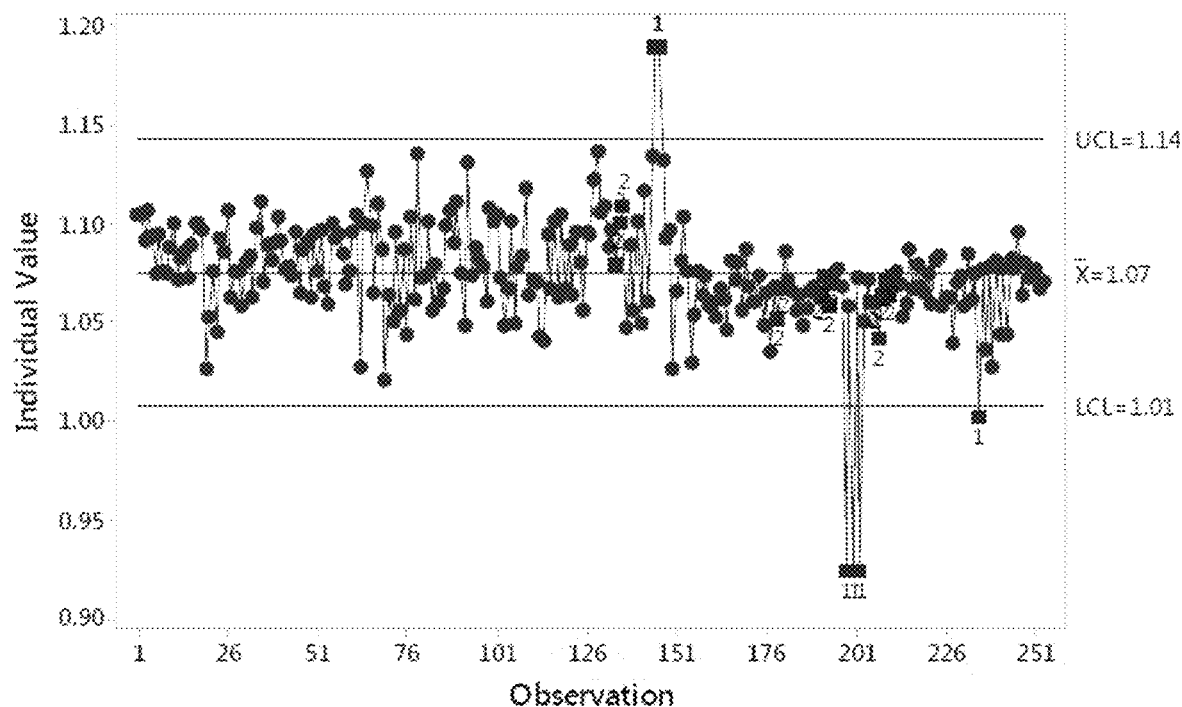
FIG. 17 is a control chart of the Mean ($V_m$) for Protein A column equilibration front. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.

Sum of Squares (SS):

The SS is a measure of how well the gamma distribution model fits the data. This measure is used to ensure that HETP values calculated using the GDTA method represent the process data. There is no lower limit and the result must be >0. The upper control limit for SS is best determined by using the natural log Box-Cox transformation ($\lambda=0$), as shown in FIG. 15 for the equilibration front and FIG. 20 for the wash front. The control charts show control limits for the transformed data calculated by Minitab using the mean +/−3 standard deviations. Standard deviation is determined based on the average moving range. A moving range of 100 was selected to account for the variation in column performance over the column life. The control charts show upper control limits for the transformed data which are reverse transformed to give 0.050 and 0.989 for the Equilibration and Wash fronts, respectively (see Table 2). A time series plot for each front's SS results and control limits is shown in FIG. 16 and FIG. 20. Results within the limits will ensure that the model fits the data as well as historical results. If the result is outside of this range, a special cause is likely.

Mean:

The mean was added as a second measure of the accuracy of the gamma distribution model. The mean represents the theoretical center of mass for the front and should always be near 1 column volume unless there are other factors in the system that cause it to shift, such as large extra column volume or interaction between the mobile phase and resin. The mean values for both equilibration and wash fronts are roughly normally distributed and do not need transformation, see FIG. 11 and FIG. 12. The mean for the equilibration front is tightly distributed around 1.07 CV with some outliers present on either side and approaching 1.2 on the high side, see FIG. 17. The wash front shows slightly more variation and is centered at 0.99 CV with several low outliers approaching 0.8, see FIG. 22. It is recommended to apply control limits of 0.80 to 1.20 CV for the mean for both fronts (see Table 2). This is appropriate because the mean is not a measure of the column performance but is used as a check to ensure that the analysis was appropriate. The tighter control limits would result in unnecessary sensitivity for this check.

TABLE 2

Recommended HETP, SS, and Mean Control Limits for Protein A Column Purification during REMICADE ® (infliximab) Manufacturing

| Front | Parameter | UCL | LCL |
|---|---|---|---|
| Equlibration | HETP | 0.243 | 0.027 |
| | SS | 0.050 | NA |
| | Mean | 1.20 | 0.80 |
| Wash | HETP | 0.352 | 0.011 |
| | SS | 0.989 | NA |
| | Mean | 1.20 | 0.08 |

Example 2—Application of the Gamma Distribution Transition Analysis for Detection of Sub-Optimal Performance of Protein a Chromatography Columns Used in to REMICADE® (Infliximab) Manufacturing The manufacturing process of the therapeutic antibody, REMICADE® (infliximab), involves several stages, four of which involve chromatography purification. The gamma distribution transition analysis (GDTA) for column qualification was applied to two or three transitions during each of these column steps. This Example describes the application of the GDTA method to the Protein A column purification step employed REMICADE® (infliximab) manufacturing. The purification process includes two transition fronts, i.e., equilibration and intermediate wash, that are appropriate for GDTA as described herein.

The GDTA was executed on 45 Equilibration fronts from the consecutive purification of 45 batches of REMICADE® (infliximab), comprising 23 batches processed on column pack 883333M001 and 22 batches processed on column pack 885473M001. The gamma front distribution analysis was performed concurrently with manufacturing and did not impact the manufacturing process. All manufacturing, monitoring and controls were performed using current, effective procedures. During the column chromatography purification of REMICADE® (infliximab), conductivity (i.e., the column outlet signal) and flow of the eluent (i.e., accumulated flow) were recorded.

Figure 32:
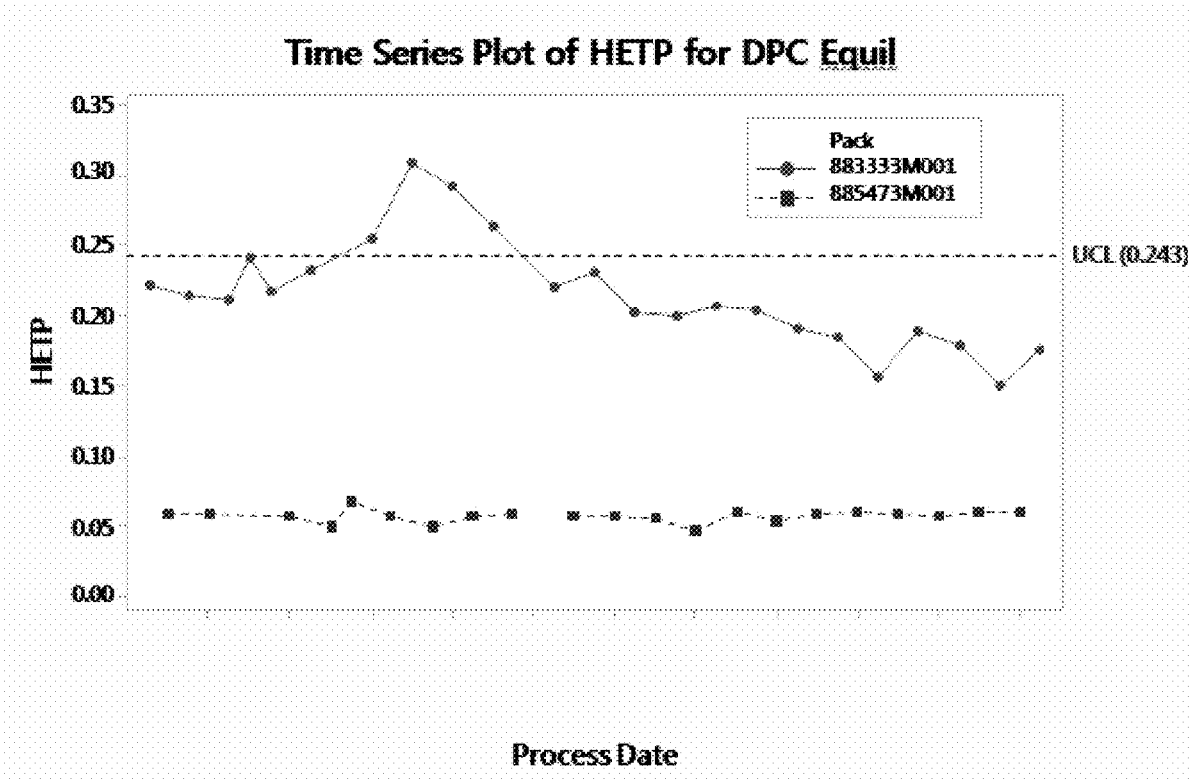
FIG. 32 is a time series plot of HETP for two different Protein A column packs as assessed over the equilibration front for 45 batches of REMICADE® (infliximab).

Trending of Equilibration HETP results for the 45 batches, see FIG. 32, showed a significant difference between column packs. Current controls for column evaluation did not identify any difference between the two column packs. Evaluation of the batch yield showed a significant ($p=0.001$) difference between the batches processed on the two column packs, estimated at 4.3% lower for the column pack with the higher HETP values. Other potential factors were evaluated and showed no correlation to the yield difference. Thus, the conclusion from this analysis is that the column performance difference caused lower yield. Based on this finding, the lower yielding column was conditioned to improve column packing before continued use. This example demonstrates the sensitivity of the GDTA method in assessing chromatography column quality.

Example 3—Application of the Gamma Distribution Transition Analysis for Column Qualification of SP-Sepharose High Performance Chromatography Columns Used in to REMICADE® (Infliximab) Manufacturing Overview:

As discussed above, the manufacturing process of REMICADE® (infliximab) involves several stages, four of which involve chromatography purification. This Example describes the application of the GDTA method to the SP-Sepharose High Performance (SPHP) column purification step employed REMICADE® (infliximab) manufacturing. The SPHP column is a cation exchange chromatography column. The purification process includes three transition fronts, i.e., equilibration, WFI flush, and storage fronts, that are appropriate for GDTA as described herein.

The GDTA was executed on 69 fronts from the purification of 23 batches of REMICADE® (infliximab), comprising 23 equilibration, WFI flush, and storage fronts. The gamma front distribution analysis was performed concurrently with manufacturing and did not impact the manufacturing process. All manufacturing, monitoring and controls were performed using current, effective procedures. During the column chromatography purification of REMICADE® (infliximab), conductivity (i.e., the column outlet signal) and flow of the eluent (i.e., accumulated flow) were recorded.

In addition to the application of the GDTA to column operation in real time, historical data for 189 transition fronts processed over the course of the four previous years was also collected and analyzed as described herein. The data set included 64 equilibration fronts, 63 WFI flush fronts, and 62 storage fronts. This data set was selected to provide an even distribution through the life of the columns and represents 6 column packs.

The GDTA for the SPHP column fronts was carried out as described in Example 1 above. This analysis produced measurements for HETP, SS and mean for each front. Control limits that were derived for each of these three parameters based on statistical evaluation are listed in Table 3 below.

Figure 33:
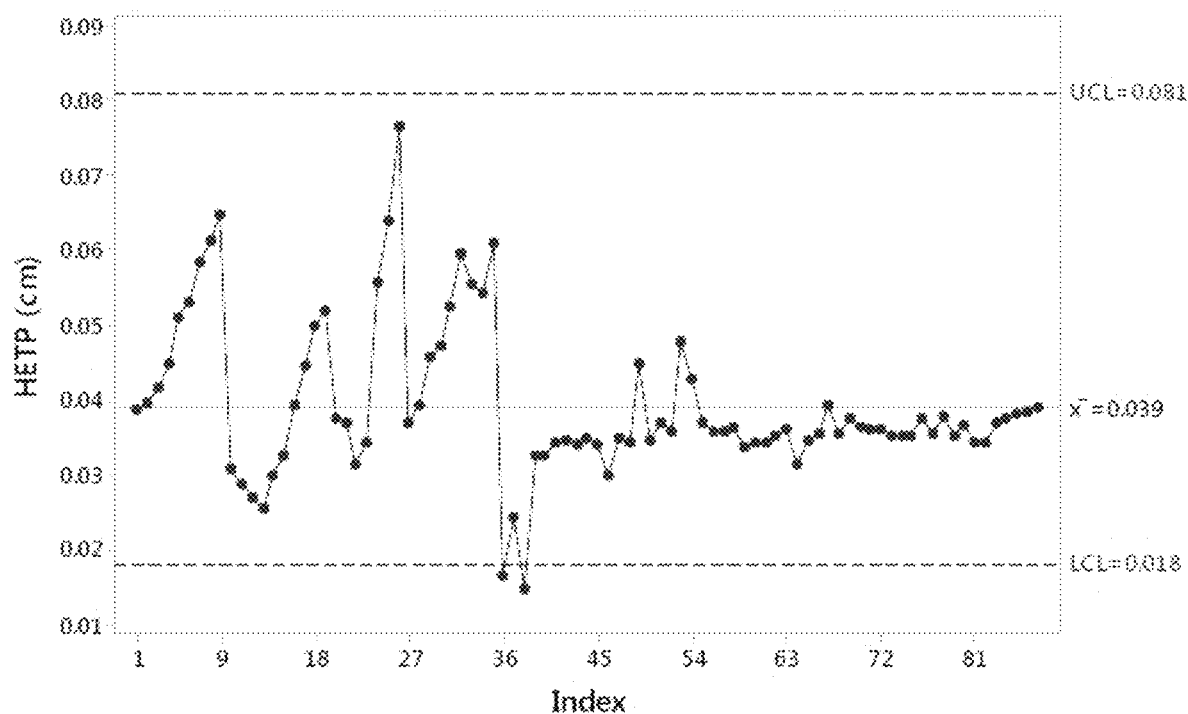
FIG. 33 is a time series plot of HETP for SP-Sepharose High Performance (SPHP) column equilibration front. Control limits are derived from the natural log Box-Cox transformation data.
Figure 34:
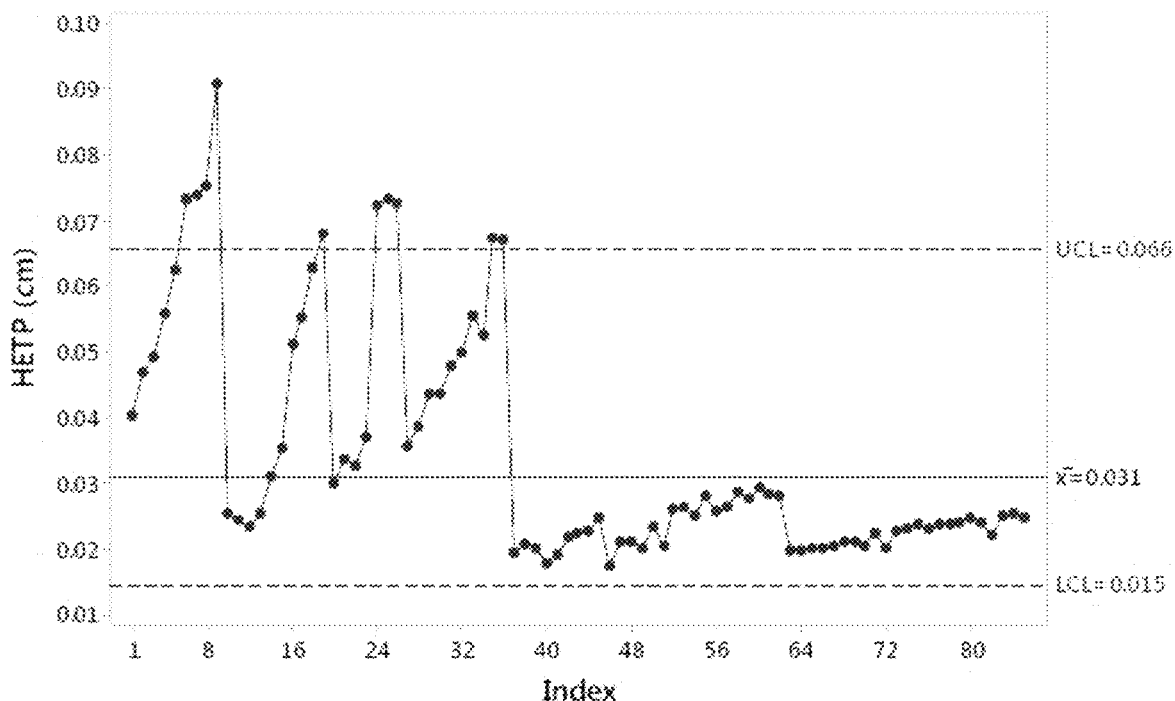
FIG. 34 is a time series plot of HETP for SPHP column WFI flush front. Control limits are derived from the natural log Box-Cox transformation data.
Figure 35:
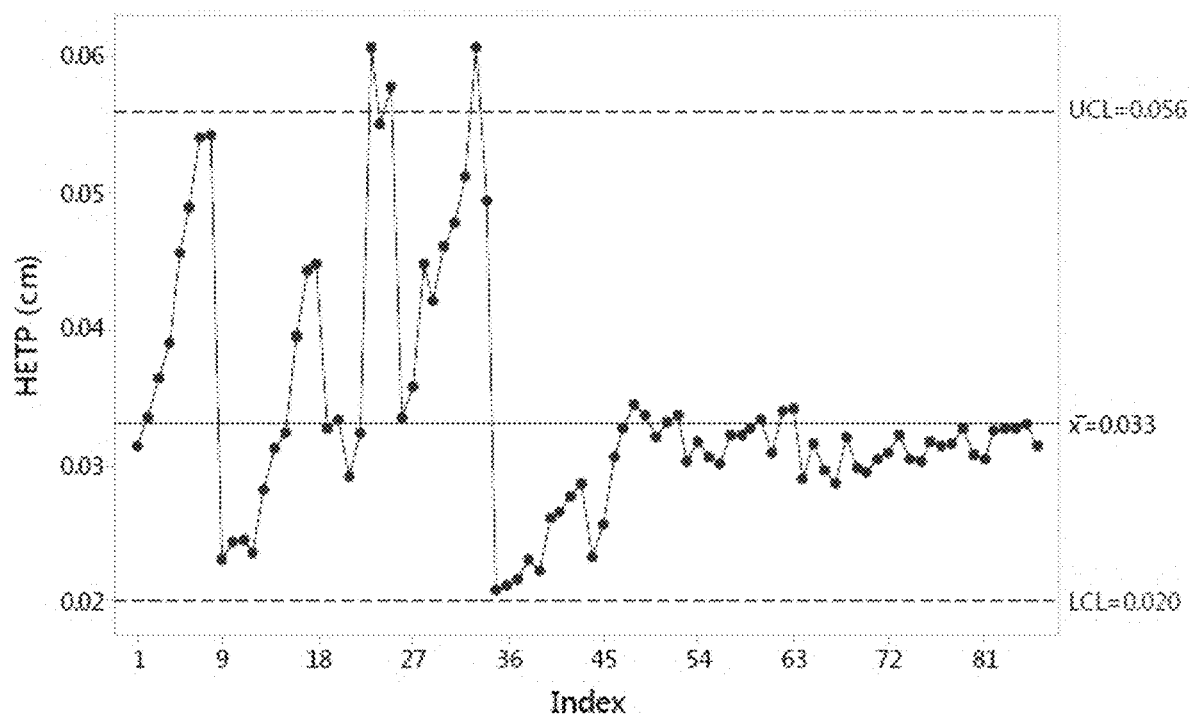
FIG. 35 is a time series plot of HETP for SPHP column storage front. Control limits are derived from the natural log Box-Cox transformation data.

Control Limits for SPHP Column:

HETP:

HETP is directly related to the column performance and is also affected by other factors in the system that may increase dispersion. The result must be >0. The control limits for HETP are best determined by using the natural log Box-Cox transformation ($\lambda=0$). The control limits for the transformed data were calculated by Minitab using the mean +/−3 standard deviations. Standard deviation is determined based on the average moving range. A moving range of 25 was selected to account for the variation in column performance over the column life. The upper and lower control limits are reverse transformed (ex) to determine the control limits for the untransformed data. A time series plot for each front's HETP results and control limits is shown in FIG. 33 (equilibration front), FIG. 34 (WFI flush front), and FIG. 35 (storage front). Operation within these limits is expected to produce acceptable chromatographic performance based on this historical review. Values above the upper control limits may indicate column flow issues and should be evaluated further. Values below the lower control limits may be indicative of a calculation error.

Sum of Squares (SS):

The SS is a measure of how well the gamma distribution model fits the data. This measure will be used to ensure that HETP values calculated using the GDTA method represent the process data. There is no lower limit and the result must be >0. The upper control limit for SS is best determined by using the natural log Box-Cox transformation ($\lambda=0$). The control limits for the transformed data was calculated by Minitab using the mean +/−3 standard deviations. Standard deviation is determined based on the average moving range. A moving range of 100 was selected to account for the variation in column performance over the column life. The upper control limits for the transformed data were reverse transformed to give 0.110 for the equilibration front, 0.027 for the WFI flush front, and 0.073 for the storage front (see Table 3). Results within the limits will ensure that the model fits the data as well as historical results. If the result is outside of this range, a special cause is likely.

Mean:

The mean was added as a second measure of the accuracy of the gamma distribution model. The mean represents the theoretical center of mass for the front and should always be near 1 column volume unless there are other factors in the system that cause it to shift, such as large extra column volume or interaction between the mobile phase and resin. The mean values for equilibration, WFI flush and storage fronts have an irregular distribution and do not benefit from transformation. It is recommended to apply control limits of 0.80 to 1.20 CV for the mean for each of the fronts (see Table 3). This is appropriate because the mean is not a measure of the column performance but is used as a check to ensure that the analysis was appropriate. These limits are expected to be sufficient to identify significant departures from the expected calculation results. Tighter control limits would result in unnecessary sensitivity for this check, which is seen to vary with each column pack.

TABLE 3

Recommended HETP, SS, and Mean Control Limits for SPHP Column Purification during REMICADE ® (infliximab) Manufacturing

| Front | Parameter | UCL | LCL |
| --- | --- | --- | --- |
| Equilibration | HETP | 0.081 | 0.018 |
| | SS | 0.110 | NA |
| | Mean | 1.20 | 0.80 |
| WFI Flush | HETP | 0.066 | 0.015 |
| | SS | 0.027 | NA |
| | Mean | 1.20 | 0.80 |
| Wash | HETP | 0.056 | 0.020 |
| | SS | 0.073 | NA |
| | Mean | 1.20 | 0.80 |

Example 4—Application of the Gamma Distribution Transition Analysis for Column Qualification of Q2 Chromatography Columns Used in to REMICADE® (Infliximab) Manufacturing Overview:

This Example describes the application of the GDTA method to the Secondary Anion Exchange (Q2) column purification step employed REMICADE® (infliximab) manufacturing. The Q2 column is an anion exchange chromatography column. The purification process includes three transition fronts, i.e., equilibration, strip, and storage fronts, which are appropriate for GDTA as described herein.

The GDTA was executed on 68 fronts, comprising 23 equilibration and strip fronts, and 22 storage fronts. The gamma front distribution analysis was performed concurrently with manufacturing and did not impact the manufacturing process. All manufacturing, monitoring and controls were performed using current, effective procedures. During the column chromatography purification of REMICADE® (infliximab), conductivity (i.e., the column outlet signal) and flow of the eluent (i.e., accumulated flow) were recorded.

In addition to the application of the GDTA to column operation in real time, historical data for 324 transition fronts processed over the course of the four previous years was also collected and analyzed as described herein. The data set included 121 equilibration fronts, 124 strip fronts, and 79 storage fronts. This data set was selected to provide an even distribution through the life of the columns and represents 10 column packs.

The GDTA for the Q2 column fronts was carried out as described in Example 1 above. This analysis produced measurements for HETP, SS and mean for each front. Control limits that were derived for each of these three parameters based on statistical evaluation listed in Table 4 below.

Control Limits for Q2 Column:

HETP:

HETP is directly related to the column performance and is also affected by other factors in the system that may increase dispersion. The result must be >0. The control limits for HETP are best determined by using the natural log Box-Cox transformation ($\lambda=0$). The control limits for the transformed data were calculated by Minitab using the mean +/−3 standard deviations. Standard deviation is determined based on the average moving range. A moving range of 100 was selected to account for the variation in column performance over the column life. The upper and lower control limits are reverse transformed (ex) to determine the control limits for the untransformed data.

Figure 36:
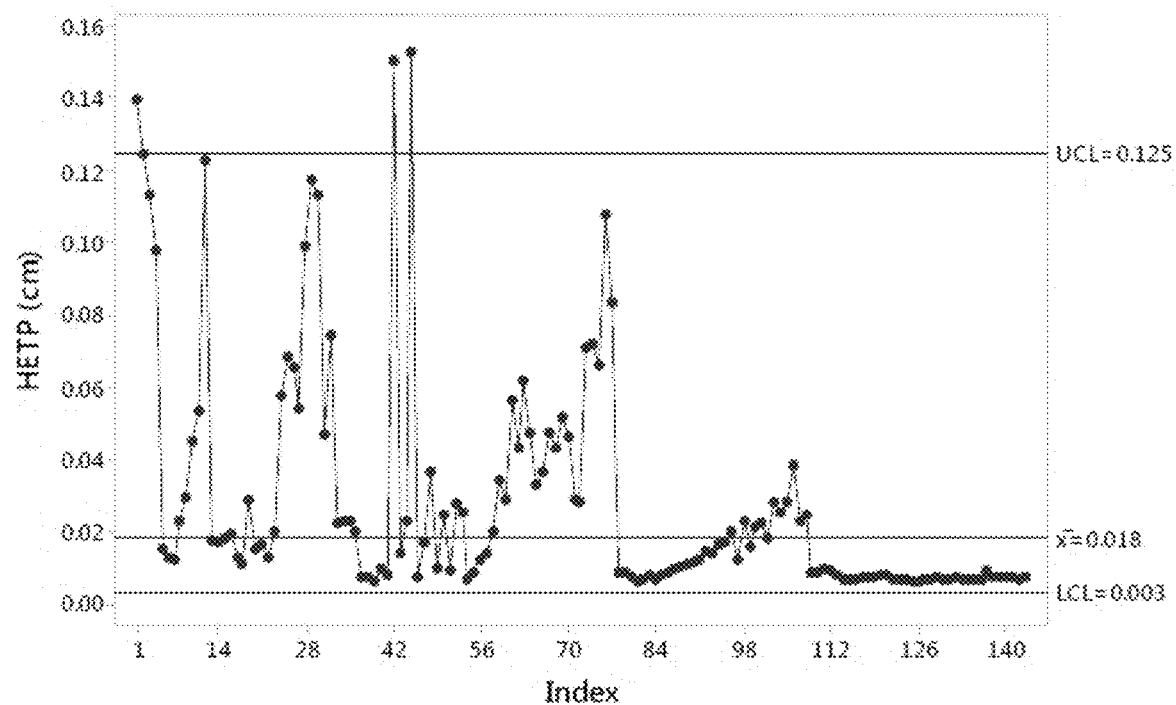
FIG. 36 is a time series plot of HETP for Q2 column equilibration front. Control limits are derived from the natural log Box-Cox transformation data.
Figure 37:
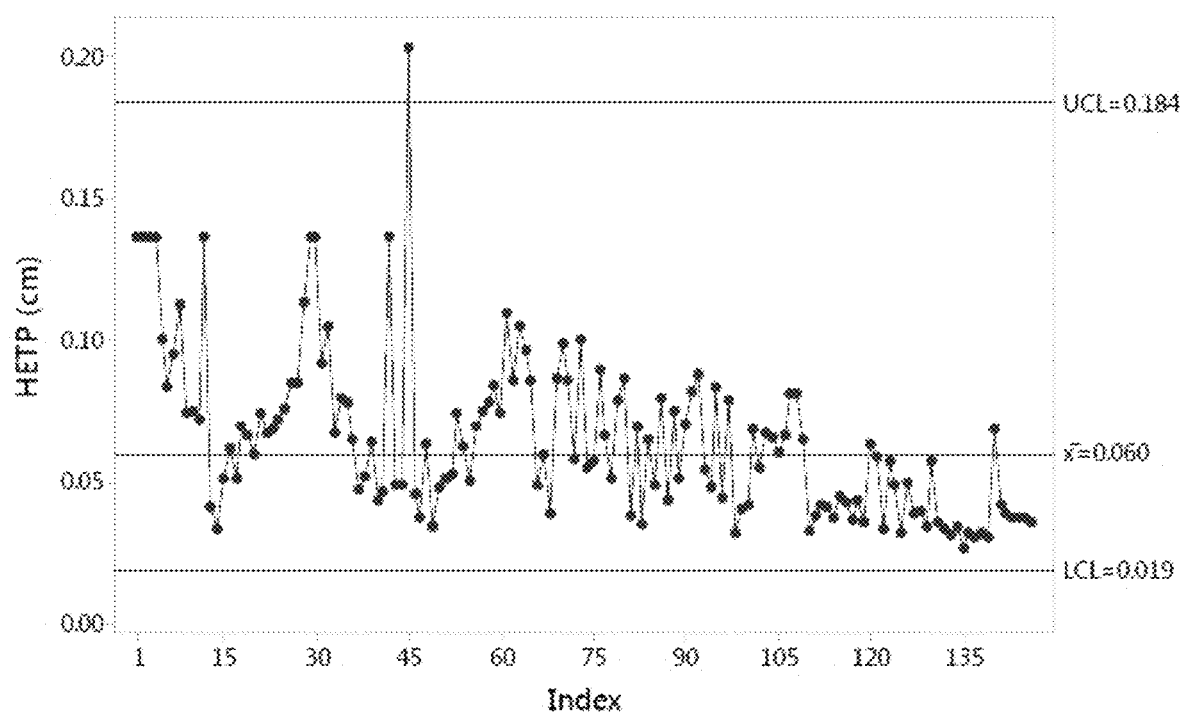
FIG. 37 is a time series plot of HETP for Q2 column strip equilibration front. Control limits are derived from the natural log Box-Cox transformation data.
Figure 38:
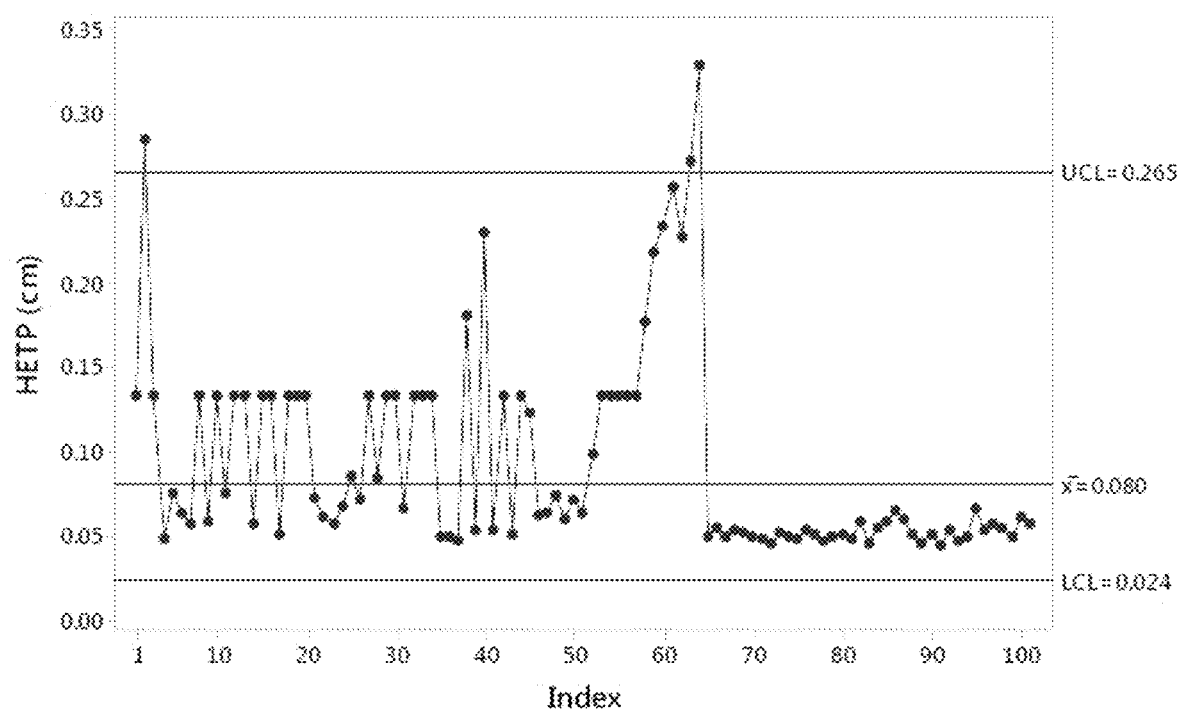
FIG. 38 is a time series plot of HETP for Q2 column storage front. Control limits are derived from the natural log Box-Cox transformation data.

A time series plot for each front's HETP results and control limits is shown in FIG. 36 (equilibration front), FIG. 37 (strip front), and FIG. 38 (storage front). Operation within these limits is expected to produce acceptable chromatographic performance based on this historical review. Values above the upper control limits may indicate column flow issues and should be evaluated further. Values below the lower control limits may be indicative of a calculation error.

Sum of Squares (SS):

The SS is a measure of how well the gamma distribution model fits the data. This measure will be used to ensure that HETP values calculated using the GDTA method represent the process data. There is no lower limit and the result must be >0. The upper control limit for SS is best determined by using the natural log Box-Cox transformation ($\lambda=0$). The control limits for the transformed data were calculated by Minitab using the mean +/−3 standard deviations. Standard deviation is determined based on the average moving range. A moving range of 100 was selected to account for the variation in column performance over the column life. The standard deviation was determined from the aggregate data for the Storage front, as the moving range method produced a higher standard deviation. The control limits are reported in Table 4 below. Results within the limits will ensure that the model fits the data as well as historical results. If the result is outside of this range, a special cause is likely.

Mean:

The mean was added as a second measure of the accuracy of the gamma distribution model. The mean represents the theoretical center of mass for the front and should always be near 1 column volume unless there are other factors in the system that cause it to shift, such as large extra column volume or interaction between the mobile phase and resin. The mean values for equilibration, strip, and storage fronts have an irregular distribution and do not benefit from transformation. It is recommended to apply control limits of 0.80 to 1.20 CV for the mean for each of the fronts (see Table 4). This is appropriate because the mean is not a measure of the column performance but is used as a check to ensure that the analysis was appropriate. These limits are expected to be sufficient to identify significant departures from the expected calculation results. Tighter control limits would result in unnecessary sensitivity for this check, which is seen to vary with each column pack.

TABLE 4

Recommended HETP, SS, and Mean Control Limits for Q2 Column Purification during REMICADE ® (infliximab) Manufacturing

| Front | Parameter | UCL | LCL |
|---|---|---|---|
| Equilibration | HETP | 0.125 | 0.003 |
| | SS | 0.344 | NA |
| | Mean | 1.20 | 0.80 |
| Strip | HETP | 0.184 | 0.019 |
| | SS | 0.156 | NA |
| | Mean | 1.20 | 0.80 |
| Wash | HETP | 0.265 | 0.024 |
| | SS | 0.691 | NA |
| | Mean | 1.20 | 0.80 |

Example 5—Manufacturing Processes to Produce STELARA® (Ustekinumab)

Background

STELARA® (ustekinumab) is a fully human G1 kappa monoclonal antibody that binds with high affinity and specificity to the shared p40 subunit of human interleukin (IL)-12 and IL-23 cytokines. Ustekinumab comprises a heavy chain of the amino acid sequence of SEQ ID NO:10 and a light chain of the amino acid sequence of SEQ ID NO:11; a heavy chain variable domain amino acid sequence of SEQ ID NO:7 and a light chain variable domain amino acid sequence of SEQ ID NO:8; the heavy chain CDR amino acid sequences of SEQ ID NO:1, SEQ ID NO:2, and SEQ ID NO:3; and the light chain CDR amino acid sequences of SEQ ID NO:4, SEQ ID NO:5, and SEQ ID NO:6. The binding of ustekinumab to the IL-12/23p40 subunit blocks the binding of IL-12 or IL-23 to the IL-12R131 receptor on the surface of natural killer and CD4$^+$ T cells, inhibiting IL-12- and IL-23-specific intracellular signaling and subsequent activation and cytokine production. Abnormal regulation of IL-12 and IL-23 has been associated with multiple immune-mediated diseases.

To date, ustekinumab has received marketing approval globally, including countries in North America, Europe, South America, and the Asia-Pacific region, for the treatment of adult patients including those with chronic moderate to severe plaque psoriasis and/or active psoriatic arthritis, and Crohn's disease (CD). Ustekinumab is also being evaluated in a Phase 3 study for the treatment of active Systemic Lupus Erythematosus (SLE).

Sequences

Example Anti-IL-12/IL-23p40 Antibody Sequences—STELARA® (Ustekinumab)

Amino acid sequence of anti-IL-12/IL-23p40 antibody complementarity determining region heavy chain 1 (CDRH1): (SEQ ID NO:1)

```
TYWLG
```

Amino acid sequence of anti-IL-12/IL-23p40 antibody complementarity determining region heavy chain 2 (CDRH2): (SEQ ID NO:2)

```
IMSPVDSDIRYSPSFQG
```

Amino acid sequence of anti-IL-12/IL-23p40 antibody complementarity determining region heavy chain 3 (CDRH3): (SEQ ID NO:3)

```
RRPGQGYFDF
```

Amino acid sequence of anti-IL-12/IL-23p40 antibody complementarity determining region light chain 1 (CDRL1): (SEQ ID NO:4)

```
RASQGISSWLA
```

Amino acid sequence of anti-IL-12/IL-23p40 antibody complementarity determining region light chain 2 (CDRL2): (SEQ ID NO:5)

```
AASSLQS
```

Amino acid sequence of anti-IL-12/IL-23p40 antibody complementarity determining region light chain 3 (CDRL3): (SEQ ID NO:6)

```
QQYNIYPYT
```

Amino acid sequence of anti-IL-12/IL-23p40 antibody variable heavy chain region (CDRs underlined): (SEQ ID NO:7)

```
  1 EVQLVQSGAE VKKPGESLKI SCKGSGYSFT TYWLGWVRQM
    PGKGLDWIGI MSPVDSDIRY

61 SPSFQGQVTM SVDKSITTAY LQWNSLKASD TAMYYCARRR
    PGQGYFDFWG QGTLVTV SS
```

Amino acid sequence of anti-IL-12/IL-23p40 antibody variable light chain region (CDRs underlined): (SEQ ID NO:8)

```
  1 DIQMTQSPSS LSASVGDRVT ITCRASQGIS SWLAWYQQKP
    EKAPKSLIYA ASSLQSGVPS

61 RFSGSGSGTD FTLTISSLQP EDFATYYCQQ YNIYPYTFGQ
    GTKLEIKR
```

Amino acid sequence of anti-IL-12/IL-23p40 antibody heavy chain (CDRs underlined): (SEQ ID NO:10)

```
  1  EVQLVQSGAE VKKPGESLKI SCKGSGYSFT TYWLGWVRQM
     PGKGLDWIGI MSPVDSDIRY

61  SPSFQGQVTM SVDKSITTAY LQWNSLKASD TAMYYCARRR
     PGQGYFDFWG QGTLVTVSSS

121  STKGPSVFPL APSSKSTSGG TAALGCLVKD YFPEPVTVSW
     NSGALTSGVH TFPAVLQSSG

181  LYSLSSVVTV PSSSLGTQTY ICNVNHKPSN TKVDKRVEPK
     SCDKTHTCPP CPAPELLGGP

241  SVFLFPPKPK DTLMISRTPE VTCVVVDVSH EDPEVKFNWY
     VDGVEVHNAK TKPREEQYNS

301  TYRVVSVLTV LHQDWLNGKE YKCKVSNKAL PAPIEKTISK
     AKGQPREPQV YTLPPSRDEL

361  TKNQVSLTCL VKGFYPSDIA VEWESNGQPE NNYKTTPPVL
     DSDGSFFLYS KLTVDKSRWQ

421  QGNVFSCSVM HEALHNHYTQ KSLSLSPGK
```

Amino acid sequence of anti-IL-12/IL-23p40 antibody light chain (CDRs underlined): (SEQ ID NO:11)

```
  1  DIQMTQSPSS LSASVGDRVT ITCRASQGIS SWLAWYQQKP
     EKAPKSLIYA ASSLQSGVPS

61  RFSGSGSGTD FTLTISSLQP EDFATYYCQQ YNIYPYTFGQ
     GTKLEIKRTV AAPSVFIFPP

121  SDEQLKSGTA SVVCLLNNFY PREAKVQWKV DNALQSGNSQ
     ESVTEQDSKD STYSLSSTLT

181  LSKADYEKHK VYACEVTHQG LSSPVTKSFN RGEC
```

Amino Acid Sequence IL-12

Amino acid sequence of human interleukin (IL)-12 with alpha and beta subunits: (SEQ ID NO:9)

```
  1  RNLPVATPDP GMFPCLHHSQ NLLRAVSNML QKARQTLEFY
     PCTSEEIDHE DITKDKTSTV

61  EACLPLELTK NESCLNSRET SFITNGSCLA SRKTSFMMAL
     CLSSIYEDLK MYQVEFKTMN

121  AKLLMDPKRQ IFLDQNMLAV IDELMQALNF NSETVPQKSS
     LEEPDFYKTK IKLCILLHAF

181  RIRAVTIDRV MSYLNASIWE LKKDVYVVEL DWYPDAPGEM
     VVLTCDTPEE DGITWTLDQS

241  SEVLGSGKTL TIQVKEFGDA GQYTCHKGGE VLSHSLLLLH
     KKEDGIWSTD ILKDQKEPKN

301  KTFLRCEAKN YSGRFTCWWL TTISTDLTFS VKSSRGSSDP
     QGVTCGAATL SAERVRGDNK

361  EYEYSVECQE DSACPAAEES LPIEVMVDAV HKLKYENYTS
     SFFIRDIIKP DPPKNLQLKP

421  LKNSRQVEVS WEYPDTWSTP HSYFSLTFCV QVQGKSKREK
     KDRVFTDKTS ATVICRKNAS

481  ISVRAQDRYY SSSWSEWASV PCS
```

Recombinant Expression Cassettes

The present invention uses recombinant expression cassettes comprising a nucleic acid. A nucleic acid sequence, for example, a cDNA or a genomic sequence encoding an antibody used in the method of the present invention, can be used to construct a recombinant expression cassette that can be introduced into at least one desired host cell. A recombinant expression cassette will typically comprise a polynucleotide operably linked to transcriptional initiation regulatory sequences that will direct the transcription of the polynucleotide in the intended host cell. Both heterologous and non-heterologous (i.e., endogenous) promoters can be employed to direct expression of the nucleic acids.

In some embodiments, isolated nucleic acids that serve as promoter, enhancer, or other elements can be introduced in the appropriate position (upstream, downstream or in the intron) of a non-heterologous form of a polynucleotide of the present invention so as to up or down regulate expression of a polynucleotide. For example, endogenous promoters can be altered in vivo or in vitro by mutation, deletion and/or substitution.

Vectors and Host Cells

The present invention also relates to vectors that include isolated nucleic acid molecules, host cells that are genetically engineered with the recombinant vectors, and the production of at least one anti-IL-23 antibody by recombinant techniques, as is well known in the art.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS) (U.S. Pat. Nos. 5,122,464; 5,770,359; 5,827,739) resistance for eukaryotic cell culture, and tetracycline or ampicillin resistance genes for culturing in *E. coli* and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be affected by calcium phosphate transfection, DEAE-dextran mediated transfection, cationic lipid-mediated transfection, electroporation, transduction, infection or other known methods. Such methods are well-known and well-described in the art.

At least one antibody used in the method of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, and the methods are well-known and well-described in the art.

Those of ordinary skill in the art are knowledgeable in the numerous expression systems available for expression of a nucleic acid encoding a protein used in the method of the present invention. Alternatively, nucleic acids can be expressed in a host cell by turning on (by manipulation) in a host cell that contains endogenous DNA encoding an antibody. Such methods are well known in the art, e.g., as described in U.S. Pat. Nos. 5,580,734, 5,641,670, 5,733,746, and 5,733,761.

Cells useful for the production of the antibodies, specified portions or variants thereof, include mammalian cells. Mammalian cell systems often will be cultured in the form of monolayers of cells, but the cells can also be adapted to grow in suspension, e.g., in shake flasks or bioreactors. A number of suitable host cell lines capable of expressing intact glycosylated proteins have been developed in the art, and include, e.g., COS-1 (e.g., ATCC® CRL1650), COS-7 (e.g., ATCC® CRL-1651), HEK293, BHK21 (e.g., ATCC® CCL-10), BSC-1 (e.g., ATCC® CCL-26), Chinese hamster ovary (CHO), Hep G2, P3X63Ag8.653, Sp2/0-Ag14, HeLa and the like, which are readily available from, for example, American Type Culture Collection, Manassas, Va (www.atcc.org). In certain embodiments, host cells include CHO cells and cells of lymphoid origin, such as myeloma and lymphoma cells, e.g., CHO-K1 cells, P3X63Ag8.653 cells (ATCC® CRL-1580) and Sp2/0-Ag14 cells (ATCC® CRL-1581).

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., "Expression of a recombinant DNA gene coding for the vesicular stomatitis virus nucleocapsid protein." *J. Virol.* 45:773-781 (1983)). Additionally, gene sequences to control replication in the host cell can be incorporated into the vector, as known in the art.

CHO Cell Lines

Despite the availability of several other mammalian cell lines, a majority of recombinant therapeutic proteins produced today are made in Chinese hamster ovary (CHO) cells (Jayapal K P, et al. Recombinant protein therapeutics from CHO cells-20 years and counting. *Chem Eng Prog.* 2007; 103:40-47; Kunert R, Reinhart D. Advances in recombinant antibody manufacturing. *Appl Microbiol Biotechnol.* 2016; 100(8):3451-61). Their strengths include, e.g., robust growth as adherent cells or in suspension, adaptability to serum-free and chemically defined media, high productivity, and an established history of regulatory approval for therapeutic recombinant protein production. They are also very amenable to genetic modifications and the methods for cell transfection, recombinant protein expression, and clone selection are all well characterized. CHO cells can also provide human-compatible post-translational modifications. As used herein, "CHO cells" include, but are not limited to, e.g., CHO-DG44, CHO-K1, CHO-M, CHO-S, CHO GS knockout, and modifications and derivatives thereof.

Cloning and Expression in CHO Cells.

One vector commonly used for expression in CHO cells is pC4. Plasmid pC4 is a derivative of the plasmid pSV2-dhfr (ATCC® 37146). The plasmid contains the mouse DHFR gene under control of the SV40 early promoter. Chinese hamster ovary cells or other cells lacking dihydrofolate activity that are transfected with these plasmids can be selected by growing the cells in a selective medium (e.g., alpha minus MEM, Life Technologies, Gaithersburg, MD) supplemented with the chemotherapeutic agent methotrexate. The amplification of the DHFR genes in cells resistant to methotrexate (MTX) has been well documented (see, e.g., F. W. Alt, et al., "Selective multiplication of dihydrofolate reductase genes in methotrexate-resistant variants of cultured murine cells." *J. Biol. Chem.* 253:1357-1370 (1978); and M. J. Page and M. A. Sydenham, "High level expression of the humanized monoclonal antibody Campath-1H in Chinese hamster ovary cells." *Biotechnology* 9:64-68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach can be used to develop cell lines carrying more than 1,000 copies of the amplified gene(s). Subsequently, when the methotrexate is withdrawn, cell lines are obtained that contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., "Functional analysis of the transcription control region located within the avian retroviral long terminal repeat." Mol. Cell. Biol. 5:438-447 (1985)) plus a fragment isolated from the enhancer of the immediate early gene of human cytomegalovirus (CMV) (Boshart, et al., "A very strong enhancer is located upstream of an immediate early gene of human cytomegalovirus." Cell 41:521-530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human beta-actin promoter, the SV40 early or late promoters or the long terminal repeats from other retroviruses, e.g., HIV and HTLVI. Clontech's Tet-Off and Tet-On gene expression systems and similar systems can also be used to express proteins in a regulated way in mammalian cells (M. Gossen, and H. Bujard, "Tight control of gene expression in mammalian cells by tetracycline-responsive promoters." *Proc. Natl. Acad. Sci. USA* 89: 5547-5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

General Purification Methods

An anti-IL-12/IL-23p40 or IL-23 antibody can be recovered and purified from recombinant cell cultures by well-known methods including, but not limited to, e.g., protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification.

As used herein, the terms "antibody" or "antibodies", include biosimilar antibody molecules approved under the Biologics Price Competition and Innovation Act of 2009 (BPCI Act) and similar laws and regulations globally. Under the BPCI Act, an antibody may be demonstrated to be biosimilar if data show that it is "highly similar" to the reference product notwithstanding minor differences in clinically inactive components and are "expected" to produce the same clinical result as the reference product in terms of safety, purity and potency (R. Dolinar, F. Lavernia, and S. Edelman. "A GUIDE TO FOLLOW-ON BIOLOGICS AND BIOSIMILARS WITH A FOCUS ON INSULIN." *Endocrine Practice*: February 2018, Vol. 24, No. 2, pp. 195-204). These biosimilar antibody molecules are provided an abbreviated approval pathway, whereby the applicant relies upon the innovator reference product's clinical data to secure regulatory approval. Compared to the original innovator reference antibody that was FDA approved based on successful clinical trials, a biosimilar antibody molecule is referred to herein as a "follow-on biologic". As presented herein, STELARA® (ustekinumab) is the original innovator reference anti-IL-12/23p40 antibody that was FDA approved based on successful clinical trials. Ustekinumab has been on sale in the United States since 2009.

As used herein, the term "antigen-binding fragment" refers to an antibody fragment such as, for example, a diabody, a Fab, a Fab', a F(ab')2, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), a single domain antibody (sdab) an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment (i.e., portion of the heavy chain which is included in the Fab fragment). According to other particular embodiments, the antigen-binding fragment comprises Fab and F(ab').

Manufacturing Process Overview

Figure 39:
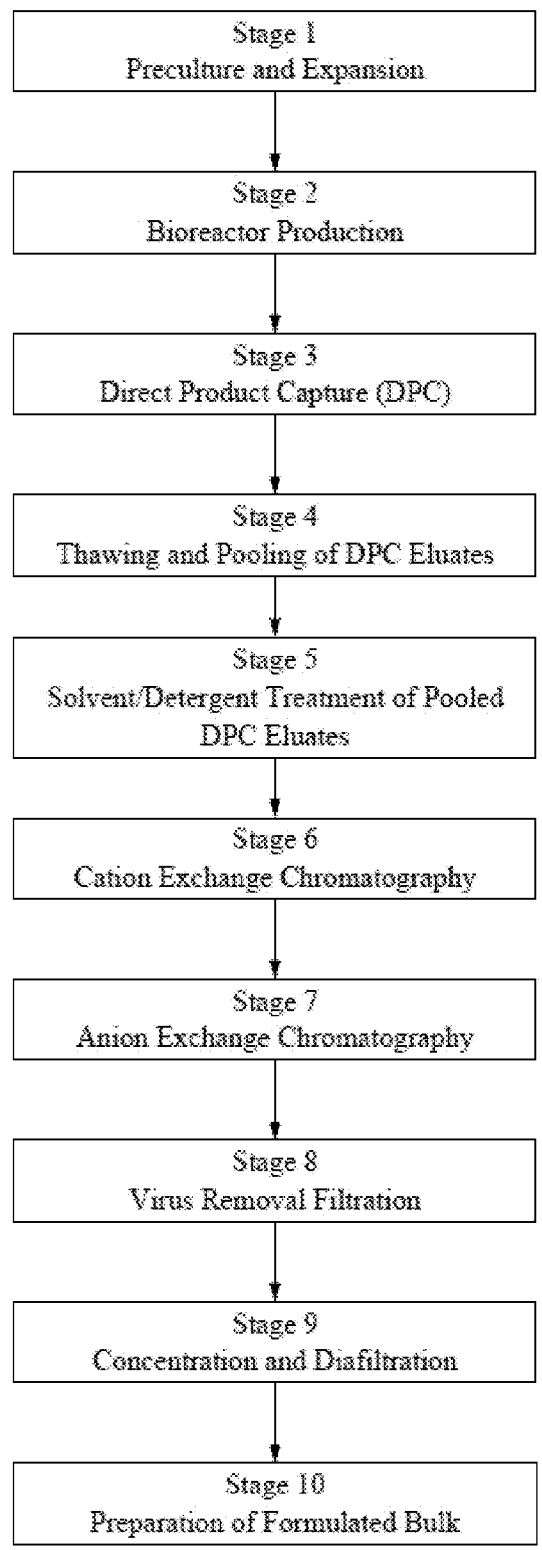
FIG. 39 shows an overview of the 10 stages of the ustekinumab manufacturing process.

STELARA® (ustekinumab) is manufactured in a 10-stage process that includes continuous perfusion cell culture followed by purification. An overview of the manufacturing process is provided in FIG. 39.

As used herein, the terms "culture", "culturing", "cultured", and "cell culture" refer to a cell population that is suspended in a medium under conditions suitable to survival and/or growth of the cell population. As will be clear from context to those of ordinary skill in the art, these terms as used herein also refer to the combination comprising the cell population and the medium in which the population is suspended. Cell culture includes, e.g., cells grown by batch, fed-batch or perfusion cell culture methods and the like. In certain embodiments, the cell culture is a mammalian cell culture.

Cell lines for use in the present invention include mammalian cell lines including, but not limited to, Chinese Hamster Ovary cells (CHO cells), human embryonic kidney cells (HEK cells), baby hamster kidney cells (BHK cells), mouse myeloma cells (e.g., NS0 cells and Sp2/0 cells), and human retinal cells (e.g., PER.C6 cells).

As used herein, the terms "chemically defined medium", "chemically defined media", "chemically defined hybridoma medium", or "chemically defined hybridoma media" refer to a synthetic growth medium in which the identity and concentration of all the components are known. Chemically defined media do not contain bacterial, yeast, animal, or plant extracts, animal serum or plasma although they may or may not include individual plant or animal-derived components (e.g., proteins, polypeptides, etc). Chemically defined media may contain inorganic salts such as phosphates, sulfates, and the like needed to support growth. The carbon source is defined, and is usually a sugar such as glucose, lactose, galactose, and the like, or other compounds such as glycerol, lactate, acetate, and the like. While certain chemically defined media also use phosphate salts as a buffer, other buffers may be employed such as citrate, triethanolamine, and the like. Examples of commercially available chemically defined media include, but are not limited to, ThermoFisher's CD Hybridoma Medium and CD Hybridoma AGT™ Medium, various Dulbecco's Modified Eagle's (DME) mediums (Sigma-Aldrich Co; SAFC Biosciences, Inc), Ham's Nutrient Mixture (Sigma-Aldrich Co; SAFC Biosciences, Inc), combinations thereof, and the like. Methods of preparing chemically defined mediums are known in the art, for example in U.S. Pat. Nos. 6,171,825 and 6,936,441, WO 2007/077217, and U.S. Pat. App. Pub. Nos. 2008/0009040 and 2007/0212770.

The term "bioreactor" as used herein refers to any vessel useful for the growth of a cell culture. The bioreactor can be of any size so long as it is useful for the culturing of cells. In certain embodiments, such cells are mammalian cells. Typically, the bioreactor will be at least 1 liter and may be 10, 100, 250, 500, 1,000, 2,500, 5,000, 8,000, 10,000, 12,000 liters or more, or any volume in between. The internal conditions of the bioreactor, including, but not limited to pH and temperature, are optionally controlled during the culturing period. The bioreactor can be composed of any material that is suitable for holding mammalian cell cultures suspended in media under the culture conditions of the present invention, including glass, plastic or metal. The term "production bioreactor" as used herein refers to the final bioreactor used in the production of the polypeptide or glycoprotein of interest. The volume of the production bioreactor is typically at least 500 liters and may be 1,000, 2,500, 5,000, 8,000, 10,000, 12,000 liters or more, or any volume in between. One of ordinary skill in the art will be aware of and will be able to choose suitable bioreactors for use in practicing the present invention.

Preculture, expansion, and production of ustekinumab are performed in Stage 1 and Stage 2. In Stage 1, preculture is initiated from one or more working cell bank vials of transfected Sp2/0 cells expressing the HC and LC sequences of ustekinumab and expanded in culture flasks, disposable culture bags, and a 100 L seed bioreactor. The cells are cultured until the cell density and volume required for inoculation of a 500 L production bioreactor are obtained. In Stage 2, the cell culture is perfused in a 500 L production bioreactor using an alternating tangential flow (ATF) hollow fiber filter cell retention system. Cell culture permeate (harvest) is collected from the ATF system while cells are retained within the bioreactor and the culture is replenished with fresh medium. Harvest from one or more 500 L production bioreactors may be combined in Stage 3. The harvests are purified using Mab Select Protein A resin affinity chromatography. The resultant direct product capture (DPC) eluate is frozen until further processing.

Purification of ustekinumab from DPC is performed in Stage 4 through Stage 8 by ion exchange chromatography steps and other steps to inactivate or remove potential virus contamination (solvent/detergent [S/D] treatment and virus removal filtration). DPC eluates are thawed, pooled and filtered in Stage 4 and incubated with Tri-n-butyl Phosphate (TNBP) and polysorbate 80 S/D treatment in Stage 5 to inactivate any lipid-enveloped viruses present. TNBP and polysorbate 80 reagents, aggregates, and impurities are removed from ustekinumab in Stage 6, using SPXL® sepharose cation exchange resin chromatography. Ustekinumab is further purified using QXL® sepharose anion exchange resin chromatography in Stage 7 to remove DNA, viruses, and impurities. In Stage 8, the purified ustekinumab is diluted and filtered through a virus retentive filter (NFP®).

Preparation of the ustekinumab pre-formulated bulk (PFB) and formulated bulk (FB) is performed in Stages 9 and 10, respectively. In Stage 9, the ultrafiltration step concentrates the ustekinumab and the diafiltration step adds the formulation excipients and removes the in-process buffer salts. Polysorbate 80 is added to the ustekinumab PFB in Stage 10 to obtain the FB. The FB is filtered into polycarbonate containers for frozen storage. The frozen FB is packaged in insulated containers with dry ice for transport to the drug product manufacturing site.

Detailed Description of Large-Scale Manufacturing Process
Stage 1—Preculture and Expansion The first stage in the production of ustekinumab is the initiation of preculture from a Working Cell Bank (WCB) vial of transfected Sp2/0 cells expressing the HC and LC sequences of ustekinumab and expanded in culture flasks, disposable culture bags, and a 100 L seed bioreactor. The cells are cultured until the cell density and volume required for inoculation of a 500 L production bioreactor are obtained.

Manufacturing Procedure

One or more cryopreserved vials of WCB are thawed and diluted with CD (chemically defined) hybridoma medium supplemented with 6 mM L-glutamine, 0.5 mg/L mycophenolic acid, 2.5 mg/L hypoxanthine, and 50 mg/L xanthine (CDH-A). The culture viability must be >45%. The cells are further diluted with CDH-A in a culture flask to a seeding density of 0.2 to $0.5 \times 10^6$ viable cells (VC)/mL. The preculture is maintained in a humidified CO2 incubator, with temperature, CO2 concentration, and agitation controlled within ranges defined in the batch record. The preculture is incubated for ≤3 days until a minimum cell density of $\geq 0.6 \times 10^6$ VC/mL and a culture viability of >50% are obtained. The preculture is expanded sequentially in a series of culture flasks and then culture bags as a mechanism to scale up for inoculation of the 100 L seed bioreactor. During the culture expansion phase, each incubation step takes ≤3 days to achieve passage conditions, which require a cell density of $>0.6 \times 10^6$ VC/mL and a culture viability of >80%. The seeding density for each passage is 0.2 to $0.5 \times 10^6$ VC/mL in culture flasks, and 0.2 to $0.6 \times 10^6$ VC/mL in culture bags. Each passage is sampled for viable cell density (VCD), culture viability, and microscopic examination. Prior to inoculation of the 100 L seed bioreactor, the preculture is sampled for bioburden.

Preculture expansions may be maintained for a maximum of 30 days post-thaw. Precultures not used within 30 days are discarded. Back-up precultures, expanded as described above and subject to the same in-process monitoring, control tests, and process parameters as the primary precultures, may be maintained and used to inoculate another 100 L seed bioreactor as needed When the preculture meets inoculum criteria, the contents of the culture bag(s) are transferred to the 100 L seed bioreactor containing CDH-A to target a seeding density of $\geq 0.3 \times 10^6$ VC/mL. The seed bioreactor culture pH, temperature, and dissolved oxygen concentration are controlled within ranges defined in the batch record. The culture is expanded until a cell density of $\geq 1.5 \times 10^6$ VC/mL and a culture viability of ≥80% are obtained. The culture is sampled for VCD, culture viability, and microscopic examination throughout the seed bioreactor process. Prior to inoculation of the 500 L production bioreactor, the culture is sampled for bioburden.

When the VCD of the seed bioreactor culture reaches $\geq 1.5 \times 10^6$ VC/mL, the culture may be used to inoculate the 500 L production bioreactor. Alternatively, a portion of the culture can be drawn from the 100 L seed bioreactor and the remaining culture diluted with fresh medium. Following this "draw and fill" process, the culture is allowed to expand to sufficient cell density to inoculate the 500 L production bioreactor. The maximum duration of the 100 L seed bioreactor culture is 9 days post-inoculation.

Stage 2—Bioreactor Production

In Stage 2, cell culture is continuously perfused in a 500 L production bioreactor using an alternating tangential flow hollow fiber filter cell retention system (ATF system). Cell culture permeate (harvest) is collected from the ATF system while cells are returned to the bioreactor, and the culture is replenished with fresh medium.

Manufacturing Procedure

The inoculation of the 500 L production bioreactor is performed by transferring the contents of the 100 L seed bioreactor into the 500 L production bioreactor containing CD (chemically defined) hybridoma medium supplemented with 6 mM L-glutamine, 0.5 mg/L mycophenolic acid, 2.5 mg/L hypoxanthine, and 50 mg/L xanthine (CDH-A). The volume transferred must be sufficient to target a seeding density of $\geq 0.3 \times 10^6$ viable cells (VC)/mL. The culture is maintained at a temperature of 34 to 38° C., a pH of 6.8 to 7.6, and a dissolved oxygen (DO) concentration of 1 to 100%.

Continuous perfusion is initiated, and culture is drawn from the 500 L bioreactor into the ATF system to separate the cells from the permeate. The permeate is filtered through the 0.2 μm ATF filter and collected as harvest in bioprocess containers (BPCs). The cells are returned to the bioreactor, and fresh CDH-A is supplied to maintain a constant culture volume. Viable cell density (VCD), culture viability, pH, DO, temperature and immunoglobulin G (IgG) content are monitored during the production run. The perfusion rate is gradually increased in proportion to VCD until a target rate of approximately one bioreactor volume per day is reached. The perfusion rate is controlled, not to exceed 1.20 bioreactor volumes per day. Retention of the ATF system is monitored to facilitate shutdown of an ATF filter prior to the IgG retention across the filter exceeding 50%.

When the VCD within the 500 L bioreactor reaches $8.0 \times 10^6$ VC/mL or on day 10, whichever comes first, the pH target is lowered from 7.2 to 7.1. Biomass removal is initiated at either day 20 or when a VCD of $12.0 \times 10^6$ VC/mL is reached, whichever comes first. Biomass is removed from the 500 L production bioreactor into BPCs at a rate of up to 20% bioreactor volumes per day. Each harvest is sampled for bioburden.

The continuous perfusion cell culture operation in the 500 L production bioreactor continues for up to 46 days post-inoculation. At the end of production, the culture is sampled for mycoplasma and adventitious virus testing. Harvest may be stored for 30 days at 2 to 8° C. after disconnection from the bioreactor.

Stage 3—Direct Product Capture (DPC)

In Stage 3, harvest from one or more 500 L production bioreactors is clarified and purified using a MabSelect™ (GE Healthcare Bio-Sciences, Pittsburgh, PA, USA) Protein A affinity chromatography column using an automated chromatography skid. The ustekinumab is captured from the harvest, and the cell culture impurities, including host-cell impurities, are removed. The resultant DPC eluate is frozen until further processing.

Protein A Column Preparation and Regeneration

Prior to harvest load, the packed MabSelect™ Protein A affinity chromatography column is equilibrated with 50 mM sodium phosphate, 150 mM NaCl, 0.1% polysorbate 80, pH 7.3 buffer (equilibration buffer). Conductivity and pH are monitored to ensure that the column is fully equilibrated. Samples are taken of the column effluent and are monitored to ensure microbial control. After use, the column is sanitized then flushed and stored, if applicable, in an appropriate storage condition.

Manufacturing Procedure

Harvest is sampled for bioburden, endotoxin, and immunoglobulin G content. 0.1 M ethylenediaminetetraaectic acid (EDTA), pH 8.0 buffer is added in line to the harvest to achieve a final concentration of 5 to 30 mM EDTA. The harvest is 0.2 μm filtered and loaded onto the Protein A column at a load ratio of 14 to 41 g/L and a flow rate of 300 to 500 cm/h. The column is washed with equilibration buffer at a flow rate of 300 to 500 cm/h until the UV absorbance at 280 nm ($A_{280}$) returns to ≤100 mAU/mm and is then washed with at least two additional column volumes (CVs) of equilibration buffer. The bound ustekinumab is washed with at least 4.5 CVs of 0.1 M sodium citrate, pH 5.0 buffer at a flow rate of 300 to 500 cm/h.

Ustekinumab is eluted using 0.1 M citrate, pH 3.5 at a flow rate of 300 to 500 cm/h. The collection of eluted product starts at an ascending $A_{280}$-signal of ≥50 mAU/mm path length and stops at a descending $A_{280}$-signal of ≥50 mAU/mm path length.

Following collection, the pH of the DPC eluate is adjusted to 5.8 to 6.2 by the addition of 1.0 M Tris buffer and/or 0.1 M sodium citrate buffer as needed. During the pH adjustment, the DPC eluate is mixed to ensure homogeneity of the solution. The pH adjusted DPC eluate is sampled for bioburden prior to filtration.

The pH-adjusted DPC eluate is filtered using a 0.2 μm end filter. The DPC eluate is aliquoted into polycarbonate containers. The filtered DPC eluate is sampled for analysis of monomer content, bioburden, endotoxin, and protein concentration (from which the step yield is calculated and expected to be ≥60%). The filtered DPC eluate can be held for a cumulative time of ≤48 hours at room temperature and ≤240 hours at 2 to 8° C. prior to storage at ≤−40° C. The DPC eluate may be stored frozen.

Stage 4—Thawing and Pooling of Direct Product Capture (DPC) Eluates

In Stage 4, the DPC eluates are thawed pooled and filtered prior to solvent/detergent viral inactivation.

Manufacturing Procedure

Frozen DPC eluates are thawed at room temperature. Thawing is complete once the eluates are visibly free of ice; thawing must not exceed 120 hours. The thawed eluates are pooled and 0.2 μm filtered into a closed vessel to obtain 2.7 to 5.4 kg protein. The filtered eluate is mixed to ensure homogeneity of the solution. Samples are taken for protein concentration, endotoxin, bioburden, and pH. The protein concentration is measured to be 4.5 to 59 g/L. The pH is then adjusted to 5.5 to 6.5 by the addition of either 1.0 M Tris or 1.0 M citric acid, as needed. The pooled DPC eluates may be stored up to 48 hours at room temperature prior to further processing in Stage 5.

Stage 5—Solvent/Detergent (S/D) Treatment of Pooled Direct Product Capture (DPC) Eluates In Stage 5, the pooled DPC eluates are incubated with Tri-n-butyl Phosphate (TNBP) and polysorbate 80 (solvent/detergent [S/D] treatment) to inactivate any lipid-enveloped viruses potentially present.

Manufacturing Procedure

An S/D stock solution containing 2% TNBP/10% polysorbate 80 (w/w) is transferred to the vessel containing the pooled DPC eluates at a ratio of 0.08 to 0.12 (v/v) to yield a final concentration of 0.2% TNBP/1% polysorbate 80 (w/v). The solution is mixed to ensure homogeneity of the solution, then transferred to the inactivation vessel. The ustekinumab and S/D treatment reagents are incubated at ≥15° C. with continuous mixing. Inactivation begins when the S/D-treated ustekinumab is completely transferred to the inactivation vessel and is complete when the cation exchange chromatography column-loading phase begins in Stage 6. Total inactivation time is ≥60 minutes. The total time from the start of S/D reagent addition to the end of the column-loading phase in Stage 6 is ≤36 hours.

Stage 6—Cation Exchange Chromatography

In Stage 6, the ustekinumab treated with solvent/detergent (S/D) is bound to an SP Sepharose XL (GE Healthcare Bio-Sciences, Pittsburgh, PA, USA) cation exchange chromatography column connected to an automated chromatography skid. Tri-n-butyl Phosphate (TNBP) and polysorbate 80 reagents, aggregates, and impurities are removed.

Cation Exchange Chromatography Column Preparation and Regeneration

Prior to use, the packed SP Sepharose XL cation exchange chromatography column is equilibrated with 30 mM sodium phosphate, pH 6.5 buffer (equilibration buffer). Conductivity and pH are monitored to ensure that the column is fully equilibrated. Samples are taken of the column effluent and are monitored to ensure microbial control. After use, the column is stripped of residual protein, regenerated and sanitized and is stored in an appropriate storage solution.

Manufacturing Procedure

S/D-treated ustekinumab is diluted in line with water for injection to maintain conductivity at 2.4 to 3.4 mS/cm and loaded onto the equilibrated SP Sepharose XL cation exchange chromatography column. All load, wash, and elution flow rates are 100 to 300 cm/h. The product to resin load ratio is 45.5 to 90.9 g ustekinumab/L resin. The column is washed with ≥3 column volumes of equilibration buffer. The ustekinumab is then eluted from the cation exchange column using 30 mM sodium phosphate, 50 mM sodium chloride, pH 6.5 buffer. Collection of the product is initiated when the column effluent UV absorbance at 280 nm ($A_{280}$) rises to a minimum of 25 mAU/mm. The $A_{280}$ peak is monitored, and collection is terminated when the effluent decreases to not less than 150 mAU/mm. The eluted product is sampled for analysis of bioburden.

The eluate is filtered through a 0.2 µm filter into a closed vessel. The cation exchange-purified ustekinumab is then mixed, and samples are taken for bioburden and endotoxin. Yield is monitored and expected to be ≥85%. The ustekinumab can be held at room temperature for up to 72 hours and at 2 to 8° C. for up to 7 days before further processing.

Stage 7—Anion Exchange Chromatography

In Stage 7, the ustekinumab is further purified by Q Sepharose™ XL (GE Healthcare Bio-Sciences, Pittsburgh, PA, USA) anion exchange chromatography using an automated chromatography skid. Ustekinumab flows through the resin while DNA, other impurities, and viruses are retained.

Anion Exchange Chromatography Column Preparation

Regeneration Prior to use, the packed Q Sepharose™ XL anion exchange chromatography column is equilibrated with 50 mM Tris, 50 mM sodium chloride, pH 8.0 (equilibration buffer). Conductivity and pH are monitored to ensure that the column is fully equilibrated. Samples are taken of the column effluent and are monitored to ensure microbial control. After use, the column is stripped of residual protein, regenerated, sanitized and is stored in an appropriate solution.

Manufacturing Procedure

Prior to loading, the pH of the cation exchange eluate is adjusted by adding 1.0 M Tris or 1.0 M citric acid as needed until the pH is 7.5 to 8.0. The eluate is mixed to ensure homogeneity of the solution. The pH-adjusted ustekinumab is loaded onto the Q Sepharose™ XL anion exchange column at a flow rate of 50 to 250 cm/h. The product to resin load ratio is 45.5 to 136.4 g ustekinumab/L resin.

Ustekinumab flows through the resin without binding and is collected once the UV absorbance at 280 nm ($A_{280}$) rises to a minimum of 30 mAU/mm. After the ustekinumab is loaded, the column is washed with equilibration buffer at a flow rate of 50 to 250 cm/h. The $A_{280}$ peak is monitored, and collection is terminated when the effluent decreases to not less than 50 mAU/mm. The eluted product is sampled for analysis of bioburden.

The ustekinumab is filtered through a 0.2 µm filter into a closed vessel, mixed, and sampled for bioburden and endotoxin. Yield is monitored and expected to be ≥85%. The anion exchange purified ustekinumab can be held at room temperature for up to 72 hours or at 2 to 8° C. for up to 7 days before further processing in Stage 8.

Stage 8—Virus Removal Filtration

In Stage 8, the anion exchange purified ustekinumab is diluted with 50 mM Tris, 50 mM NaCl, pH 8.0 buffer and filtered through a viral retentive filter (NFP®) to remove any potentially present viruses.

NFP Filtration System Preparation

Before use, the autoclaved single-use NFP filters are installed onto the sanitized NFP filtration system and flushed with water for injection (WFI) and then tested for water permeability. The filters are equilibrated with 50 mM Tris, 50 mM NaCl, pH 8.0 buffer (equilibration buffer). Conductivity and pH are monitored to ensure the system is fully equilibrated. Samples are taken of the buffer flush and are monitored to ensure microbial control. The NFP filtration system is sanitized after use and stored in an appropriate storage solution.

Manufacturing Procedure

Prior to filtration, the anion exchange purified ustekinumab is diluted with equilibration buffer to a concentration of ≤8.2 g/L. The diluted ustekinumab is then filtered through the NFP filters, and the NFP filtrate is collected in a stainless-steel vessel. An initial flow rate is determined within 5 minutes of the start of filtration, and the flux decay is monitored to ensure the flux decay from the initial flux (defined as 0% flux decay) does not exceed 85%. Once NFP filtration is complete, the skid is flushed with equilibration buffer and remaining product is collected in the stainless-steel vessel where it is mixed and sampled for endotoxin, bioburden, and protein concentration. Yield is monitored and expected to be ≥85%. Ustekinumab NFP-filtrate may be held at room temperature for up to 72 hours and at 2 to 8° C. for up to 7 days before further processing in Stage 9.

Stage 9—Concentration and Diafiltration

In Stage 9, the ultrafiltration step concentrates the ustekinumab, and the diafiltration step adds the formulation excipients and removes the in-process buffer salts.

Ultrafiltration System Preparation

Prior to use, the system is equilibrated with 50 mM Tris, 50 m M NaCl, pH 8.0 buffer. Conductivity and pH are monitored to ensure the system is fully equilibrated. Samples are taken of the buffer flush and are monitored to ensure microbial control. After use, the ultrafiltration system is sanitized. WFI is flushed through the system, and a normalized water permeability test is performed. If required, the ultrafiltration system is stored in an appropriate storage solution.

Manufacturing Procedure

The ustekinumab viral retentive filtrate is pre-concentrated to 36 to 82 g/L. The product is then diafiltered against 10 mM histidine, 8.5% sucrose, pH 5.7 buffer for ≥8 diavolumes, until the pH and conductivity of the permeate are within 5.5 to 5.9 and 400 to 700 µs/cm, respectively. The ustekinumab is further concentrated to not more than 180 g/L. Throughout the process, the trans-membrane pressure is monitored and controlled. Product is recovered with a buffer flush using 10 mM histidine, 8.5% sucrose, pH 5.7 buffer. The final concentration of ustekinumab is adjusted with this same buffer to a protein concentration of 86.7 to 95.8 g/L and is referred to as pre-formulated bulk (PFB). The yield for Stage 9 is monitored and expected to be ≥85%. If needed, the ustekinumab can be reprocessed to obtain the correct protein concentration by repeating the concentration steps through the ultrafiltration system. The product is mixed to ensure homogeneity of the solution. The ustekinumab PFB is stored at room temperature or at 2 to 8° C. for up to 48 hours.

Stage 10—Preparation of Formulated Bulk

In Stage 10, polysorbate 80 is added to the ustekinumab pre-formulated bulk (PFB) to obtain the formulated bulk (FB). The FB is filtered into polycarbonate containers for frozen storage.

Manufacturing Procedure

One percent polysorbate 80 is added at a ratio of 0.003 to 0.005 kg/L to the ustekinumab PFB in the closed PFB vessel and mixed to obtain the FB solution. The FB solution is mixed according to validated parameters to ensure homogeneity of the solution. The FB solution may be stored at room temperature or at 2 to 8° C. for up to 48 hours prior to filtration. The FB solution is filtered using a single-use pre-filter into the FB vessel and mixed. The mixed FB is then 0.2 μm filtered into polycarbonate containers. Samples are taken for release testing. The ustekinumab FB containers are stored at ≤−40° C.

Example 6—Application of the Gamma Distribution Transition Analysis (GDTA) Method for Chromatography Columns Used in STELARA® (Ustekinumab) Manufacturing This Example describes the application of the GDTA method to chromatography columns in purification during manufacturing of anti-TNF antibodies, e.g., the anti-TNFα antibody SIMPONI® (golimumab), e.g., a protein A affinity chromatography column in used during Stage 3 of manufacturing.

Stage 3—Protein a Affinity Chromatography Column

Figure 40:
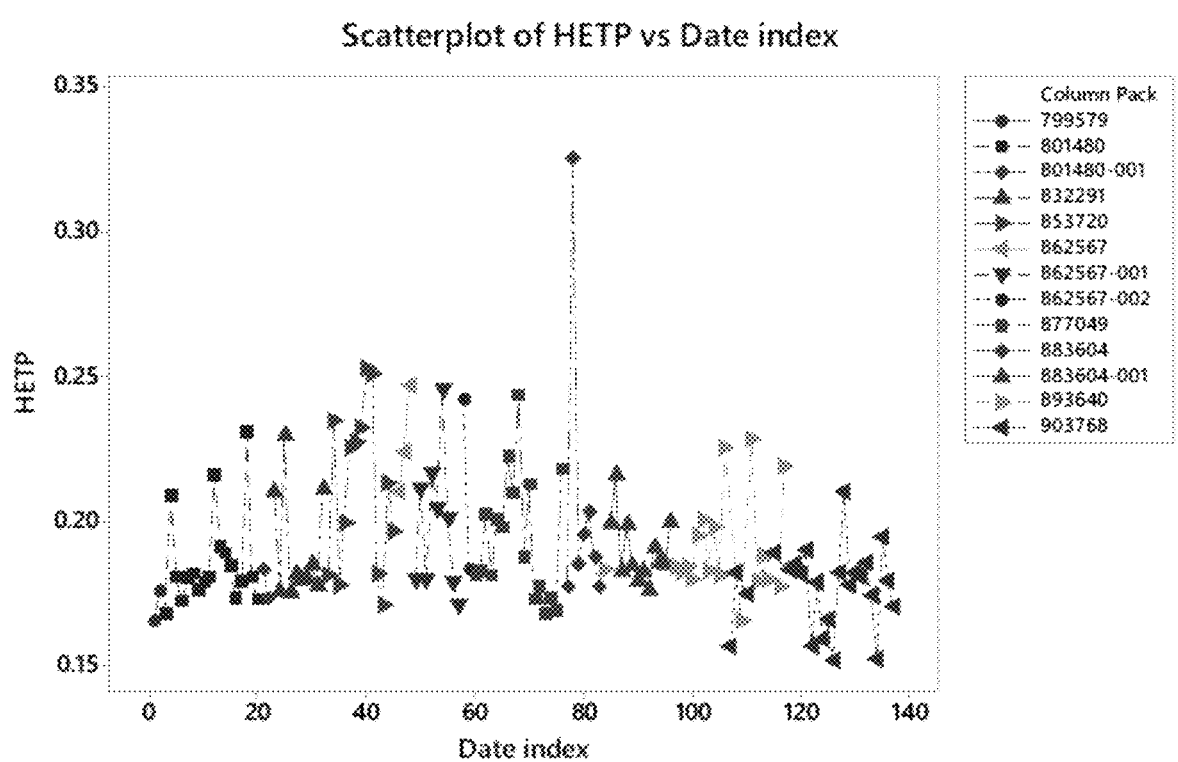
FIG. 40 is chart showing HETP results for a Stage 3 MabSelect™ Protein A affinity chromatography column for the wash 2 front generated during purification of STELARA® (ustekinumab).
Figure 41:
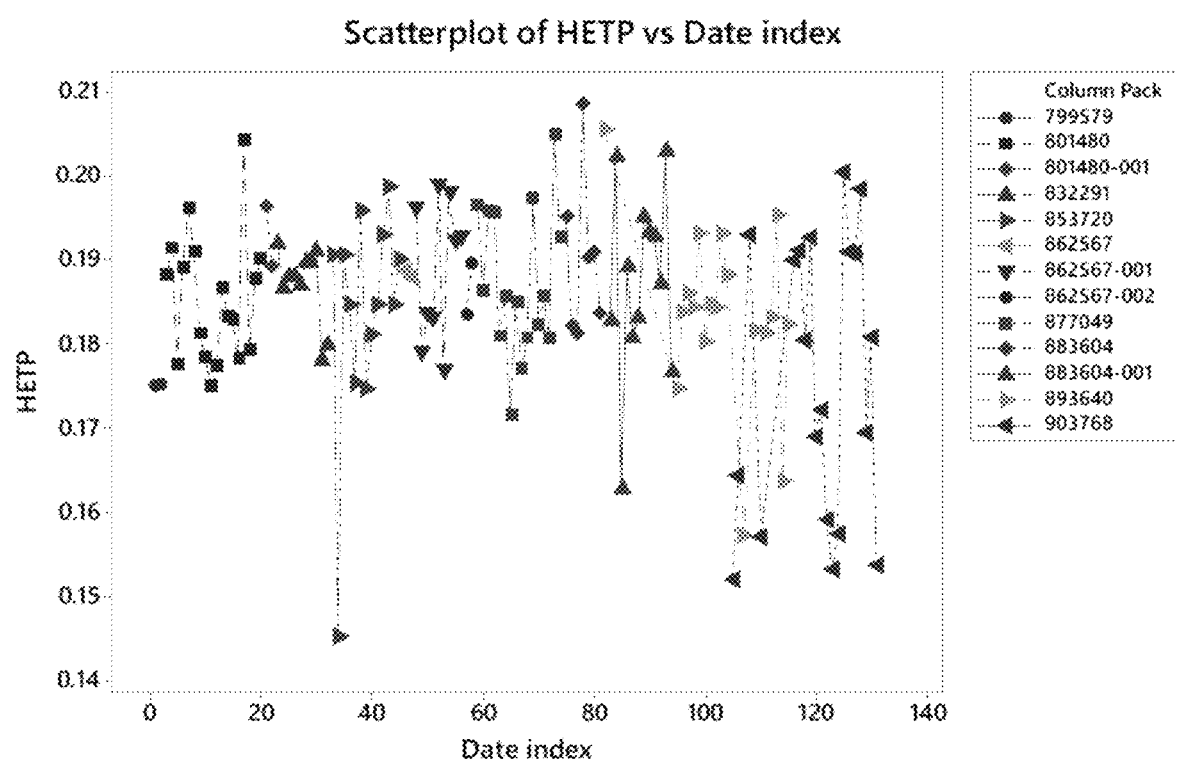
FIG. 41 is chart showing HETP results for a Stage 3 MabSelect™ Protein A affinity chromatography column for the front generated during elution of STELARA® (ustekinumab).

For the Stage 3, using a MabSelect™ Protein A affinity chromatography column, the analyzed transition fronts included, e.g., the wash 2 front (FIG. 40), and the front generated during elution (FIG. 41). Additional fronts generated during column cleaning post-sanitization, and the storage post-equilibration rinse step are also currently being evaluated for the MabSelect™ Protein A affinity chromatography column. The results shown represent the analysis of batches processed on 13 different column packs used for STELARA® (ustekinumab) manufacturing. Preliminary evaluation of the trends shows some drift apparent in column performance and some differences observed between column packs. A full analysis of this data, including comparison to other available batch information and column performance data will be completed in order to establish control limits for use in future implementation of the GDTA method for process monitoring in real time.

Example 7—Application of the Gamma Distribution Transition Analysis (GDTA) Method for Chromatography Columns Used in SIMPONI® (Golimumab) Manufacturing This Example describes the application of the GDTA method to chromatography columns in purification during manufacturing of the anti-TNFα antibody SIMPONI® (golimumab), e.g., a protein A affinity chromatography column in Stage 3, a cation exchange chromatography column in Stage 6, and an anion exchange chromatography column in Stage 7. These stages and the columns used in methods for manufacturing SIMPONI® (golimumab) are comparable to the ones used for manufacturing STELARA® (ustekinumab).

Stage 3—Protein a Affinity Chromatography Column

Figure 42:
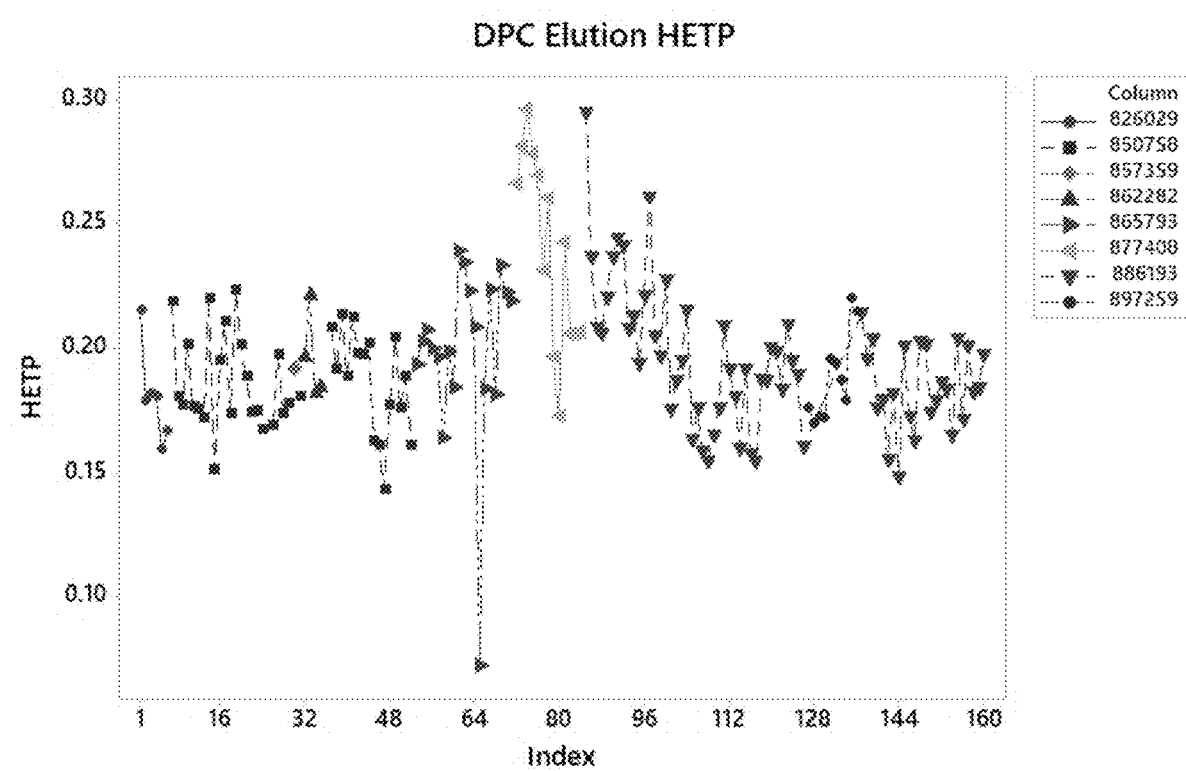
FIG. 42 is chart showing HETP results for a Stage 3 MabSelect™ Protein A affinity chromatography column for the front generated during elution of SIMPONI® (golimumab). DPC refers to Direct Product Capture of SIMPONI® (golimumab) on the MabSelect™ Protein A column.
Figure 43:
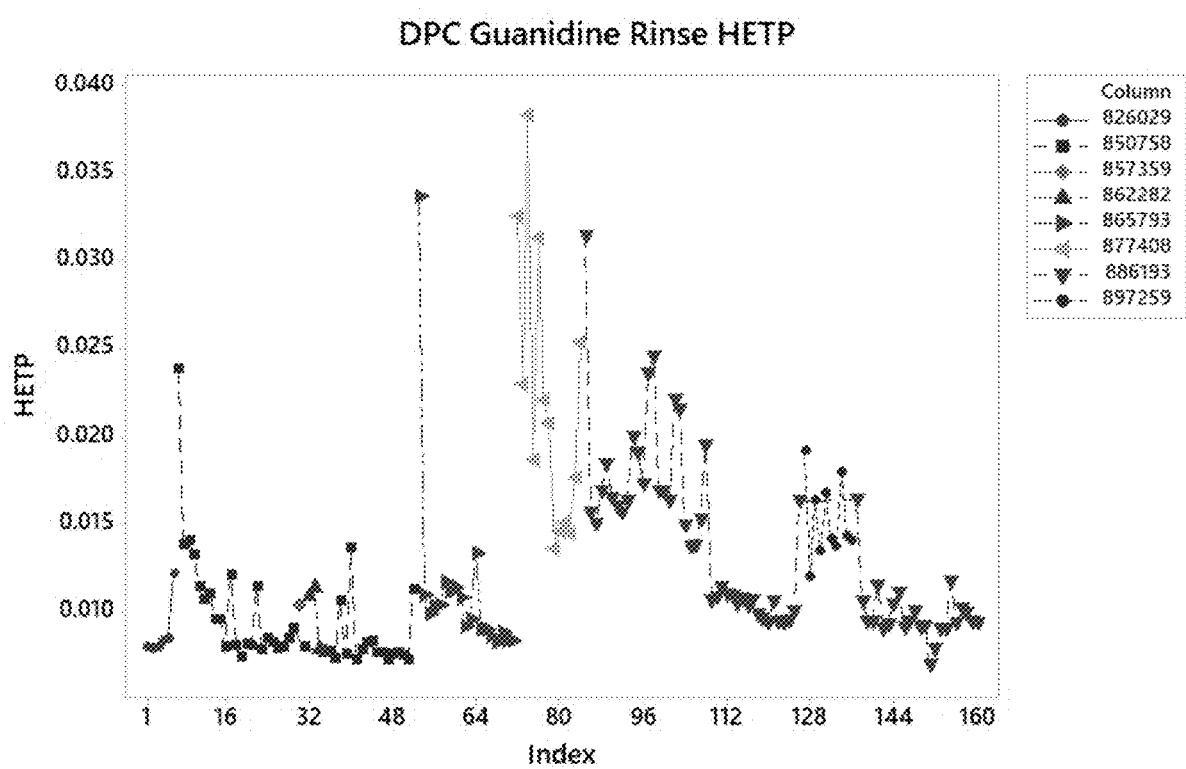
FIG. 43 is chart showing HETP results for a Stage 3 MabSelect™ Protein A affinity chromatography column for the front generated during sanitization with Guanidine HCl. DPC refers to Direct Product Capture of SIMPONI® (golimumab) on the MabSelect™ Protein A column.
Figure 44:
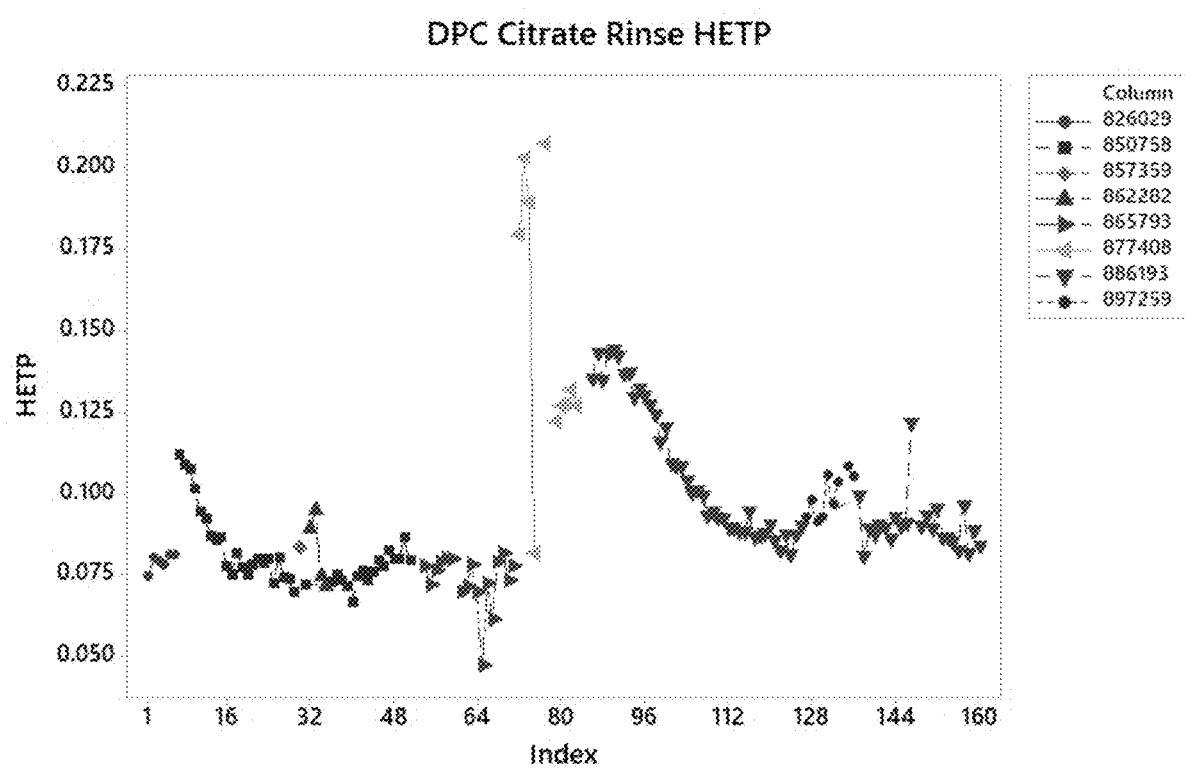
FIG. 44 is chart showing HETP results for a Stage 3 MabSelect™ Protein A affinity chromatography column for the front generated during post-sanitization rinsing with 0.1 M Sodium Citrate, pH 3.5. DPC refers to Direct Product Capture of SIMPONI® (golimumab) on the MabSelect™ Protein A column.

For the Stage 3, using a MabSelect™ Protein A affinity chromatography column, the analyzed transition fronts included, e.g., the elution front (FIG. 42), the front generated during sanitization with Guanidine HCl (FIG. 43), and the front generated during post-sanitization rinsing with 0.1 M Sodium Citrate, pH 3.5 (FIG. 44). The results shown represent the analysis of 160 batches of SIMPONI® (golimumab). Preliminary evaluation of the trends shows some drift apparent in column performance and some differences observed between column packs. A full analysis of this data, including comparison to other available batch information and column performance data will be completed in order to establish control limits for use in future implementation of the GDTA method for process monitoring in real time.

Stage 6—Cation Exchange Chromatography Column

Figure 45:
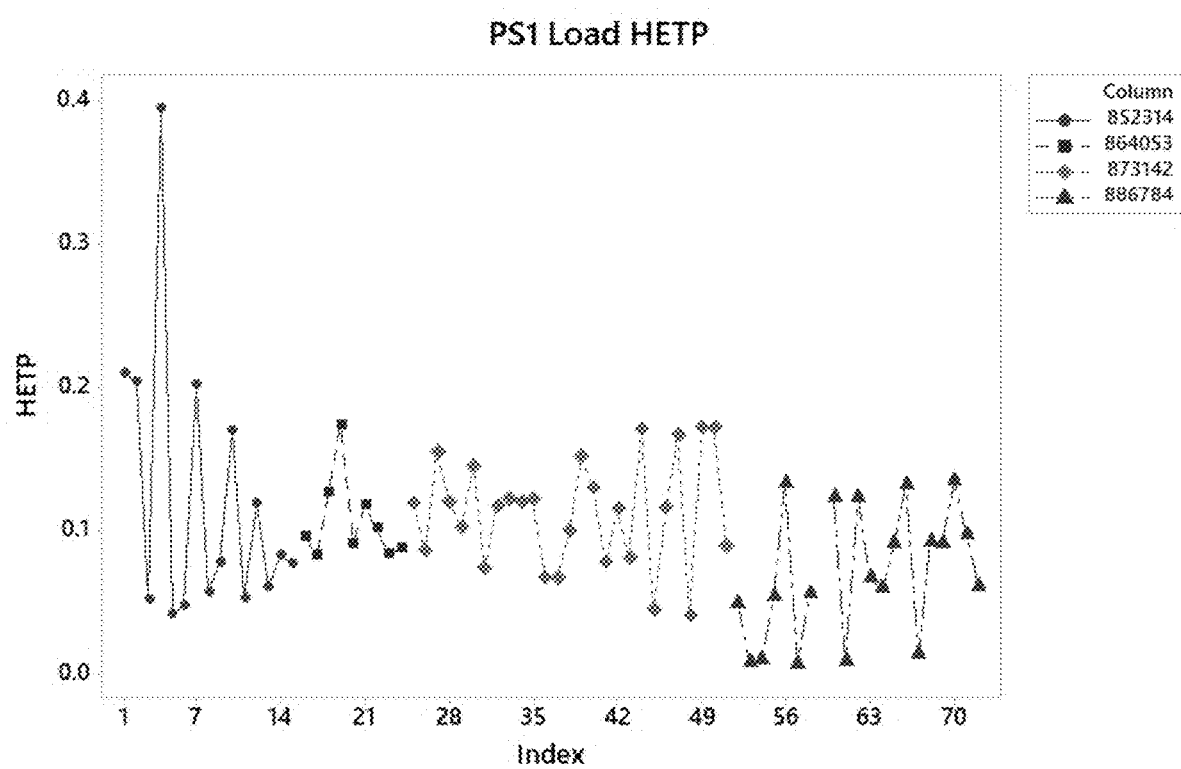
FIG. 45 is chart showing HETP results for a Stage 6 UNOsphere S™ cation exchange chromatography column front generated during loading of solvent/detergent (S/D) treated material containing SIMPONI® (golimumab). PS1 refers to Polishing Step 1 for SIMPONI® (golimumab) on the UNOsphere S™ column.
Figure 46:
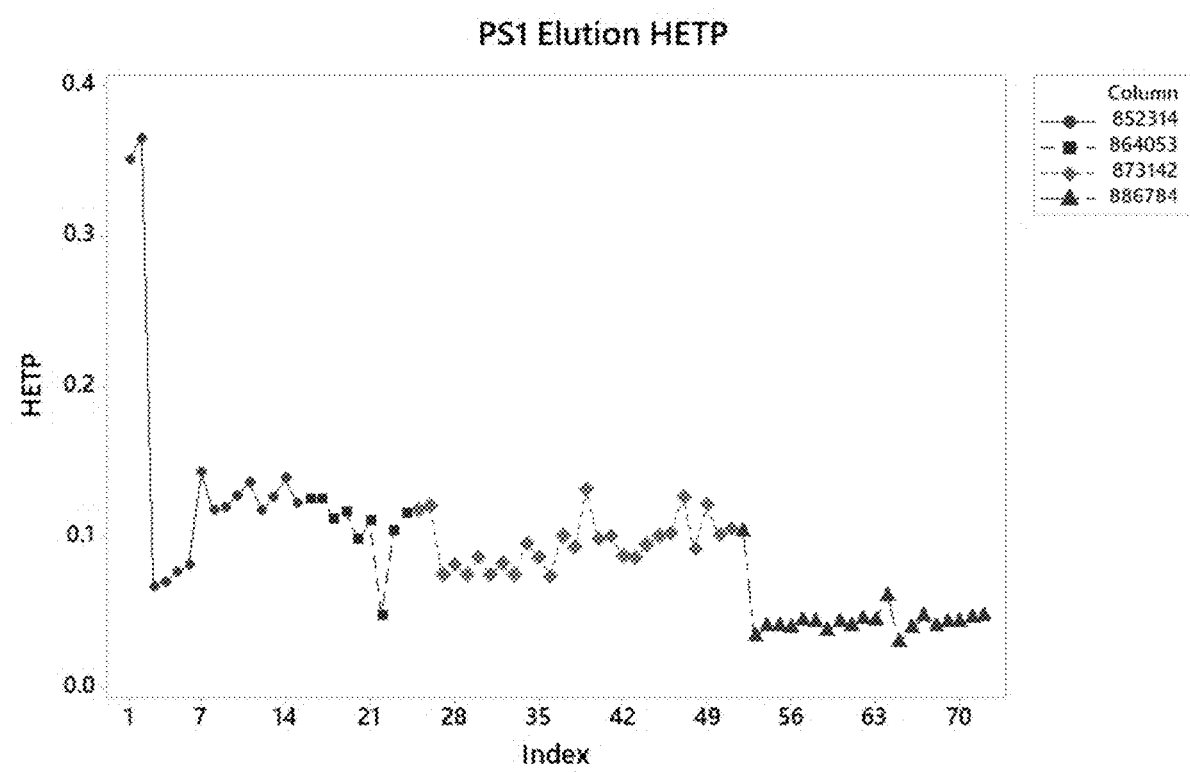
FIG. 46 is chart showing HETP results for a Stage 6 UNOsphere S™ cation exchange chromatography column front generated during elution of SIMPONI® (golimumab). PS1 refers to Polishing Step 1 for SIMPONI® (golimumab) on the UNOsphere S™ column.
Figure 47:
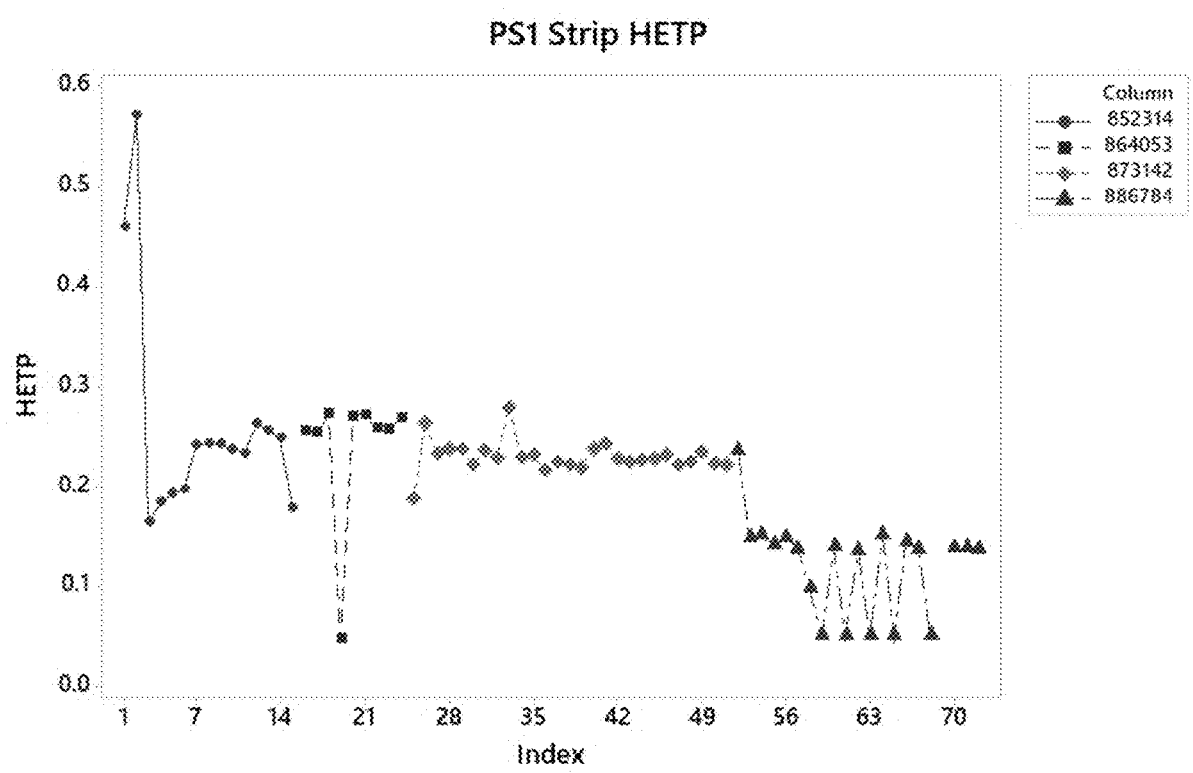
FIG. 47 is chart showing HETP results for a Stage 6 UNOsphere S™ cation exchange chromatography column front generated during the column strip. PS1 refers to Polishing Step 1 for SIMPONI® (golimumab) on the UNOsphere S™ column.

For the Stage 6, using a UNOsphere S™ cation exchange chromatography column, the analyzed transition fronts included, e.g., the front generated during loading of solvent/detergent (S/D) treated material (FIG. 45), the front generated during elution (FIG. 46), and the front generated during the strip (FIG. 47). The results shown represent the analysis of 72 batches of SIMPONI® (golimumab). Preliminary evaluation of the trends shows some drift apparent in column performance and some differences observed between column packs. A full analysis of this data, including comparison to other available batch information and column performance data will be completed in order to establish control limits for use in future implementation of the GDTA method for process monitoring in real time.

Stage 7—Anion Exchange Chromatography Column

Figure 48:
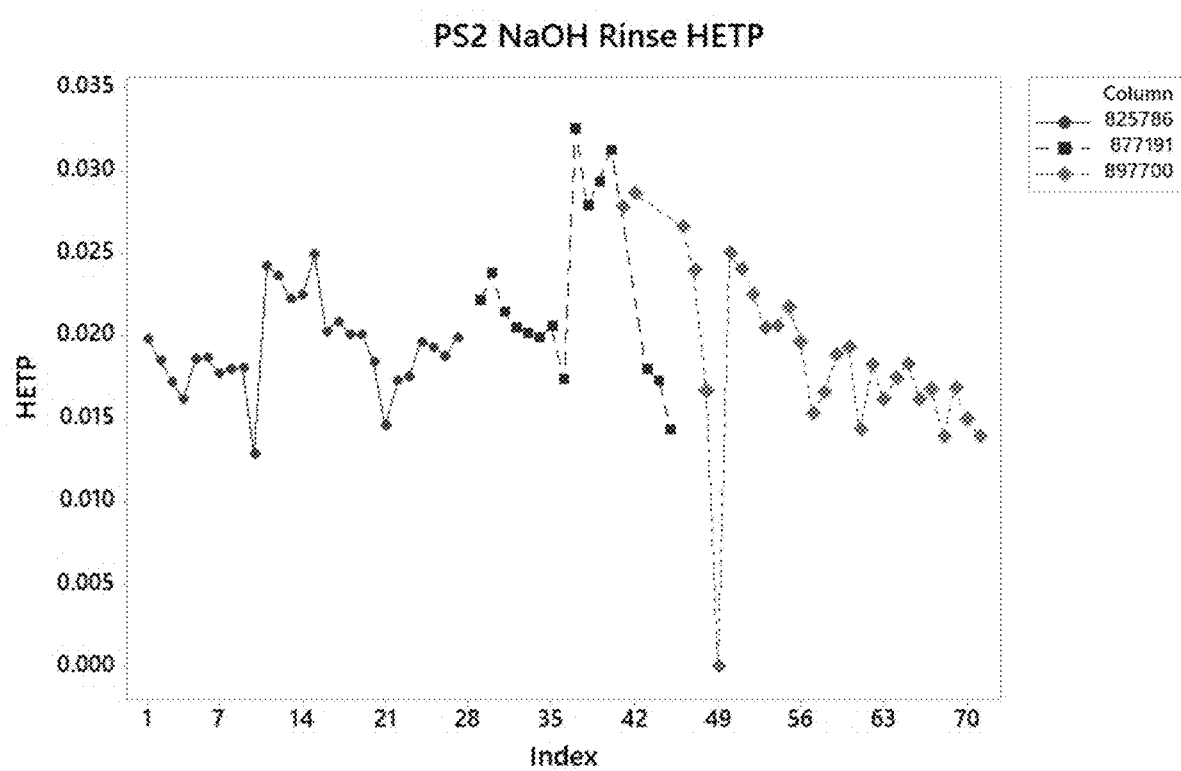
FIG. 48 is chart showing HETP results for a Stage 7 Q Sepharose™ XL anion exchange chromatography column front generated during cleaning with Sodium Hydroxide. PS2 refers to Polishing Step 2 for SIMPONI® (golimumab) on the Q Sepharose™ XL column.
Figure 49:
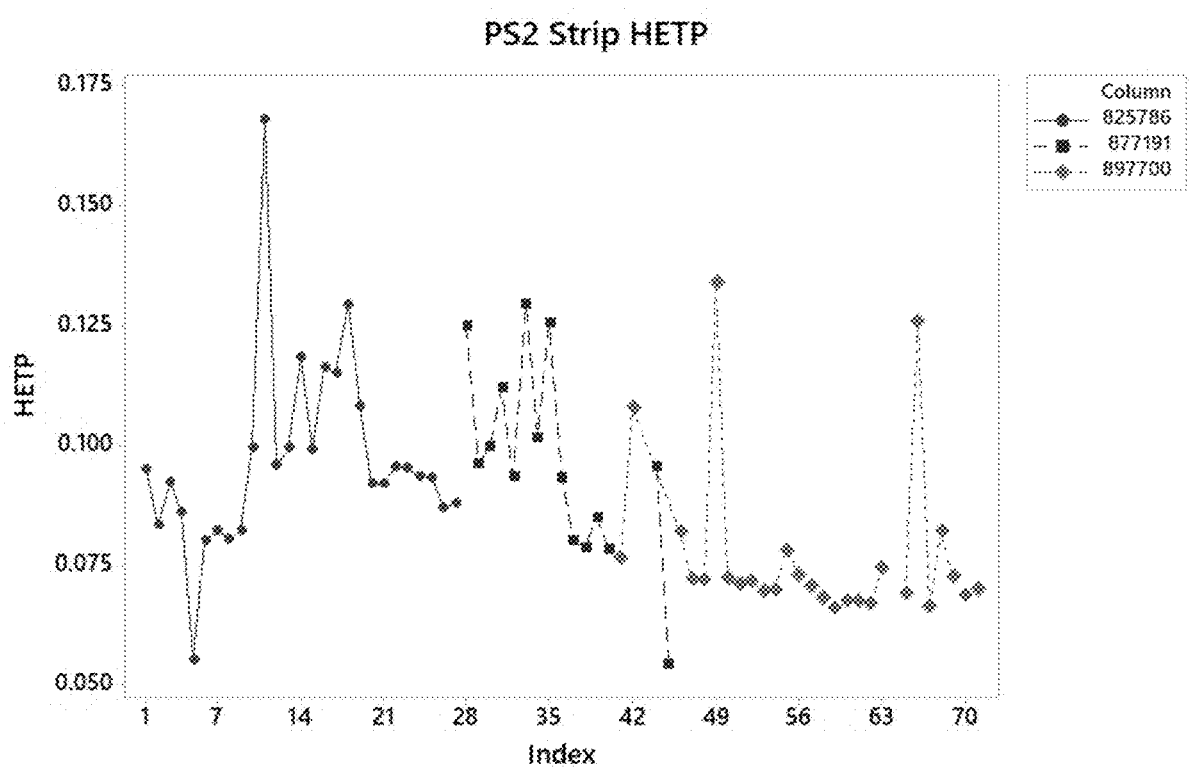
FIG. 49 is chart showing HETP results for a Stage 7 Q Sepharose™ XL anion exchange chromatography column front generated during the column strip. PS2 refers to Polishing Step 2 for SIMPONI® (golimumab) on the Q Sepharose™ XL column.

For the Stage 7, using a Q Sepharose™ XL anion exchange chromatography column, the analyzed transition fronts included, e.g., the front generated during cleaning with Sodium Hydroxide (FIG. 48) and the front generated during strip (FIG. 49). The results shown represent the analysis of 71 batches of SIMPONI® (golimumab). Preliminary evaluation of the trends shows some drift apparent in column performance and some differences observed between column packs. A full analysis of this data, including comparison to other available batch information and column performance data will be completed in order to establish control limits for use in future implementation of the GDTA method for process monitoring in real time.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A system for producing an anti-IL-12/IL-23p40 antibody, a specific pharmaceutical composition of the antibody, and an antigen binding fragment thereof,
    wherein the system comprises a computing device, a chromatography column, a detector communicatively connected to the computing device, and at least one mobile phase;
        wherein the detector is configured to collect a column outlet signal and accumulated flow parameters at two or more intervals of at least one mobile phase transition front during a first operation of the chromatography column comprising column packing; and
        wherein the computing device comprises a processor and a non-transitory computer-readable medium with instructions stored thereon, which, when executed by the processor, perform steps comprising:
        a) determining a model gamma cumulative distribution curve based on the collected column outlet signal and accumulated flow parameters for the at least one mobile phase transition front using Formula Ia for a rising transition front or Formula Ib for a falling transition front, $$C = 1 - \frac{1}{\Gamma(k)} \gamma\left(k, \frac{V - V_i}{\theta}\right) \quad \text{Formula Ia}$$

or $$C = \frac{1}{\Gamma(k)} \gamma\left(k, \frac{V - V_i}{\theta}\right) \quad \text{Formula Ib}$$

wherein C is the column outlet signal for a given V, V is the accumulated flow divided by the column volume, and k, θ, and Vi are the shape, scale, and offset parameters, respectively, used to define the model gamma cumulative distribution curve;

b) calculating a height equivalent theoretical plate (HETP) value for the at least one mobile phase transition front using Formula II and the model gamma cumulative distribution curve parameters of k, θ, and Vi, $$HEPT = \frac{\sigma^2}{\mu^2} L \quad \text{Formula II}$$

wherein $$\mu = k\theta + V_i$$

-continued $$\sigma = \sqrt{k\theta^2}$$

$L$ = column length;

and c) assessing the quality of the chromatography column packing based on said calculated HETP value.

2. The system of claim 1, wherein the detector is configured to collect column outlet signals and accumulated flow parameters at two or more intervals of a corresponding mobile phase transition front during one or more subsequent uses of the chromatography column packing; and wherein the computing device, performs steps comprising:

a) said determining and said calculating using the column outlet signals and accumulated flow parameters collected during each of the one or more subsequent uses of the chromatography column packing;

b) determining an HETP value of the chromatography column packing during each of said one or more subsequent uses based on said performing;

c) compiling a trend of the determined HETP values of the chromatography column packing of the one or more subsequent uses; and d) identifying a change in the quality of the chromatography column packing based on said compiled trend, wherein said conditioning, replacing or repacking of the chromatography column is based on said identifying.

3. The system of claim 1, wherein the detector is configured to collect column outlet signals and accumulated flow parameters of two or more different mobile phase transition fronts during said first operation of the column packing, and wherein the computing device performs steps comprising:

determining and calculating using the column outlet signals and accumulated flow parameters collected for each of the two or more different mobile phase transition fronts independently to calculate an HETP value for each of the two of more different mobile phase transition fronts.

4. The system of claim 1, wherein the chromatography column is selected from the group consisting of: a Protein A affinity chromatography column, a cation exchange chromatography column, and an anion exchange chromatography column.

5. The system of claim 4, wherein the mobile phase transition front comprises at least one selected from the group consisting of:

a) a mobile phase transition front in the Protein A affinity chromatography column that is generated from one or more fronts selected from the group consisting of: a wash front generated during purification of the anti-IL-12/IL-23p40 antibodies, a front generated during elution of the anti-IL-12/IL-23p40 antibodies, a front generated during sanitization of the column with guanidine HCl, and a front generated during post-sanitization rinsing of the column with 0.1 M sodium citrate, pH 3.5;

b) a mobile phase transition front in the cation exchange chromatography column is generated from one or more fronts selected from the group consisting of: a front generated during loading of solvent/detergent (S/D) treated material comprising the anti-IL-12/IL-23p40 antibodies, a front generated during elution of the anti-IL-12/IL-23p40 antibodies, and a front generated during a column strip; and c) a mobile phase transition front in the anion exchange chromatography column is generated from one or more fronts selected from the group consisting of: a front generated during cleaning of the column with sodium hydroxide and a front generated during a column strip.

6. The system of claim 1, wherein the detector is further coupled to an output of the chromatography column.

7. The system of claim 2, wherein the chromatography column is selected from the group consisting of: a Protein A affinity chromatography column, a cation exchange chromatography column, and an anion exchange chromatography column.

8. The system of claim 7, wherein the mobile phase transition front comprises at least one selected from the group consisting of:

a) a mobile phase transition front in the Protein A affinity chromatography column that is generated from one or more fronts selected from the group consisting of: a wash front generated during purification of the anti-IL-12/IL-23p40 antibodies, a front generated during elution of the anti-IL-12/IL-23p40 antibodies, a front generated during sanitization of the column with guanidine HCl, and a front generated during post-sanitization rinsing of the column with 0.1 M sodium citrate, pH 3.5;

b) a mobile phase transition front in the cation exchange chromatography column is generated from one or more fronts selected from the group consisting of: a front generated during loading of solvent/detergent (S/D) treated material comprising the anti-IL-12/IL-23p40 antibodies, a front generated during elution of the anti-IL-12/IL-23p40 antibodies, and a front generated during a column strip; and c) a mobile phase transition front in the anion exchange chromatography column is generated from one or more fronts selected from the group consisting of: a front generated during cleaning of the column with sodium hydroxide and a front generated during a column strip.

9. The system of claim 2, wherein the detector is further coupled to an output of the chromatography column.

10. The system of claim 3, wherein the chromatography column is selected from the group consisting of: a Protein A affinity chromatography column, a cation exchange chromatography column, and an anion exchange chromatography column.

11. The system of claim 10, wherein the mobile phase transition front comprises at least one selected from the group consisting of:

a) a mobile phase transition front in the Protein A affinity chromatography column that is generated from one or more fronts selected from the group consisting of: a wash front generated during purification of the anti-IL-12/IL-23p40 antibodies, a front generated during elution of the anti-IL-12/IL-23p40 antibodies, a front generated during sanitization of the column with guanidine HCl, and a front generated during post-sanitization rinsing of the column with 0.1 M sodium citrate, pH 3.5;

b) a mobile phase transition front in the cation exchange chromatography column is generated from one or more fronts selected from the group consisting of: a front generated during loading of solvent/detergent (S/D) treated material comprising the anti-IL-12/IL-23p40 antibodies, a front generated during elution of the anti-IL-12/IL-23p40 antibodies, and a front generated during a column strip; and c) a mobile phase transition front in the anion exchange chromatography column is generated from one or more fronts selected from the group consisting of: a front generated during cleaning of the column with sodium hydroxide and a front generated during a column strip.

12. The system of claim 3, wherein the detector is further coupled to an output of the chromatography column.

13. A system comprising a computing device, a chromatography column, a detector communicatively connected to the computing device, and at least one mobile phase;
wherein the detector is configured to collect a column outlet signal and accumulated flow parameters at two or more intervals of at least one mobile phase transition front during a first operation of the chromatography column comprising column packing; and
wherein the computing device comprises a processor and a non-transitory computer-readable medium with instructions stored thereon, which, when executed by the processor, perform steps comprising:
a) determining a model gamma cumulative distribution curve based on the collected column outlet signal and accumulated flow parameters for the at least one mobile phase transition front using Formula Ia for a rising transition front or Formula Ib for a falling transition front, $$C = 1 - \frac{1}{\Gamma(k)}\gamma\left(k, \frac{V - V_i}{\theta}\right) \quad \text{Formula Ia}$$

or $$C = \frac{1}{\Gamma(k)}\gamma\left(k, \frac{V - V_i}{\theta}\right) \quad \text{Formula Ib}$$

wherein C is the column outlet signal for a given V, V is the accumulated flow divided by the column volume, and k, 0, and Vi are the shape, scale, and offset parameters, respectively, used to define the model gamma cumulative distribution curve;

b) calculating a height equivalent theoretical plate (HETP) value for the at least one mobile phase transition front using Formula II and the model gamma cumulative distribution curve parameters of k, 0, and Vi, $$HEPT = \frac{\sigma^2}{\mu^2}L \quad \text{Formula II}$$

wherein $\mu = k\theta + V_i$ $\sigma = \sqrt{k\theta^2}$ $L$ = column length;

and c) assessing the quality of the chromatography column packing based on said calculated HETP value.

* * * * *

SEQUENCE LISTING

```
<160> NUMBER OF SEQ ID NOS: 11

<210> SEQ ID NO 1
<211> LENGTH: 5
<212> TYPE: PRT
<213> ORGANISM: Homo sapiens

<400> SEQUENCE: 1

Thr Tyr Trp Leu Gly
1               5

<210> SEQ ID NO 2
<211> LENGTH: 17
```

```
<212> TYPE: PRT
<213> ORGANISM: Homo sapiens

<400> SEQUENCE: 2

Ile Met Ser Pro Val Asp Ser Asp Ile Arg Tyr Ser Pro Ser Phe Gln
1               5                   10                  15

Gly

<210> SEQ ID NO 3
<211> LENGTH: 10
<212> TYPE: PRT
<213> ORGANISM: Homo sapiens

<400> SEQUENCE: 3

Arg Arg Pro Gly Gln Gly Tyr Phe Asp Phe
1               5                   10

<210> SEQ ID NO 4
<211> LENGTH: 11
<212> TYPE: PRT
<213> ORGANISM: Homo sapiens

<400> SEQUENCE: 4

Arg Ala Ser Gln Gly Ile Ser Ser Trp Leu Ala
1               5                   10

<210> SEQ ID NO 5
<211> LENGTH: 7
<212> TYPE: PRT
<213> ORGANISM: Homo sapiens

<400> SEQUENCE: 5

Ala Ala Ser Ser Leu Gln Ser
1               5

<210> SEQ ID NO 6
<211> LENGTH: 9
<212> TYPE: PRT
<213> ORGANISM: Homo sapiens

<400> SEQUENCE: 6

Gln Gln Tyr Asn Ile Tyr Pro Tyr Thr
1               5

<210> SEQ ID NO 7
<211> LENGTH: 119
<212> TYPE: PRT
<213> ORGANISM: Homo sapiens

<400> SEQUENCE: 7

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Leu Gly Trp Val Arg Gln Met Pro Gly Lys Gly Leu Asp Trp Ile
        35                  40                  45

Gly Ile Met Ser Pro Val Asp Ser Asp Ile Arg Tyr Ser Pro Ser Phe
    50                  55                  60

Gln Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95
```

```
Ala Arg Arg Arg Pro Gly Gln Gly Tyr Phe Asp Phe Trp Gly Gln Gly
            100                 105                 110

Thr Leu Val Thr Val Ser Ser
        115

<210> SEQ ID NO 8
<211> LENGTH: 108
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Tyr
                85                  90                  95

Thr Phe Gly Gln Gly Thr Lys Leu Glu Ile Lys Arg
            100                 105

<210> SEQ ID NO 9
<211> LENGTH: 503
<212> TYPE: PRT
<213> ORGANISM: Homo sapiens

<400> SEQUENCE: 9

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190
```

```
Tyr Leu Asn Ala Ser Ile Trp Glu Leu Lys Lys Asp Val Tyr Val
            195                 200                 205

Glu Leu Asp Trp Tyr Pro Asp Ala Pro Gly Glu Met Val Val Leu Thr
210                 215                 220

Cys Asp Thr Pro Glu Glu Asp Gly Ile Thr Trp Thr Leu Asp Gln Ser
225                 230                 235                 240

Ser Glu Val Leu Gly Ser Gly Lys Thr Leu Thr Ile Gln Val Lys Glu
            245                 250                 255

Phe Gly Asp Ala Gly Gln Tyr Thr Cys His Lys Gly Gly Glu Val Leu
            260                 265                 270

Ser His Ser Leu Leu Leu Leu His Lys Lys Glu Asp Gly Ile Trp Ser
            275                 280                 285

Thr Asp Ile Leu Lys Asp Gln Lys Glu Pro Lys Asn Lys Thr Phe Leu
            290                 295                 300

Arg Cys Glu Ala Lys Asn Tyr Ser Gly Arg Phe Thr Cys Trp Trp Leu
305                 310                 315                 320

Thr Thr Ile Ser Thr Asp Leu Thr Phe Ser Val Lys Ser Ser Arg Gly
                325                 330                 335

Ser Ser Asp Pro Gln Gly Val Thr Cys Gly Ala Ala Thr Leu Ser Ala
            340                 345                 350

Glu Arg Val Arg Gly Asp Asn Lys Glu Tyr Glu Tyr Ser Val Glu Cys
            355                 360                 365

Gln Glu Asp Ser Ala Cys Pro Ala Ala Glu Glu Ser Leu Pro Ile Glu
        370                 375                 380

Val Met Val Asp Ala Val His Lys Leu Lys Tyr Glu Asn Tyr Thr Ser
385                 390                 395                 400

Ser Phe Phe Ile Arg Asp Ile Ile Lys Pro Asp Pro Pro Lys Asn Leu
                405                 410                 415

Gln Leu Lys Pro Leu Lys Asn Ser Arg Gln Val Glu Val Ser Trp Glu
            420                 425                 430

Tyr Pro Asp Thr Trp Ser Thr Pro His Ser Tyr Phe Ser Leu Thr Phe
            435                 440                 445

Cys Val Gln Val Gln Gly Lys Ser Lys Arg Glu Lys Lys Asp Arg Val
450                 455                 460

Phe Thr Asp Lys Thr Ser Ala Thr Val Ile Cys Arg Lys Asn Ala Ser
465                 470                 475                 480

Ile Ser Val Arg Ala Gln Asp Arg Tyr Tyr Ser Ser Ser Trp Ser Glu
                485                 490                 495

Trp Ala Ser Val Pro Cys Ser
            500

<210> SEQ ID NO 10
<211> LENGTH: 449
<212> TYPE: PRT
<213> ORGANISM: Homo sapiens

<400> SEQUENCE: 10

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Leu Gly Trp Val Arg Gln Met Pro Gly Lys Gly Leu Asp Trp Ile
        35                  40                  45

Gly Ile Met Ser Pro Val Asp Ser Asp Ile Arg Tyr Ser Pro Ser Phe
```

```
            50                  55                  60
        Gln Gly Gln Val Thr Met Ser Val Asp Lys Ser Ile Thr Thr Ala Tyr
         65                  70                  75                  80

Leu Gln Trp Asn Ser Leu Lys Ala Ser Asp Thr Ala Met Tyr Tyr Cys
                             85                  90                  95

Ala Arg Arg Arg Pro Gly Gln Gly Tyr Phe Asp Phe Trp Gly Gln Gly
                        100                 105                 110

Thr Leu Val Thr Val Ser Ser Ser Thr Lys Gly Pro Ser Val Phe
                    115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
        145                 150                 155                 160

Asn Ser Gly Ala Leu Thr Ser Gly Val His Thr Phe Pro Ala Val Leu
                            165                 170                 175

Gln Ser Ser Gly Leu Tyr Ser Leu Ser Ser Val Val Thr Val Pro Ser
                        180                 185                 190

Ser Ser Leu Gly Thr Gln Thr Tyr Ile Cys Asn Val Asn His Lys Pro
                    195                 200                 205

Ser Asn Thr Lys Val Asp Lys Arg Val Glu Pro Lys Ser Cys Asp Lys
                210                 215                 220

Thr His Thr Cys Pro Pro Cys Pro Ala Pro Glu Leu Leu Gly Gly Pro
        225                 230                 235                 240

Ser Val Phe Leu Phe Pro Pro Lys Pro Lys Asp Thr Leu Met Ile Ser
                            245                 250                 255

Arg Thr Pro Glu Val Thr Cys Val Val Val Asp Val Ser His Glu Asp
                        260                 265                 270

Pro Glu Val Lys Phe Asn Trp Tyr Val Asp Gly Val Glu Val His Asn
                    275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
        305                 310                 315                 320

Tyr Lys Cys Lys Val Ser Asn Lys Ala Leu Pro Ala Pro Ile Glu Lys
                            325                 330                 335

Thr Ile Ser Lys Ala Lys Gly Gln Pro Arg Glu Pro Gln Val Tyr Thr
                        340                 345                 350

Leu Pro Pro Ser Arg Asp Glu Leu Thr Lys Asn Gln Val Ser Leu Thr
                    355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
        385                 390                 395                 400

Asp Ser Asp Gly Ser Phe Phe Leu Tyr Ser Lys Leu Thr Val Asp Lys
                            405                 410                 415

Ser Arg Trp Gln Gln Gly Asn Val Phe Ser Cys Ser Val Met His Glu
                        420                 425                 430

Ala Leu His Asn His Tyr Thr Gln Lys Ser Leu Ser Leu Ser Pro Gly
                    435                 440                 445

Lys

<210> SEQ ID NO 11
<211> LENGTH: 214
```

```
<212> TYPE: PRT
<213> ORGANISM: Homo sapiens

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```